US012576223B2

(12) United States Patent
Jacobs, Jr. et al.

(10) Patent No.: US 12,576,223 B2
(45) Date of Patent: *Mar. 17, 2026

(54) DRUG DELIVERY SYSTEMS, DEVICES, AND METHODS

(71) Applicant: Predictably Human, Inc., Darien, CT (US)

(72) Inventors: Robert Francis Jacobs, Jr., Norwalk, CT (US); J. Robert Geiman, Boston, MA (US); Douglas Philip Dean, Engelberg (CH); James McDowell Davis, Jr., Durham, NC (US); Carl David Marci, Boston, MA (US); Liad Yamin, New York, NY (US); Aron Cohen, Jersey City, NJ (US); Michael DeTienne, New York, NY (US)

(73) Assignee: Predictably Human, Inc., Darien, CT (US)

( * ) Notice: Subject to any disclaimer, the term of this patent is extended or adjusted under 35 U.S.C. 154(b) by 826 days.

This patent is subject to a terminal disclaimer.

(21) Appl. No.: 17/812,326

(22) Filed: Jul. 13, 2022

(65) Prior Publication Data

US 2023/0023805 A1     Jan. 26, 2023

Related U.S. Application Data

(63) Continuation-in-part of application No. 17/650,783, filed on Feb. 11, 2022, now Pat. No. 12,114,695.
(Continued)

(51) Int. Cl.
*A61M 15/06*     (2006.01)
*A24F 40/05*     (2020.01)
(Continued)

(52) U.S. Cl.
CPC ............. *A61M 15/06* (2013.01); *A24F 40/05* (2020.01); *A24F 40/10* (2020.01); *A24F 40/30* (2020.01);
(Continued)

(58) Field of Classification Search
CPC .......... A24F 40/10; A24F 40/30; A24F 40/42; A24F 40/51; A24F 40/53; A24F 40/57;
(Continued)

(56) References Cited

U.S. PATENT DOCUMENTS 6,803,545 B2     10/2004     Blake et al.
8,256,433 B2      9/2012     Gonda
(Continued)

FOREIGN PATENT DOCUMENTS

CA          2446102          4/2004
CN         105324045         2/2016
(Continued)

OTHER PUBLICATIONS

Talih, S., Salman, R., El-Hage, R. et al. Effect of free-base and protonated nicotine on nicotine yield from electronic cigarettes with varying power and liquid vehicle. Sci Rep 10, 16263 (2020). https://doi.org/10.1038/s41598-020-73385-6.*
(Continued)

*Primary Examiner* — Joseph D. Boecker
(74) *Attorney, Agent, or Firm* — KNOBBE, MARTENS, OLSON & BEAR, LLP

(57)          ABSTRACT

Systems and methods of an electronic drug delivery system for use in a treatment program (e.g., a smoking cessation program). The delivery system can include a mobile platform and a hand-held inhalation delivery device having a controller circuit coupled to a power source, sensors, aerosolizer drivers, and a rescue button, and a pod removably coupled to the delivery device. The delivery system gener-
(Continued)

ates an aerosol mixture from substances in the pod in accordance with the treatment program, and delivers the aerosol mixture for inhalation by a user. The controller circuit individually and dynamically controls the aerosolizer drivers to generate signals that drive a plurality of thermal, or non-thermal, aerosolizers of the pod to generate individually tailored aerosol mixtures from multiple substances in the aerosolizer pod. The generated aerosol mixtures can have various percentages of the substances, and have different aerosol droplet sizes during different portions of the treatment program.

20 Claims, 53 Drawing Sheets

Related U.S. Application Data

(60) Provisional application No. 63/263,863, filed on Nov. 10, 2021, provisional application No. 63/261,638, filed on Sep. 24, 2021, provisional application No. 63/203,324, filed on Jul. 16, 2021.

(51) Int. Cl.

| | |
|---|---|
| *A24F 40/10* | (2020.01) |
| *A24F 40/30* | (2020.01) |
| *A24F 40/42* | (2020.01) |
| *A24F 40/46* | (2020.01) |
| *A24F 40/485* | (2020.01) |
| *A24F 40/51* | (2020.01) |
| *A24F 40/53* | (2020.01) |
| *A24F 40/57* | (2020.01) |
| *A24F 40/60* | (2020.01) |
| *A24F 47/00* | (2020.01) |
| *A61M 15/00* | (2006.01) |

(52) U.S. Cl.
CPC .............. *A24F 40/42* (2020.01); *A24F 40/46* (2020.01); *A24F 40/485* (2020.01); *A24F 40/51* (2020.01); *A24F 40/53* (2020.01); *A24F 40/57* (2020.01); *A24F 40/60* (2020.01); *A24F 47/00* (2013.01); *A61M 15/0021* (2014.02); *A61M 15/0065* (2013.01); *A61M 15/0086* (2013.01); *A61M 15/009* (2013.01); *A61M 2205/3334* (2013.01)

(58) Field of Classification Search
CPC ............ A61M 11/042; A61M 15/0003; A61M 15/0065; A61M 15/06; A61M 16/14; A61M 2016/0033; A61M 2205/121; A61M 2205/3334; A61M 2205/3368; A61M 2205/3561; A61M 2205/609; G06F 21/32
See application file for complete search history.

(56) References Cited

U.S. PATENT DOCUMENTS

| | | | |
|---|---|---|---|
| 8,689,803 | B2 | 4/2014 | Gonda |
| 8,899,230 | B2 | 12/2014 | Immel |
| 9,215,895 | B2 | 12/2015 | Bowen et al. |
| 9,901,123 | B2 | 2/2018 | Robinson et al. |
| 9,930,915 | B2 | 4/2018 | Worm et al. |
| 9,956,360 | B2 | 5/2018 | Germinario et al. |
| 10,349,675 | B2 | 7/2019 | Choukroun et al. |
| D870,959 | S | 12/2019 | Leon Duque et al. |
| 10,721,973 | B1 * | 7/2020 | Hermiz ................... A24F 40/30 |
| 10,737,041 | B1 | 8/2020 | Adelaar et al. |
| 10,772,353 | B2 | 9/2020 | Liu |
| 10,791,762 | B2 | 10/2020 | Liu |
| 10,849,364 | B2 | 12/2020 | Chen |
| 10,869,500 | B2 | 12/2020 | Chen |
| 10,893,703 | B2 | 1/2021 | Chen |
| 10,905,157 | B2 | 2/2021 | Lai |
| 10,905,167 | B2 | 2/2021 | Atkins et al. |
| D912,309 | S | 3/2021 | Bowen et al. |
| 10,952,468 | B2 | 3/2021 | Bowen et al. |
| 10,973,262 | B2 | 4/2021 | Li et al. |
| 10,986,868 | B2 | 4/2021 | Chen |
| 10,993,475 | B2 | 5/2021 | Chen |
| 11,006,672 | B2 | 5/2021 | Wei et al. |
| 11,013,271 | B2 | 5/2021 | Ding et al. |
| 11,033,694 | B2 | 6/2021 | Ballam et al. |
| 11,083,223 | B2 | 8/2021 | Chen |
| 12,114,695 | B2 * | 10/2024 | Jacobs, Jr. ............. A24F 40/60 |
| 2003/0098022 | A1 | 5/2003 | Nakao et al. |
| 2008/0138294 | A1 | 6/2008 | Gonda |
| 2014/0345631 | A1 | 11/2014 | Bowen et al. |
| 2015/0020824 | A1 | 1/2015 | Bowen et al. |
| 2016/0278435 | A1 | 9/2016 | Choukroun et al. |
| 2019/0364970 | A1 | 12/2019 | Choukroun et al. |
| 2020/0037669 | A1 | 2/2020 | Bowen |
| 2020/0146361 | A1 | 5/2020 | Silver et al. |
| 2020/0163382 | A1 | 5/2020 | Trzecieski |
| 2020/0229508 | A1 | 7/2020 | Israel et al. |
| 2020/0229512 | A1 * | 7/2020 | Israel ....................... H05B 3/46 |
| 2020/0245687 | A1 | 8/2020 | Tsuji et al. |
| 2020/0305502 | A1 | 10/2020 | Ouyang |
| 2020/0315253 | A1 | 10/2020 | Legendy et al. |
| 2020/0367572 | A1 | 11/2020 | Hejazi et al. |
| 2020/0411839 | A1 | 12/2020 | Wang et al. |
| 2021/0000174 | A1 | 1/2021 | Huang |
| 2021/0000178 | A1 | 1/2021 | Chen |
| 2021/0186082 | A1 | 6/2021 | Bowen et al. |
| 2021/0268215 | A1 * | 9/2021 | Israel ................... A61M 11/042 |
| 2021/0368863 | A1 * | 12/2021 | Sweedler ................ A24F 40/57 |
| 2021/0392953 | A1 * | 12/2021 | Tannen ..................... A24F 7/00 |
| 2022/0160031 | A1 | 5/2022 | Griffin et al. |
| 2022/0225685 | A1 * | 7/2022 | Blackmon ............... A24F 40/57 |
| 2022/0256929 | A1 | 8/2022 | Jabobs et al. |
| 2023/0033181 | A1 * | 2/2023 | Kuenzel .................. A24F 40/53 |
| 2023/0037987 | A1 | 2/2023 | Benning et al. |
| 2023/0284683 | A1 * | 9/2023 | Hazani .................. A24F 40/465 |
| 2024/0023604 | A1 * | 1/2024 | Bourbonnais ........... A24F 40/50 |
| 2024/0226092 | A1 | 7/2024 | Albert et al. |
| 2025/0127219 | A1 * | 4/2025 | Jacobs, Jr. ............ A61M 15/06 |

FOREIGN PATENT DOCUMENTS

| | | |
|---|---|---|
| CN | 110025049 | 7/2019 |
| CN | 111264908 | 6/2020 |
| WO | WO 2016/000136 | 1/2016 |
| WO | WO 2020/078801 A1 | 4/2020 |
| WO | WO 2020/252810 | 12/2020 |
| WO | WO 2020/254313 | 12/2020 |
| WO | WO 2021/003438 | 1/2021 |
| WO | WO 2021/013208 | 1/2021 |
| WO | WO 2023/120041 | 6/2023 |

OTHER PUBLICATIONS

International Search Report issued in application No. PCT/US2022/037213, dated Oct. 4, 2022.
Extended Search Report issued in corresponding European Patent Application No. 22842900.7, dated Apr. 9, 2025, in 11 pages.

* cited by examiner

700

PROVIDE A HAND-HELD DELIVERY SYSTEM HAVING AN AEROSOLIZER SYSTEM WITH THREE AEROSOLIZERS EACH INCLUDING A DIFFERENT SUBSTANCE

705

CONTROL THE AEROSOL PRODUCED BY EACH OF THE THREE AEROSOLIZERS TO FORM AN AEROSOL MIXTURE IN AN AEROSOL MIXING CHAMBER, BASED ON A TREATMENT PROGRAM BASED ON INFORMATION FROM ONE OR MORE OF SENSORS ON THE HAND-HELD DELIVERY SYSTEM

710

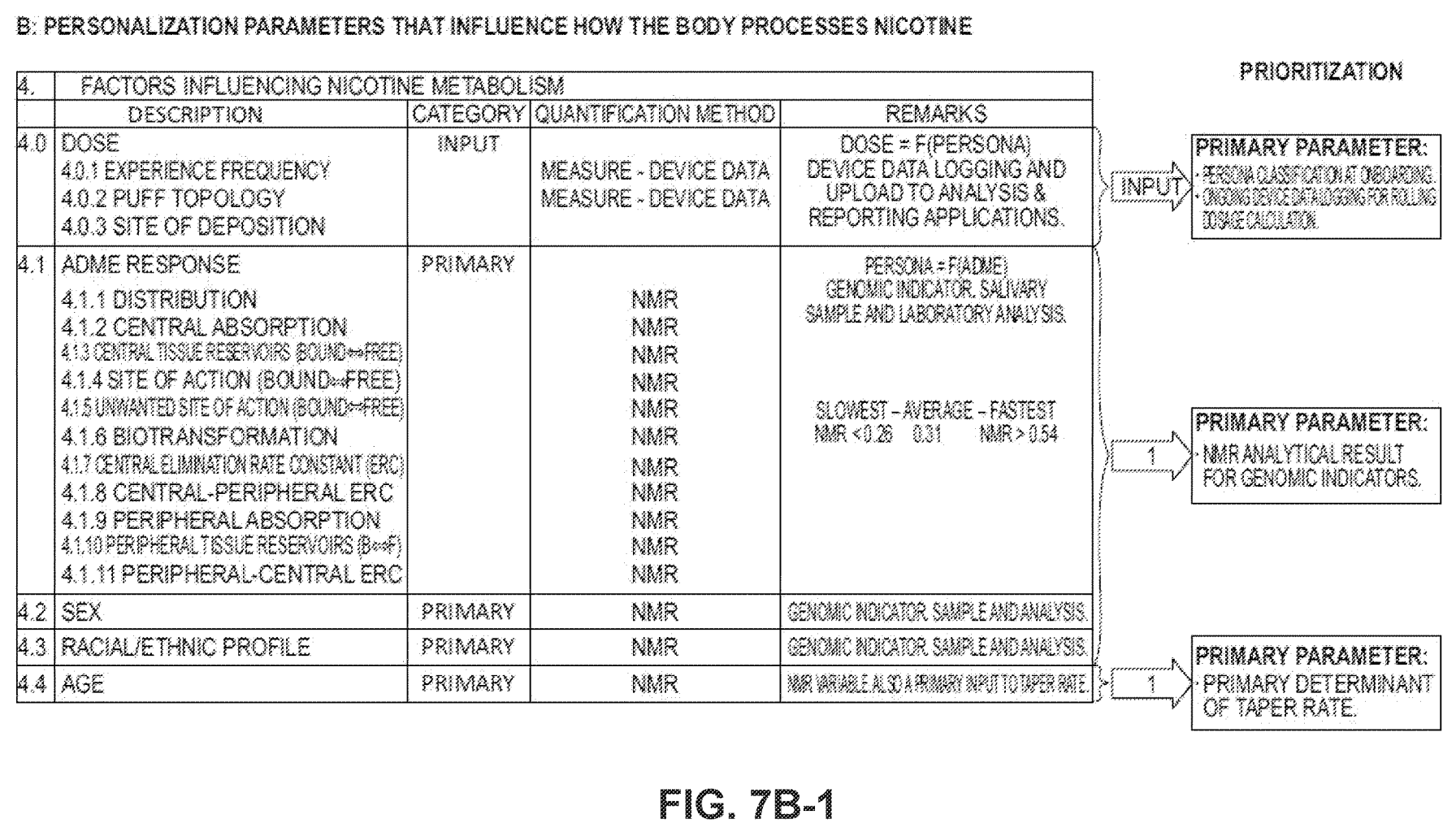

B: PERSONALIZATION PARAMETERS THAT INFLUENCE HOW THE BODY PROCESSES NICOTINE

PRIORITIZATION

PRIMARY PARAMETER: [illegible small text] DOSE CALCULATION

PRIMARY PARAMETER: NMR ANALYTICAL RESULT FOR GENOMIC INDICATORS.

PRIMARY PARAMETER: PRIMARY DETERMINANT OF TAPER RATE.

INPUT

4. FACTORS INFLUENCING NICOTINE METABOLISM

| | DESCRIPTION | CATEGORY | QUANTIFICATION METHOD | REMARKS |
|---|---|---|---|---|
| 4.0 | DOSE | INPUT | | DOSE = F(PERSONA) DEVICE DATA LOGGING AND UPLOAD TO ANALYSIS AND REPORTING APPLICATIONS. |
| | 4.0.1 EXPERIENCE FREQUENCY | | MEASURE - DEVICE DATA | |
| | 4.0.2 PUFF TOPOLOGY | | MEASURE - DEVICE DATA | |
| | 4.0.3 SITE OF DEPOSITION | | | |
| 4.1 | ADME RESPONSE | PRIMARY | | PERSONA = F(ADME) GENOMIC INDICATOR, SALIVARY SAMPLE AND LABORATORY ANALYSIS |
| | 4.1.1 DISTRIBUTION | | NMR | |
| | 4.1.2 CENTRAL ABSORPTION | | NMR | |
| | 4.1.3 CENTRAL TISSUE RESERVOIRS (BOUND→FREE) | | NMR | |
| | 4.1.4 SITE OF ACTION (BOUND→FREE) | | NMR | SLOWEST – AVERAGE – FASTEST |
| | 4.1.5 UNWANTED SITE OF ACTION (BOUND→FREE) | | NMR | NMR <0.26   0.31   NMR >0.54 |
| | 4.1.6 BIOTRANSFORMATION | | NMR | |
| | 4.1.7 CENTRAL ELIMINATION RATE CONSTANT (ERC) | | NMR | |
| | 4.1.8 CENTRAL-PERIPHERAL ERC | | NMR | |
| | 4.1.9 PERIPHERAL ABSORPTION | | NMR | |
| | 4.1.10 PERIPHERAL TISSUE RESERVOIRS (B→F) | | NMR | |
| | 4.1.11 PERIPHERAL-CENTRAL ERC | | NMR | |
| 4.2 | SEX | PRIMARY | NMR | GENOMIC INDICATOR SAMPLE AND ANALYSIS. |
| 4.3 | RACIAL/ETHNIC PROFILE | PRIMARY | NMR | GENOMIC INDICATOR SAMPLE AND ANALYSIS. |
| 4.4 | AGE | PRIMARY | NMR | NMR VARIABLE ALSO A PRIMARY INPUT TO TAPER RATE. |

FIG. 7B-1

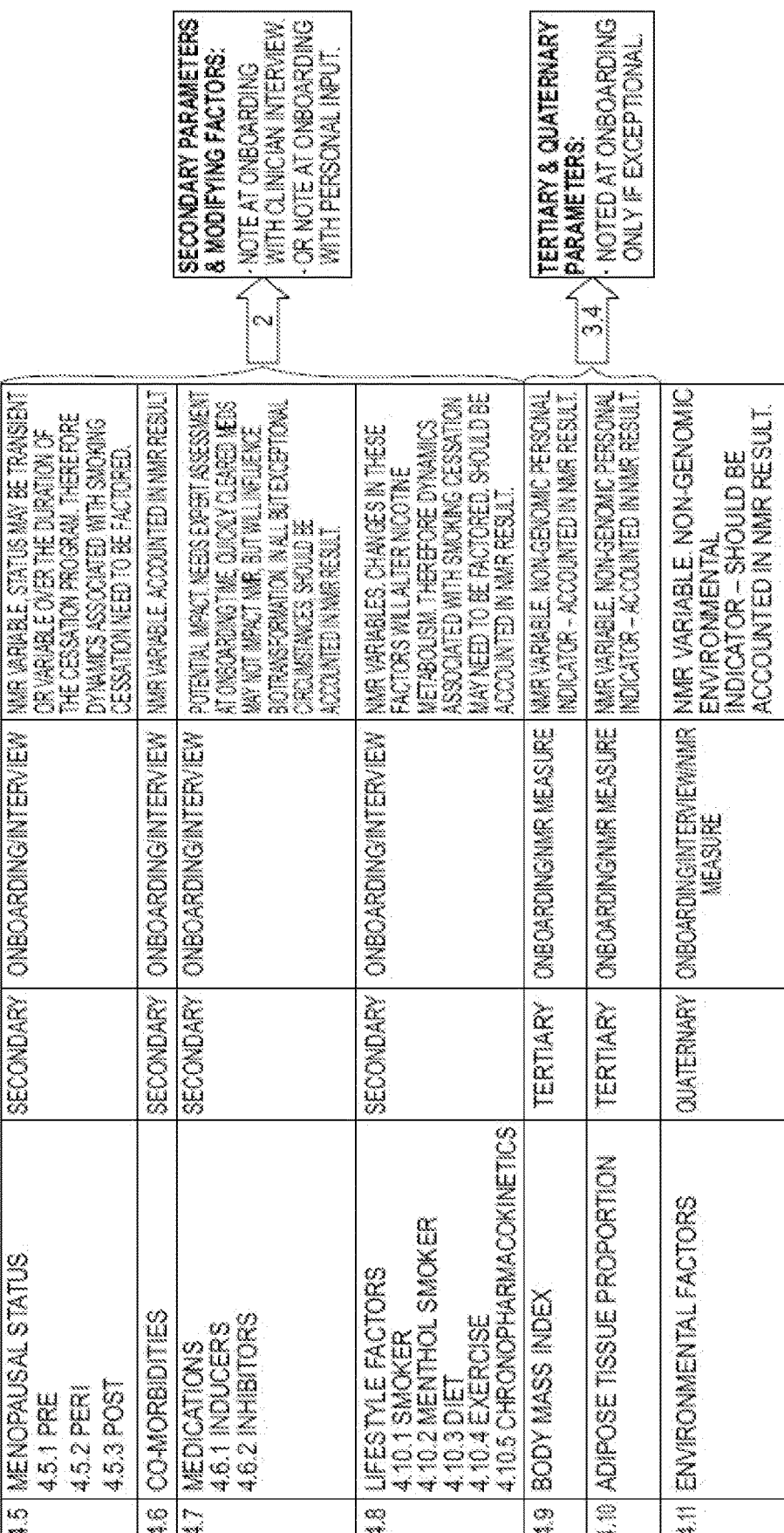

| 4.5 | MENOPAUSAL STATUS<br>4.5.1 PRE<br>4.5.2 PERI<br>4.5.3 POST | SECONDARY | ONBOARDING/INTERVIEW | NMR VARIABLE. STATUS MAY BE TRANSIENT OR VARIABLE OVER THE DURATION OF THE CESSATION PROGRAM, THEREFORE DYNAMICS ASSOCIATED WITH SMOKING CESSATION NEED TO BE FACTORED. |
| 4.6 | CO-MORBIDITIES | SECONDARY | ONBOARDING/INTERVIEW | NMR VARIABLE. ACCOUNTED IN NMR RESULT. |
| 4.7 | MEDICATIONS<br>4.6.1 INDUCERS<br>4.6.2 INHIBITORS | SECONDARY | ONBOARDING/INTERVIEW | POTENTIAL IMPACT NEEDS EXPERT ASSESSMENT AT ONBOARDING TIME. QUICKLY CLEARED MEDS MAY NOT IMPACT NMR, BUT WILL INFLUENCE BIOTRANSFORMATION. IN ALL BUT EXCEPTIONAL CIRCUMSTANCES SHOULD BE ACCOUNTED IN NMR RESULT. |
| 4.8 | LIFESTYLE FACTORS<br>4.10.1 SMOKER<br>4.10.2 MENTHOL SMOKER<br>4.10.3 DIET<br>4.10.4 EXERCISE<br>4.10.5 CHRONOPHARMACOKINETICS | SECONDARY | ONBOARDING/INTERVIEW | NMR VARIABLES. CHANGES IN THESE FACTORS WILL ALTER NICOTINE METABOLISM, THEREFORE DYNAMICS ASSOCIATED WITH SMOKING CESSATION MAY NEED TO BE FACTORED. SHOULD BE ACCOUNTED IN NMR RESULT. |
| 4.9 | BODY MASS INDEX | TERTIARY | ONBOARDING/NMR MEASURE | NMR VARIABLE. NON-GENOMIC PERSONAL INDICATOR – ACCOUNTED IN NMR RESULT. |
| 4.10 | ADIPOSE TISSUE PROPORTION | TERTIARY | ONBOARDING/NMR MEASURE | NMR VARIABLE. NON-GENOMIC PERSONAL INDICATOR – ACCOUNTED IN NMR RESULT. |
| 4.11 | ENVIRONMENTAL FACTORS | QUATERNARY | ONBOARDING/INTERVIEW/NMR MEASURE | NMR VARIABLE. NON-GENOMIC ENVIRONMENTAL INDICATOR – SHOULD BE ACCOUNTED IN NMR RESULT. |

SECONDARY PARAMETERS & MODIFYING FACTORS:
· NOTE AT ONBOARDING WITH CLINICIAN INTERVIEW - OR NOTE AT ONBOARDING WITH PERSONAL INPUT.

2

TERTIARY & QUATERNARY PARAMETERS:
· NOTED AT ONBOARDING ONLY IF EXCEPTIONAL.

C: Biological Co-Factors: Basic D-ADME² model components – inside & outside the body Nicotine deposited in the body is:

Absorbed
Distributed
Metabolized in an individual manner that is determined by genomics, personal and environmental parameters, then the metabolic by-products are:

Eliminated

Excretion from body

User-determined nicotine dose from

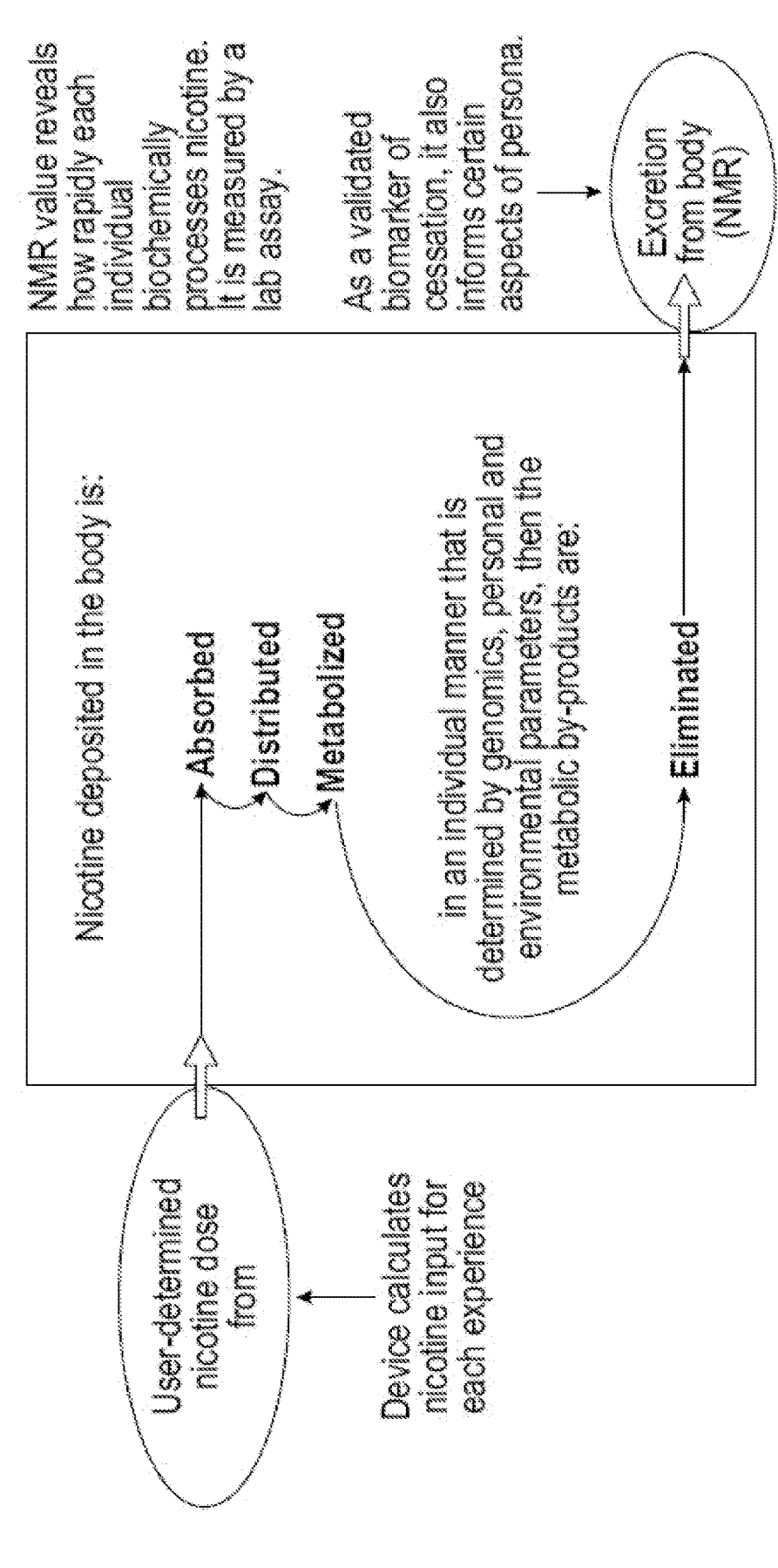

C: Biological Co-Factors: We calculate the nicotine input and measure one output biomarker – NMR* – to determine how each individual's body metabolizes nicotine.

NMR value reveals how rapidly each individual biochemically processes nicotine. It is measured by a lab assay.

As a validated biomarker of cessation, it also informs certain aspects of persona.

Nicotine deposited in the body is:

Absorbed

Distributed

Metabolized in an individual manner that is determined by genomics, personal and environmental parameters, then the metabolic by-products are:

Eliminated

Excretion from body (NMR)

User-determined nicotine dose from

Device calculates nicotine input for each experience

FIG. 7E

* NMR = Nicotine Metabolite Ratio

D: Detailed cascaded D-2ADME personalization model

FIG. 7I

D: Psychosocial Co-Factors: Result in a user being compelled to initiate a smoking experience

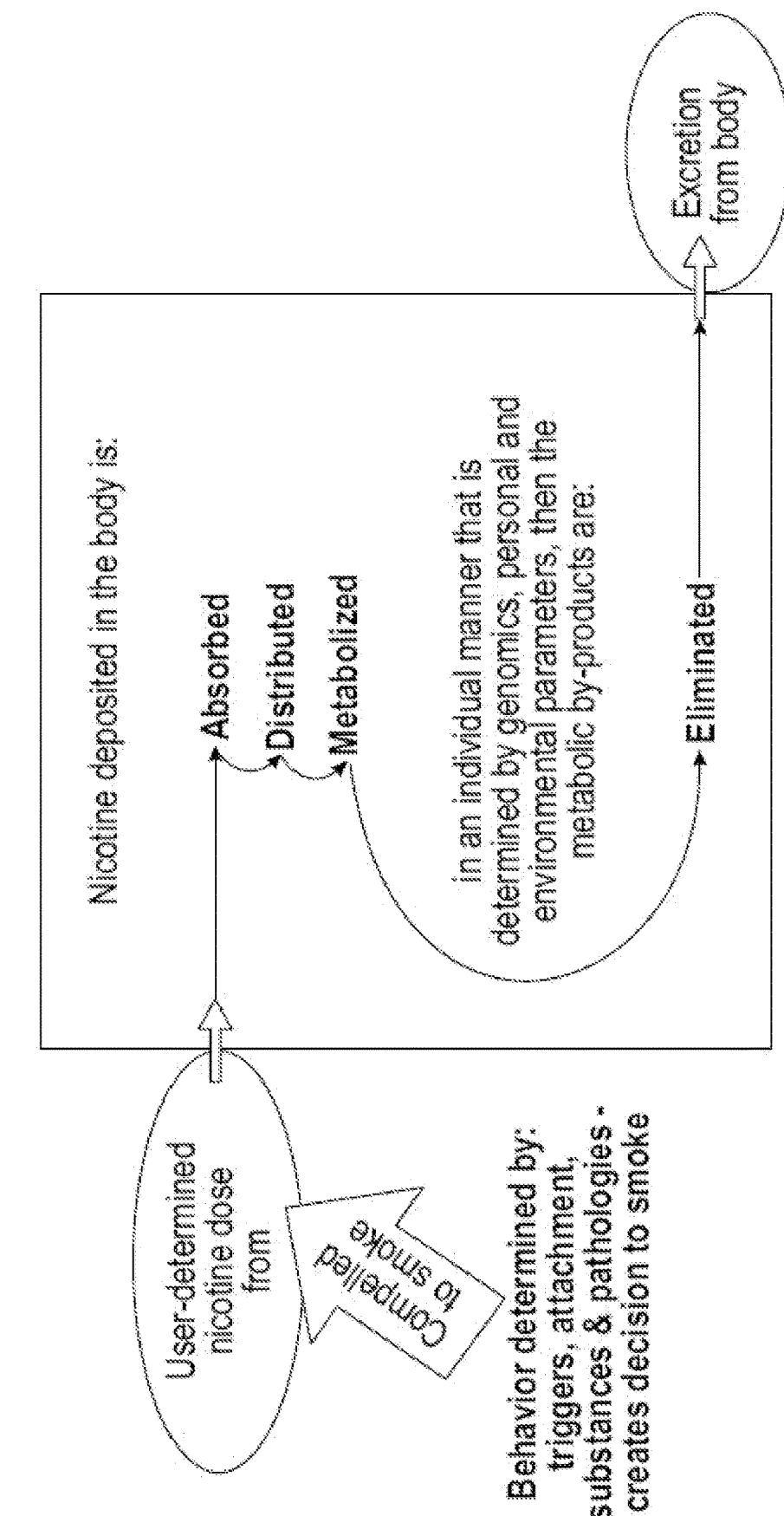

Nicotine deposited in the body is:

Absorbed
Distributed
Metabolized in an individual manner that is determined by genomics, personal and environmental parameters, then the metabolic by-products are:

Eliminated

Excretion from body

User-determined nicotine dose from

Compelled to smoke

Behavior determined by: triggers, attachment, substances & pathologies - creates decision to smoke

FIG. 7J

F: We use personalization parameters and clustered persona characteristics to map the magnitude & range of associated cessation liquid parameters Biological Persona Parameters
Reduced      Typical      Enhanced Psychosocial Persona Parameters
Intense
Typical
Mild F: ρ - Concentration levels of nicotine mapped to persona profile and metabolism rate

| | Reduced | Typical | Enhanced |
|---|---|---|---|
| Intense | Moderate Concentration | High Concentration | High Concentration |
| Typical | Low Concentration | Moderate Concentration | High Concentration |
| Mild | Low Concentration | Low Concentration | Moderate Concentration |

Psychosocial Persona Parameters

Biological Persona Parameters

FIG. 7L

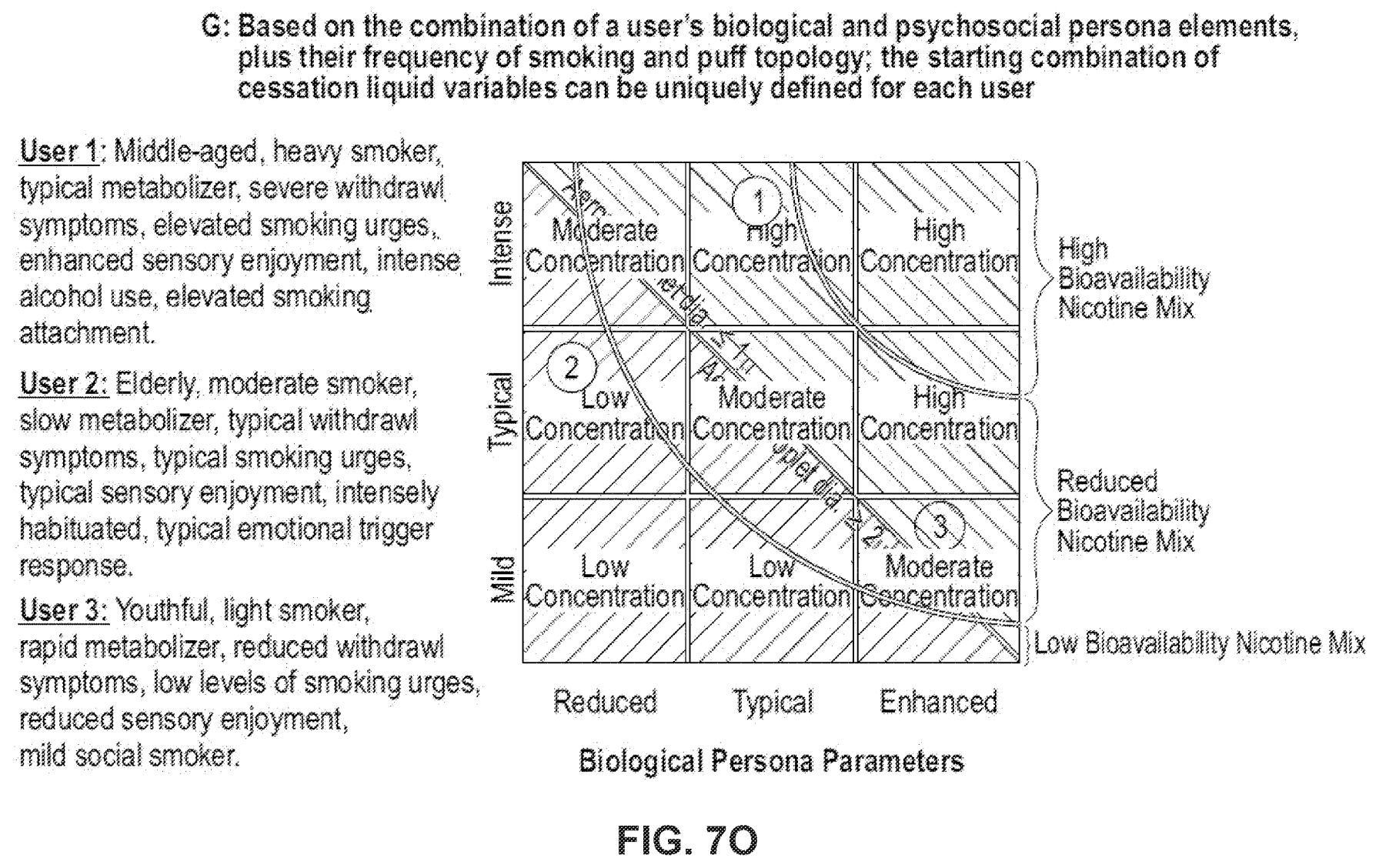

G: Based on the combination of a user's biological and psychosocial persona elements, plus their frequency of smoking and puff topology; the starting combination of cessation liquid variables can be uniquely defined for each user User 1: Middle-aged, heavy smoker, typical metabolizer, severe withdrawl symptoms, elevated smoking urges, enhanced sensory enjoyment, intense alcohol use, elevated smoking attachment.

User 2: Elderly, moderate smoker, slow metabolizer, typical withdrawl symptoms, typical smoking urges, typical sensory enjoyment, intensely habituated, typical emotional trigger response.

User 3: Youthful, light smoker, rapid metabolizer, reduced withdrawl symptoms, low levels of smoking urges, reduced sensory enjoyment, mild social smoker.

FIG. 70

G: Based on the cessation start point, age, and behavioral information related to triggers, stresses, anxiety, depression, alcohol consumption and social cue responses, a taper path, taper rate, and program duration is uniquely determined

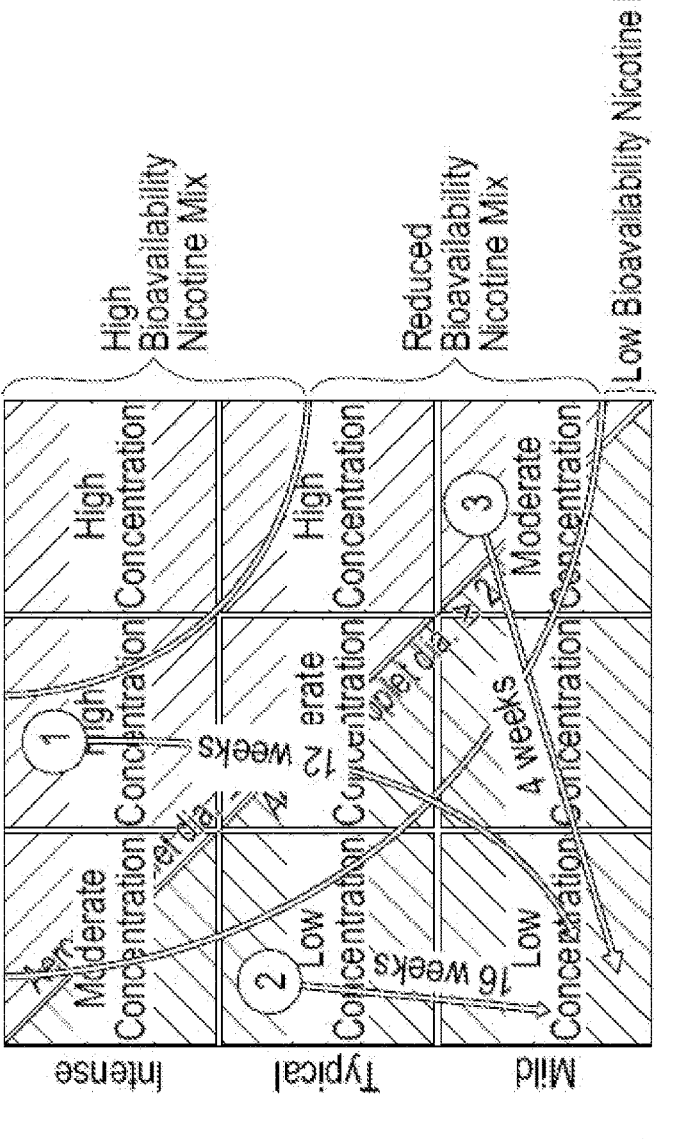

User 1: Taper from high dose, high bioavailability, pulmonary deposition, to very low dose, low bioavailability, buccal deposition over 12 weeks. User changes consumable category three times.

User 2: Taper from low dose, low bioavailability, buccal deposition, to very low dose over 16 weeks. Consumable category remains the same over the 16 week quit period.

User 3: Taper from moderate dose, reduced bioavailability, pulmonary deposition to very low dose, low bioavailability, buccal deposition over 4 weeks. User has two consumable category changes over four weeks.

IMPLEMENT A TREATMENT PROGRAM ON A HANDHELD DELIVERY SYSTEM HAVING A PLURALITY OF MECHANICAL AEROSOLIZERS

992

CONTROL THE PLURALITY OF MECHANICAL AEROSOLIZERS TO GENERATE AN AEROSOL MIXTURE ACCORDING TO THE TREATMENT PROGRAM AND BASED ON ONE OR MORE SENSORS OF THE DELIVERY SYSTEM

DRUG DELIVERY SYSTEMS, DEVICES, AND METHODS

INCORPORATION BY REFERENCE TO ANY PRIORITY APPLICATIONS

This application is a continuation-in-part of U.S. application Ser. No. 17/650,783, filed Feb. 11, 2022. This application claims the benefit of U.S. Provisional Application Nos. 63/263,863, filed Nov. 10, 2021, 63/261,638, filed Sep. 24, 2021, and 63/203,324, filed Jul. 16, 2021. Each of the above-listed applications is incorporated by reference herein in its entirety. All applications for which a foreign or domestic priority claim is identified in the Application Data Sheet as filed with the present application are hereby incorporated by reference under 37 CFR 1.57.

BACKGROUND

Field of the Invention

This disclosure relates to systems, devices, and methods for delivering a substance, or a combination of substances, for a medical or therapeutic purpose in accordance with a treatment program. More particularly, this invention relates to systems, devices, and methods for delivering substances in a monitored and controlled treatment program, that is individually tailored for a user and can be dynamically changed based on day-to-day sensed characteristics of the user's actions and progress in the treatment program.

Description of the Related Art

One or more medicants are often provided to a user for a medical or therapeutic purpose. Drugs are typically administered by a user through the user's mouth (e.g., as pills, chewables, and lozenges, etc.), skin (e.g., via gel, cream, spray, and a patch) or through the user's nose (e.g., via an inhaler). In all of these administration programs, the user is often responsible to properly follow a drug administrative program and track their compliance with the program to ensure the treatment is effective and safe, and thus the proper administration of drugs using such methods can be highly unreliable. Although for some treatments strict adherence to the program may not be needed, for other programs adherence is absolutely necessary for effective and safe treatment.

Patients with certain additions can be helped through certain treatment programs. Addictions can cause physical and mental harm. As an example, smoking causes many diseases including cancer, heart disease, stroke, lung diseases, diabetes, emphysema and chronic bronchitis. Smoking is also known to increase a person's risk for tuberculosis, certain eye diseases, and problems of the immune system, including rheumatoid arthritis. smoking is one of the most prevalent sources a preventable death worldwide. People who don't smoke but are near a person who is smoking may also be afflicted with one of these diseases through secondary smoke. Smoking and vaping (which is, for ease of reference, are both generally referred to herein as "smoking" unless context or specific language indicates otherwise) are highly addictive, which makes quitting smoking difficult. Many aids have been developed to quit smoking. For example, nicotine patches and nicotine gum may help a person to quit smoking. Certain devices (e.g., electronic cigarettes) have been developed as an aid to quit smoking, or at least somewhat lower health risks, by providing a less harmful source of inhaled nicotine.

Current devices that are used in programs for quitting smoking, addressing other addictions, and other treatment programs are generally used in a similar manner for everyone, even though different people have different biological factors and psychological factors (e.g., related to smoking). For example, aerosol producing devices typically cannot dynamically provide tailored aerosol mixtures based as required by a sophisticated individual treatment program. In addition, such devices cannot adequately monitor the use of the device and provide feedback to the system controlling the treatment program to ensure medicants are accurately provided and their use is tracked. Furthermore, in treatment programs for smoking and other addictions, such devices do not allow a user to address an overwhelming addiction urge, where it is automatically monitored and dynamically changes the treatment the treatment program. Accordingly, there is a need for an improved process for administering drugs in controlled, trackable treatment programs, e.g., to help a user quit smoking, or stop another addiction.

SUMMARY

The systems, methods, and devices described herein each have several aspects, no single one of which is solely responsible for its desirable attributes. Without limiting the scope of this disclosure, several non-limiting features will now be discussed briefly. The methods and techniques described herein relate to systems, devices, and methods for controlled delivery of a drug, medicant, or an active pharmaceutical ingredient (API) to a user as part of a treatment program. In some specific examples, methods and techniques described herein relate to systems, devices, and methods for a controlled delivery of an aerosol mixture to a user during a treatment program.

In one innovation, a delivery system for providing an aerosol mixture in a treatment program for quitting smoking, comprise, a delivery device including a housing; a channel in the housing, the channel structured to receive air from an opening in the housing and communicate air to an aerosolizer pod coupled to the delivery device; a flow sensor positioned to sense air flowing through the channel; a first, second, and third aerosolizer driver each having an electrical connection configured to electrically couple to a first, second, and third aerosolizer, respectively, of an aerosolizer pod coupled to the delivery device; a rescue button configured to, when actuated by a user, provide a signal to provide an additional dose of the aerosol mixture according to the treatment program; a power source; and a controller circuit coupled to the power source, the controller circuit comprising a hardware controller electrically coupled to the first, second, and third aerosolizer drivers, the flow sensor, and the rescue button, the hardware controller including a hardware processor and a non-transitory computer readable medium in communication with the hardware controller, the computer readable medium configured to store treatment program information, and to store executable instructions that, when executed, configure the hardware controller to individually control the three aerosolizer drivers to provide aerosol generation signals to the first, second and third aerosolizers, respectively, of a pod coupled to the delivery device, to generate an aerosol mixture based at least in part on the stored treatment program and information that is received from the flow sensor and the rescue button.

Various implementations can include one or more additional aspects. In some implementations, the housing comprises an aperture to receive an aerosolizer pod therein, the housing configured to at least partially surround the aerosolizer pod when the aerosolizer pod in positioned in the aperture and coupled to the delivery device. In some implementations, the housing comprises a distal end and a proximal end, and wherein the aperture to receive the aerosolizer pod is on the proximal end of the housing. In some implementations, further comprising the aerosolizer pod, wherein the aerosolizer pod is structured to be removably coupleable to the delivery device. In some implementations, the aerosolizer pod further comprises an ID chip, and wherein the delivery device further comprises an aerosolizer pod interface configured to sense the ID chip and communicate the ID chip to the hardware controller to identify the aerosolizer pod and the substances contained therein. In some implementations, the aerosolizer pod comprises an aerosolizer system including the first, second, and third aerosolizers. In some implementations, each of the first, second, and third aerosolizers includes an electrical connection configured to electrically couple to one of the first aerosolizer, second aerosolizer, and third aerosolizer drivers of the delivery device. In some implementations, wherein the first, second, and third aerosolizers are thermal aerosolizers. In some implementations, the first, second, and third aerosolizers are mechanical aerosolizers. In some implementations, the aerosolizer pod includes a first container holding a first substance, a second container holding a second substance, and a third container holding a third substance, the first, second and third containers structured to provide the first, second and third substances to the first, second, and third aerosolizers, respectively. In some implementations, the first substance comprises freebase nicotine, the second substance comprises monoprotonated nicotine, and the third substance is a flavorant.

In some implementations, the system further comprises the aerosolizer pod, the aerosolizer pod structured to be removably coupleable to the delivery device, the aerosolizer pod comprising: a distal end and a proximal end; an intake port on the distal end for receiving air flowing through the channel; a mixing chamber; an exhaust port on the proximal end for communicating the aerosol mixture from the mixing chamber out of the aerosolizer pod; an aerosolizer system comprising the first, second, and third aerosolizer, the first, second, and third aerosolizers each having an electrical connection that electrically couples to the first, second, and third aerosolizer drivers, respectively, when the aerosolizer pod is coupled to the delivery device. In some implementations, the mixing chamber includes intake openings in fluid communication with the first, second and third aerosolizer and an exhaust opening in fluid communication with the exhaust port such that aerosol generated by the first, second and third aerosolizer can enter the mixing chamber via the intake openings, mix together, and be communicated out of the pod via the pod exhaust port. In some implementations, the first aerosolizer includes a first container for holding a first substance, a first thermal aerosolizer configured to generate aerosol from the first substance based on signals received from the first aerosolizer driver, and a first passage in fluid communication with the thermal aerosolizer and the mixing chamber for communicating aerosol generated by the first thermal aerosolizer to the mixing chamber; the second aerosolizer includes a second container for holding a second substance, a second thermal aerosolizer configured to generate aerosol from the second substance based on signals received from the second aerosolizer driver, and a second passage in fluid communication with thermal aerosolizer and the mixing chamber for communicating aerosol generated by the second thermal aerosolizer to the mixing chamber; and the third aerosolizer includes a third container for holding a third substance, a third thermal aerosolizer configured to generate aerosol from the third substance based on signals received from the third aerosolizer driver, and a third passage in fluid communication with the third thermal aerosolizer and the mixing chamber for communicating aerosol generated by the third thermal aerosolizer to the mixing chamber. In some implementations, the first substance comprises a nicotine-based substance therein, and the second substance comprises a nicotine-based substance therein. In some implementations, the third substance comprises a flavorant. In some implementations, the controller circuit further comprises a transceiver, wherein the controller circuit is configured to receive treatment program information using the transceiver, and wherein the controller circuit is configured to provide signals to generate an aerosol mixture that includes a portion of a first substance, a second substance, and a third substance contained in the aerosolizer pod, based on the received treatment program information. In some implementations, the controller circuit is further configured to provide signals to generate an aerosol mixture having a certain aerosol droplet size, from each of the first, second, and third aerosolizers based on the received treatment program information.

In some implementations, the controller circuit is further configured to provide signals to generate an aerosol mixture having droplets of less than or equal to a first diameter from each of the first, second, and third aerosolizers for a first portion of the treatment program, and to provide signals to generate an aerosol mixture having droplets of greater than or equal to a second diameter for a second portion of the treatment program, based on the received treatment program information. In some implementations, the controller circuit is further configured to provide signals to generate an aerosol mixture having a majority of droplets of less than or equal to a first diameter from each of the first, second, and third aerosolizers for a first portion of the treatment program, and to provide signals to generate an aerosol mixture having a majority of droplets of greater than or equal to a second diameter for a second portion of the treatment program, based on the received treatment program information. In some implementations, the second portion of the treatment program is subsequent to the first portion of the treatment program, and wherein the first diameter is smaller than the second diameter. In some implementations, the first diameter is less than or equal to 1 µm, and the second diameter is greater than or equal to 10 µm. In some implementations, the system further comprises a button in electrical communication with the controller circuit, the controller circuit configured to activate the delivery device to provide an aerosol mixture when the button is actuated. In some implementations, the button comprises a fingerprint sensor, and wherein the controller circuit is configured to activate the delivery device to provide an aerosol mixture if fingerprint information sensed by the fingerprint sensor matches the fingerprint sensor of a specific user.

Another innovation includes a system, comprising a delivery device including a housing; a channel in the housing, the channel structured to receive air from an opening in the housing and communicate air to an aerosolizer pod coupled to the delivery device; a flow sensor positioned to sense air flowing through the channel; a first, second, and third aerosolizer driver each having an electrical connection configured to electrically couple to a first, second, and third aerosolizer, respectively, of an aerosolizer pod coupled to the delivery device; and a controller circuit coupled to a power source, the controller circuit comprising a transceiver and a hardware controller electrically coupled to the first, second, and third aerosolizer drivers, and the flow sensor, the controller circuit configured to individually control the first, second, and third aerosolizer drivers to provide aerosol generation signals to a first, second and third aerosolizer to generate an aerosol mixture based at least in part on a treatment program received using the transceiver; and a user computing device comprising an application in communication with the delivery system via the transceiver. In some implementations, the system further comprises a server system configured with a hardware processor and non-transitory computer readable storage media encoded with a treatment program including instructions executable by an operating system to control the generation of the aerosol mixtures over time according to the treatment program, and provide treatment program information to the delivery system to control the generation of the aerosol mixture by the delivery system. In some implementations, the treatment program information provided to the delivery system includes information to individually control the first, second, and third aerosolizer drivers to provide signals to a first, second and third aerosolizer coupled to the first, second and third aerosolizer drivers, respectively, to generate a desired aerosol mixture of a first aerosol generated from a first substance, a second aerosol generated by a second substance, and a third aerosol generated by a third substance. In some implementations, the treatment program information provided to the delivery system includes information to individually control the first, second, and third aerosolizer drivers to provide signals to a first, second and third aerosolizer coupled to the first, second and third aerosolizer drivers to generate the first, second and third aerosol having an aerosol droplet of a certain diameter. In some implementations, the treatment program information provided to the delivery system includes information to individually control the first, second, and third aerosolizer drivers to provide signals to a first, second and third aerosolizer coupled to the first, second and third aerosolizer drivers to generate the first, second and third aerosol having an aerosol droplet of a first diameter for a first portion of time and an aerosol droplet of a second diameter for a second portion of time.

Another innovation includes a method for smoking cessation, the method comprising providing a delivery system including a delivery device including a housing; a channel in the housing, the channel structured to receive air from an opening in the housing and communicate air to an aerosolizer pod coupled to the delivery device; a flow sensor positioned to sense air flowing through the channel; a first, second, and third aerosolizer driver configured to electrically couple to a first, second, and third aerosolizer, respectively, of an aerosolizer pod coupled to the delivery device; a rescue button configured to, when actuated by a user, provide a signal indicative of the user's need for an additional dose of an aerosol mixture; a power source; and a controller circuit coupled to the power source, the controller circuit comprising a hardware controller electrically coupled to the first, second, and third aerosolizer drivers, the flow sensor, and the rescue button, the hardware controller including a hardware processor and a non-transitory computer readable medium in communication with the hardware controller, the computer readable medium configured to store treatment program information, and to store executable instructions that, when executed, configure the hardware controller to individually control the three aerosolizer drivers to provide aerosol generation signals to first, second and third aerosolizers, respectively, of a pod coupled to the delivery device to generate an aerosol mixture based at least in part on the stored treatment program for quitting smoking, and information that is received from the flow sensor and the rescue button; and an aerosolizer pod, the aerosolizer pod comprising an aerosolizer system including the first, second, and third aerosolizers, wherein the pod is structured to be removably coupleable to the delivery device, each of the first, second, and third aerosolizers having an electrical connection that electrically couples to one of the first aerosolizer, second aerosolizer, and third aerosolizer drivers of the delivery device; a first container holding a first substance, a second container holding a second substance, and a third container holding a third substance, the first, second and third containers structured to provide the first, second and third substances to the first, second, and third aerosolizers, respectively, wherein the first substance is freebase nicotine and the second substance is monoprotonated nicotine; and generating aerosol mixtures in accordance with a smoking cessation treatment program to generate aerosol mixtures that are dynamically changed over a period of time to have different aerosol drop sizes and different concentrations of the first, second and third substances based at least in part on received signals from the flow sensor and the rescue button, and on smoking cessation treatment program information stored in the non-transitory computer readable medium.

Another innovation includes a method for smoking cessation, the method comprising providing signals, from a hardware controller in a hand-held delivery device, to a first, second and third aerosolizer driver in the delivery device to dynamically control a first, second and third aerosolizer in a pod coupled to the delivery device, to generate aerosol mixtures that are dynamically changed over a period of time to have different aerosol droplet sizes and different concentration of a first, second and third substance in containers of the pod based at least in part on received input signals from one or more of a flow sensor, a rescue button, and on smoking cessation treatment program information stored in a non-transitory computer readable medium coupled to the hardware controller, wherein the method is executed by the controller executing computer executable instructions stored on the non-transitory computer readable medium, wherein the executable instructions when executed cause the hardware controller to providing signal to the first, second, and third aerosolizer drivers according to the smoking cessation program.

Another innovation includes a delivery system for providing an aerosol mixture in a treatment program for quitting smoking, comprising a pod comprising an aerosolizer system including a first, second, and third aerosolizers, and a first, second and third container in communication with the first, second, and third aerosolizer, respectively, each container holding a substance that is used to generate an aerosol mixture according to the treatment program, a delivery device, wherein the pod is removably coupleable to the delivery device, the delivery device including a housing; a channel structured to receive air from an opening in the housing and communicate air to an aerosolizer pod coupled to the delivery device; a flow sensor positioned to sense air flowing through the channel; a first, second, and third aerosolizer driver configured to electrically couple to the first, second, and third aerosolizer, respectively, of the pod when the pod is coupled to the delivery device; a rescue button configured to, when actuated by a user, provide a signal indicative of the user's need for an additional dose of an aerosol mixture; a power source; and a controller circuit coupled to the power source, the controller circuit comprising a hardware controller electrically coupled to the first, second, and third aerosolizer drivers, the flow sensor, and the rescue button, the hardware controller including a hardware processor and a non-transitory computer readable medium in communication with the hardware controller, the computer readable medium configured to store treatment program information, and to store executable instructions that, when executed, configure the hardware controller to individually control the three aerosolizer drivers to provide aerosol generation signals to the first, second and third aerosolizers, respectively, to generate an aerosol mixture based at least in part on the stored treatment program, and information that is received from the flow sensor and the rescue button. In some implementations, the three aerosolizers are thermal aerosolizers. In some implementations, the three aerosolizers are mechanical aerosolizers. In some implementations, the first container contains freebase nicotine, and the second container contains monoprotonated nicotine.

Another innovation includes a computer-implemented method for providing a treatment program for smoking cessation, the method comprising generating a smoking cessation treatment program that includes a plurality of treatment periods based on received patient information, the patient information including a nicotine metabolic rate;

communicating aerosol mixture information, based on the treatment program, to a handheld delivery system that includes three substances which are used to generate an aerosol mixture that is provided to the patient, the aerosol mixture information indicating, for each of the plurality of treatment periods, an amount of each of the three substances to be included in the aerosol mixture and the droplet size of the aerosol droplets in the aerosol mixture, wherein the method is performed by one or more computer hardware processors executing a plurality of computer readable instructions stored on a non-transitory computer memory. In some implementations, the method further includes generating, on the delivery system, the aerosol mixture based on the aerosol mixture information. In some implementations, the method further includes receiving usage information from the delivery system, and communicating to the delivery system updated aerosol mixture information, based at least in part on the usage information.

Another innovation is a method of operating a smoking or vaping cessation system, the method comprising providing a smoking cessation system (for example, in any of the embodiments and having features described herein) and controlling aerosol produced by each of the three aerosolizers to form an aerosol mixture in an aerosol mixing chamber, based on the cessation program, and based on information received from one or more sensors.

Another innovation includes a method of operating a handheld smoking or vaping cessation system, the method comprising controlling aerosol generated by each of the three or more aerosolizers of an aerosolizer system to form an aerosol mixture in an aerosol mixing chamber, the aerosol mixing chamber being in fluid communication with an exhaust opening for providing the aerosol mixture to a user.

Another innovation is a non-transitory computer readable medium having instructions stored thereon, that when executed by a computer hardware processor cause the computer hardware processor to perform a portion of, or all of, any of the methods described herein.

In an example, an innovation includes a non-transitory computer readable medium for operating a smoking cessation system, the computer readable medium having program instructions for causing a hardware processor to perform a method of providing signals, from a hardware controller in a hand-held cessation device, to a first, second and third aerosolizer driver in the hand-held cessation device to dynamically and individually control a first, second and third aerosolizer, in an aerosolizer pod coupled to the hand-held cessation device, to generate aerosol mixtures that are dynamically changed over a period of time. In another example, an innovation includes a non-transitory computer readable medium for operating a smoking cessation system, the computer readable medium having program instructions for causing a hardware processor to perform a method of providing signals, from a hardware controller in a hand-held cessation device, to a first, second and third aerosolizer driver in the hand-held cessation device to dynamically and individually control a first, second and third aerosolizer, in an aerosolizer pod coupled to the hand-held cessation device, to generate aerosol mixtures that are dynamically changed over a period of time, including controlling the aerosol mixture having to have one or more of different drop sizes and different concentration of a first, second and third substance contained in the first, second, and third aerosolizer, respectively, based at least in part the cessation program, and which can also be based on received input signals from one or more sensors, and on a smoking cessation program information stored in the non-transitory computer readable medium coupled to the hardware controller.

Additional embodiments of the disclosure are described below in reference to the appended claims, which may serve as an additional summary of the disclosure.

In various embodiments, systems disclosed that a computer readable storage medium having program instructions embodied therewith, and one or more processors configured to execute the program instructions to cause the one or more processors to perform operations comprising one or more aspects of the above- and/or below-described embodiments (including one or more aspects of the appended claims). The cessation program can be included on server system, or can be included on an application-specific integrated circuit (ASIC) or other integrated circuit chips that are customized to include data flow processing and classifying, and such ASIC's or other integrated circuit chips can be included in a network or network element.

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a non-transitory computer readable storage medium are disclosed, wherein the computer readable storage medium has program instructions embodied therewith, the program instructions executable by one or more processors to cause the one or more processors to perform operations comprising one or more aspects of the above-described and/or below-described embodiments (including one or more aspects of the appended claims).

BRIEF DESCRIPTION OF THE DRAWINGS

The features and advantages of the systems and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings are not intended to depict every feature, structure, and/or component of actual embodiments of the systems and components illustrated, are they intended to depict relative dimensions of the illustrated elements, and the drawings may not be drawn to scale.

FIGS. 7B-1 and 7B-2 is a table illustrating personalization parameters that influence how the body processes nicotine.

FIG. 7E is a diagram illustrating an example of how nicotine input and output are measured, according to one embodiment.

FIG. 7I is a diagram illustrating the personalized parameters and device managed variables used in the smoking cessation system.

FIG. 7J is a diagram illustrating the psychosocial co-factors when a user is being compelled to initiate a smoking experience.

FIG. 7L is a diagram illustrating concentration levels of nicotine mapped to persona profile and metabolism rate.

FIG. 7O is a diagram illustrating a starting combination of cessation liquid variables defined for a unique user.

FIG. 7P is a diagram illustrating variables that can be applied to uniquely tailor a cessation program.

8F illustrates examples of user interfaces thar are displayed on the user device during the treatment program, according to some embodiments.

Figure 9A:
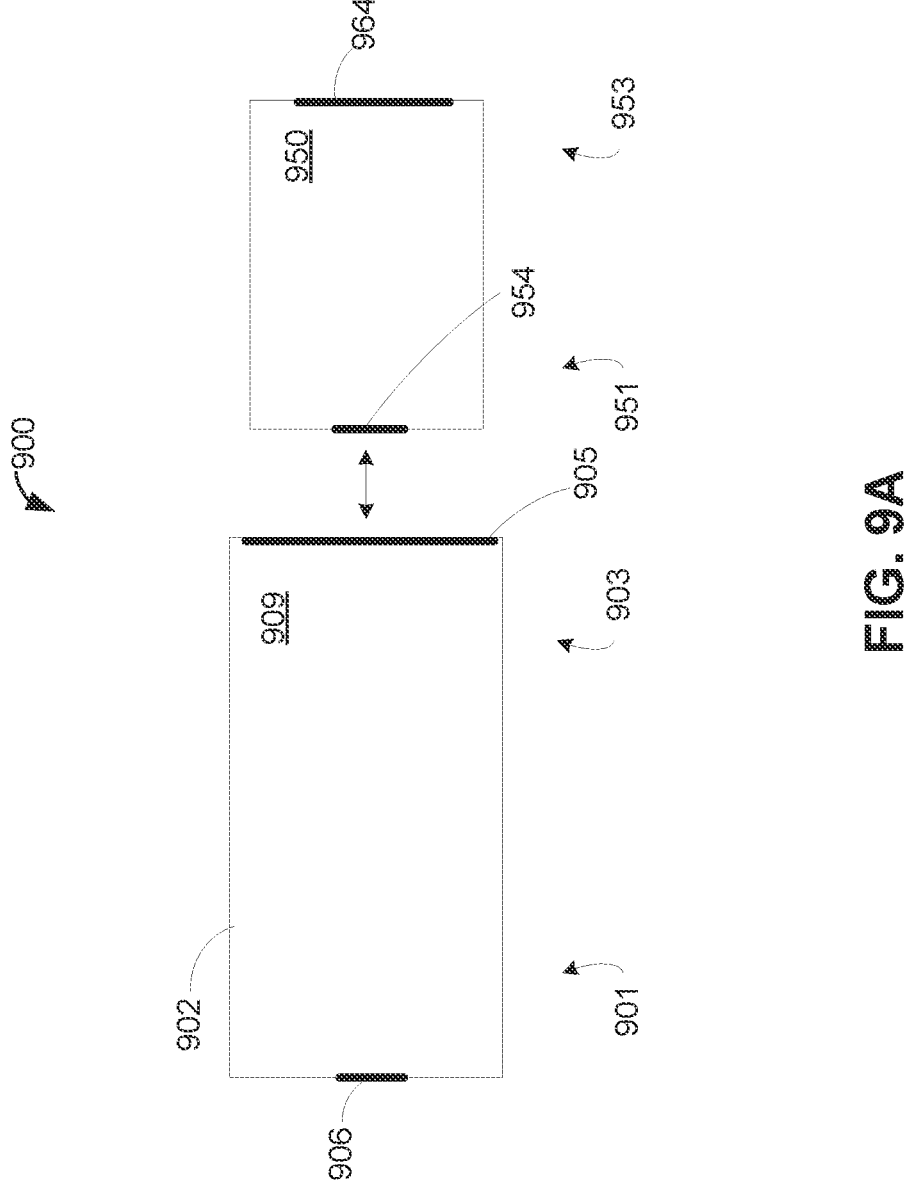

FIG. 9A illustrates an example of a delivery device with the pod capable of being coupled to the delivery device.

Figure 9B:
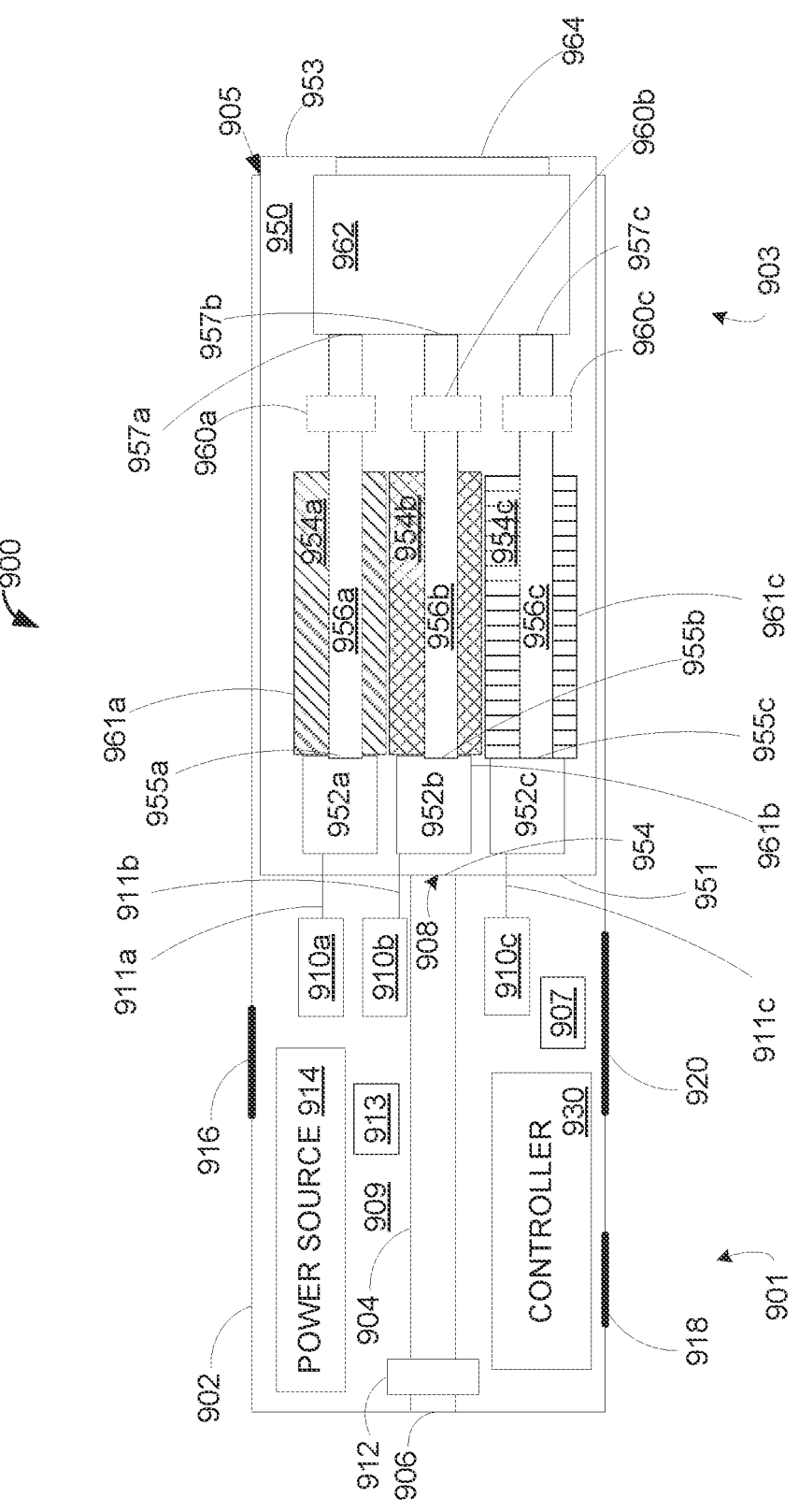

FIG. 9B illustrates the delivery device coupled to pod shown in FIG. 9A.

Figure 9C:
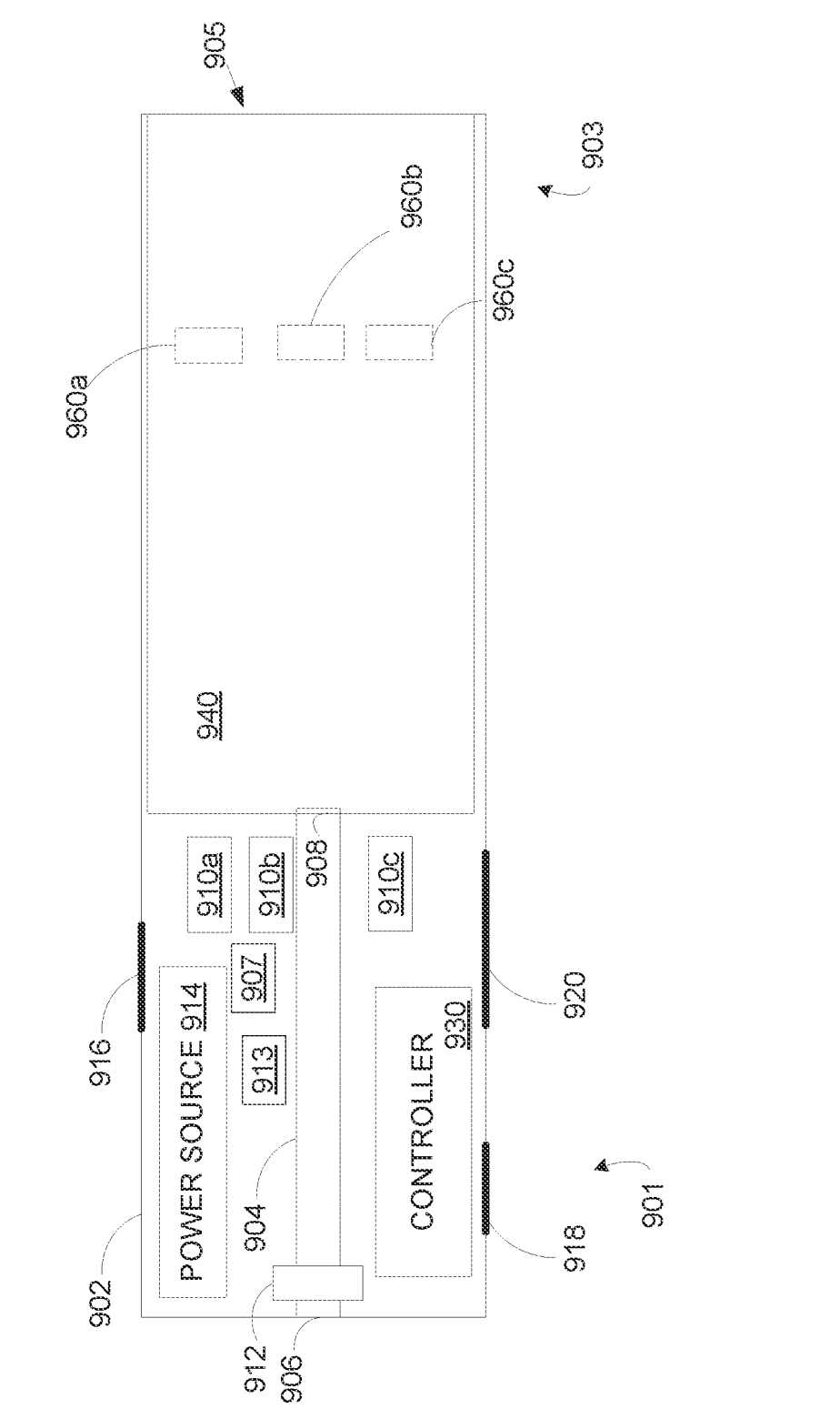

FIG. 9C further illustrates the device without the pod that is show in FIG. 9B

Figure 9D:
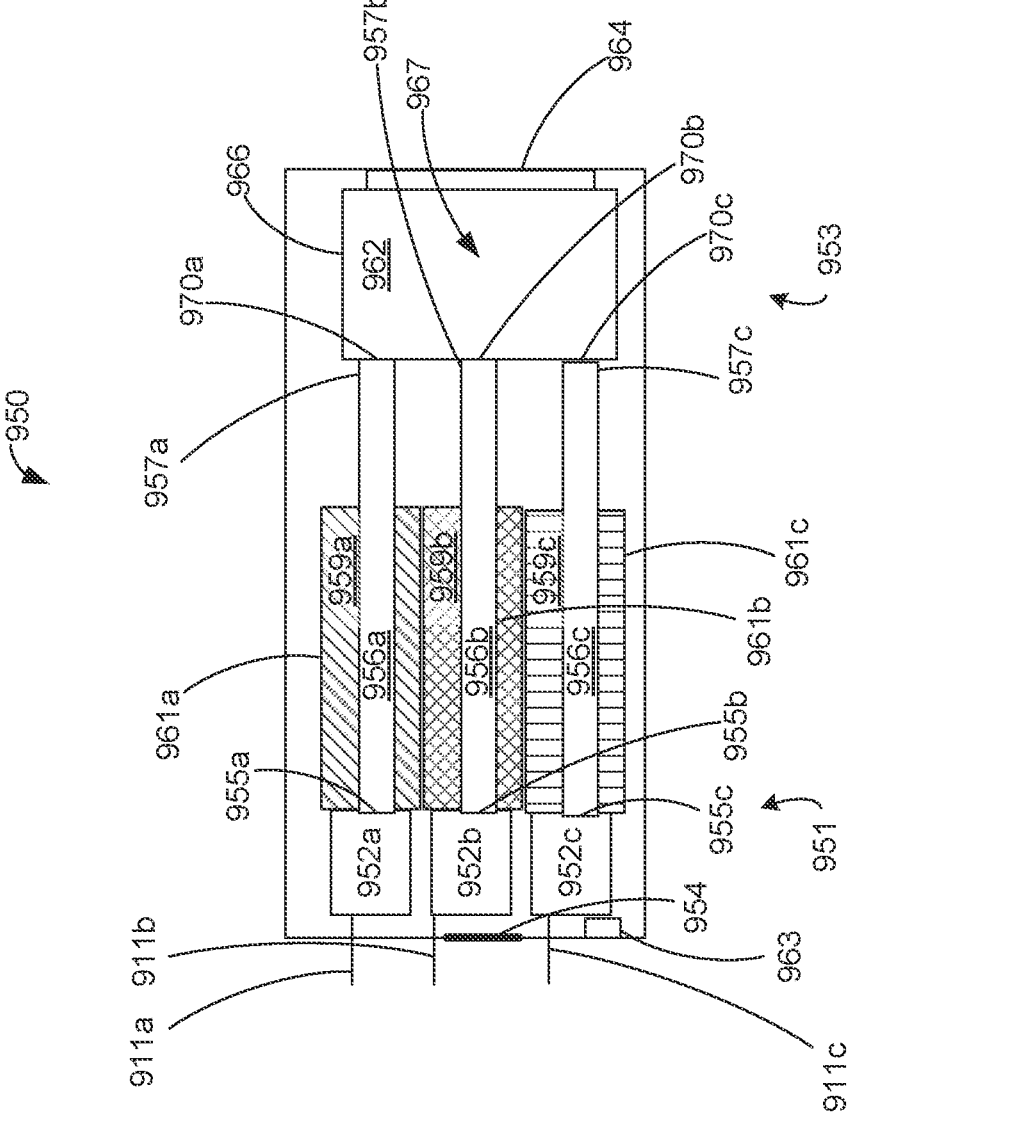

FIG. 9D illustrates a pod that utilizes non-thermal aerosolizers for a drug delivery device.

Figure 3A:
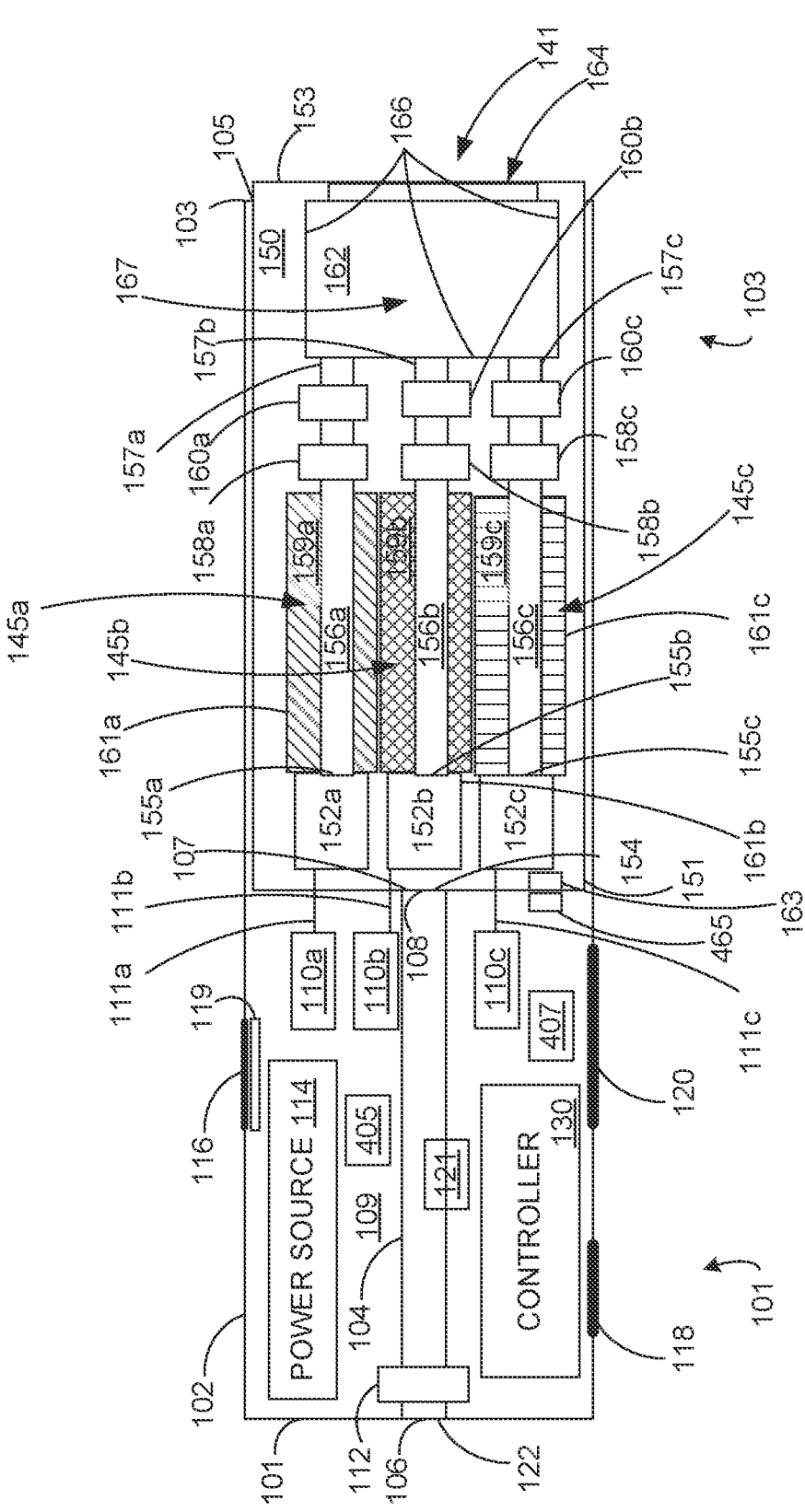
FIG. 3A is a schematic of an example of a cessation system, illustrating the aerosolizer system coupled to the housing.
Figure 9E:
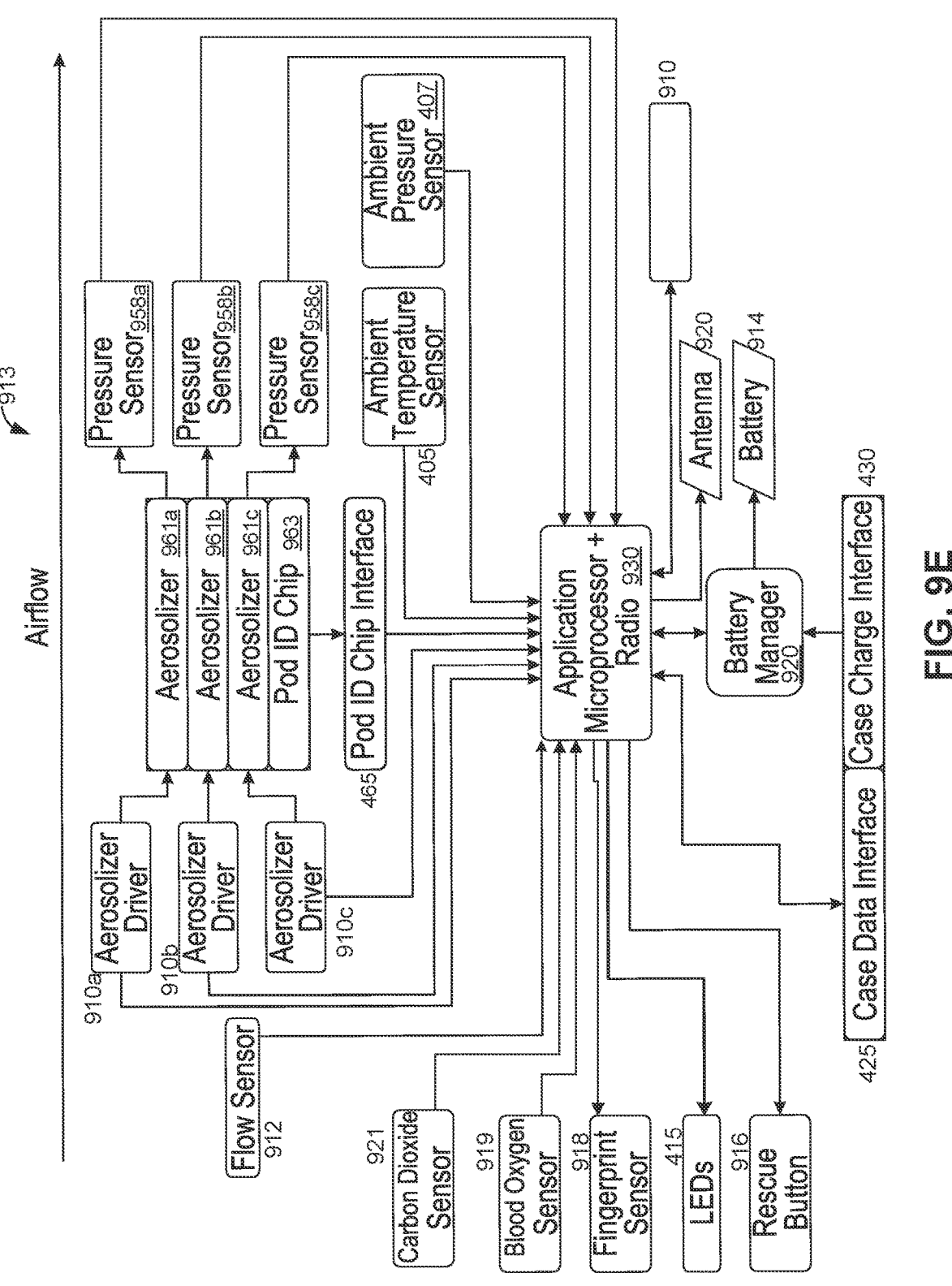

FIG. 9E is a schematic of a non-thermal example circuit that can be used in a drug delivery system, similar to the smoking cessation device illustrated in FIG. 3A

Figure 9F:
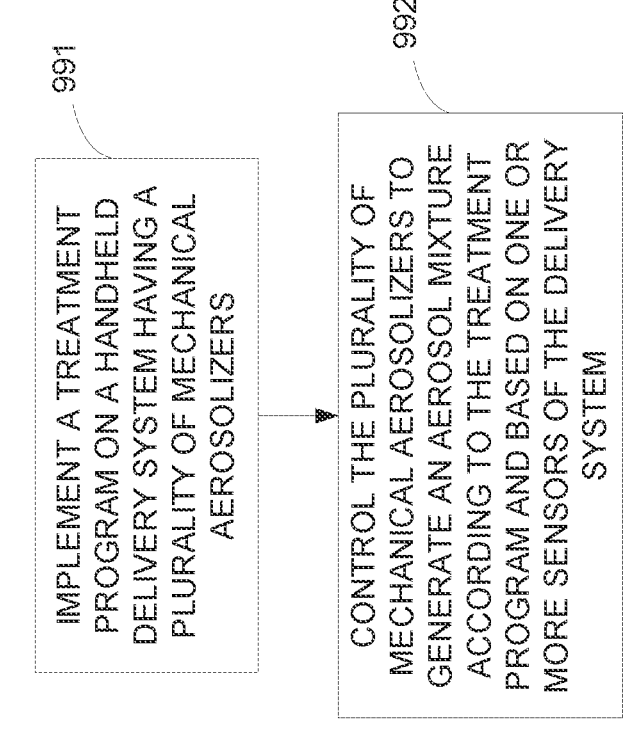

FIG. 9F is a flowchart illustrating an example of a drug dosage and delivery process, according to one embodiment.

Figure 10A:
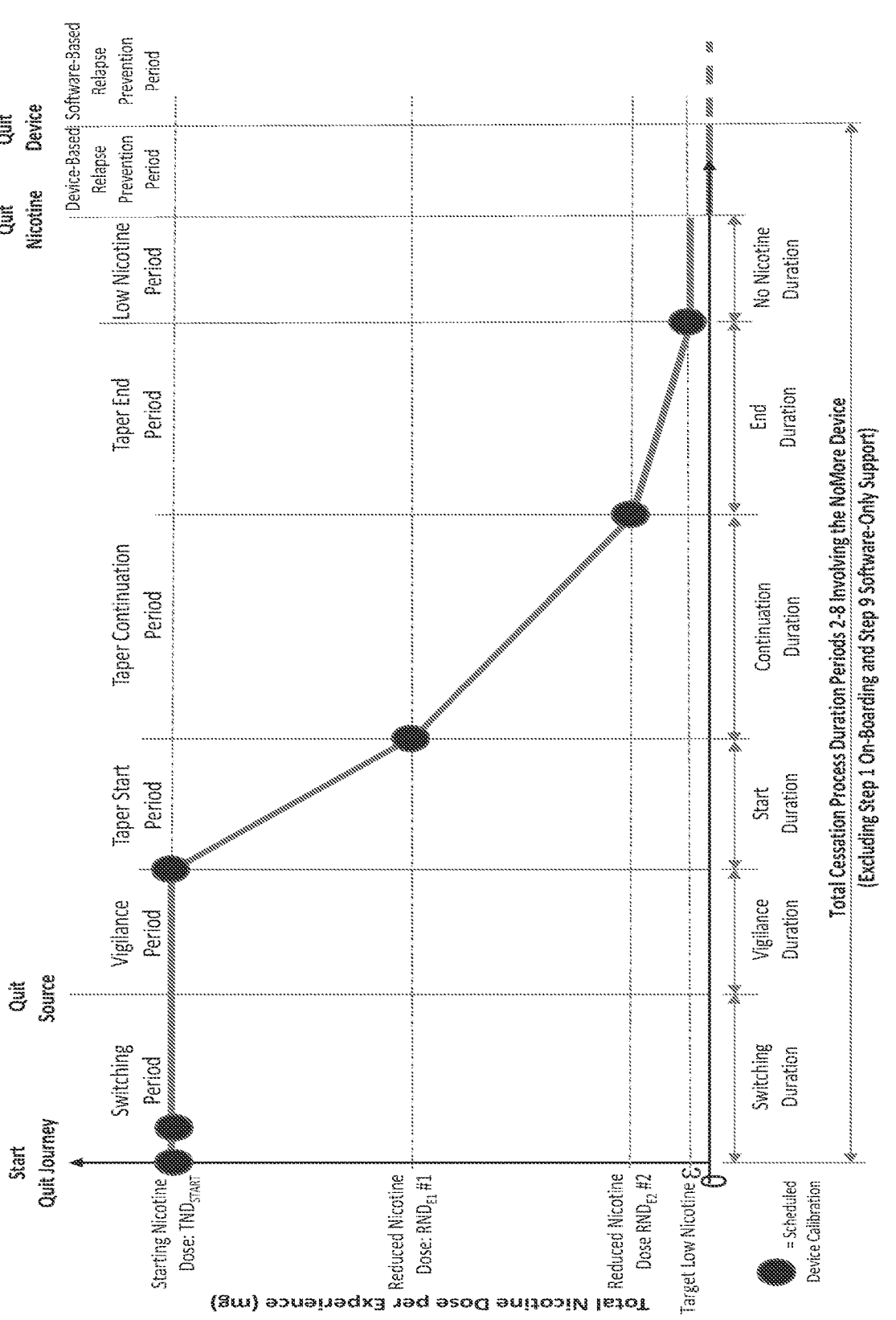

FIG. 10A is a graph illustrating the quit journey period and the taper parameters implemented in a cessation program.

Figure 1:
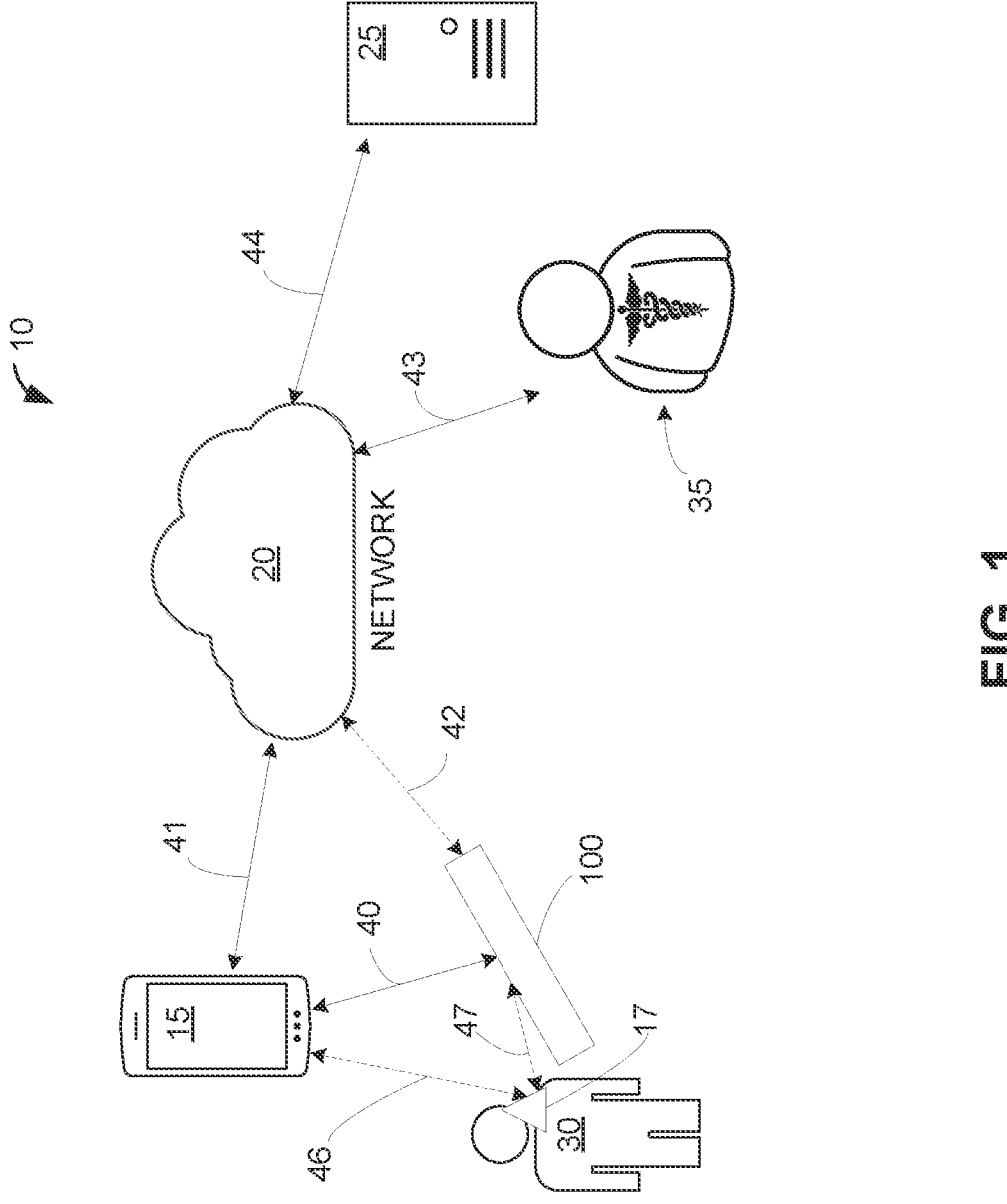
FIG. 1 illustrates an overview of an addiction cessation system, for example, a smoking or vaping cessation system ("cessation system").
Figures 1, 2, 3, 10B:
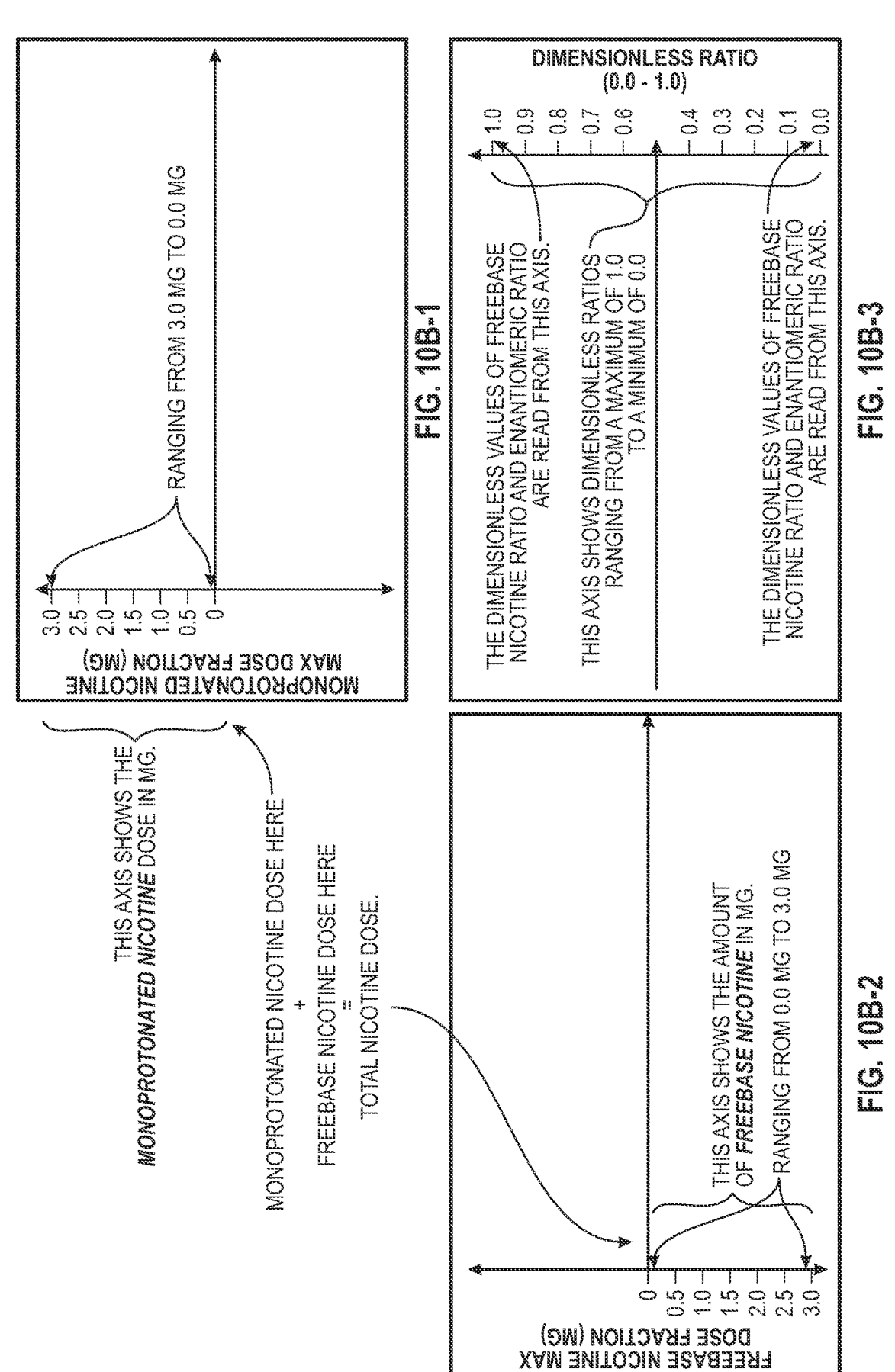

FIG. 10B-1 is a graph illustrating the dosage map specification of monoprotonated nicotine.

Figure 2:
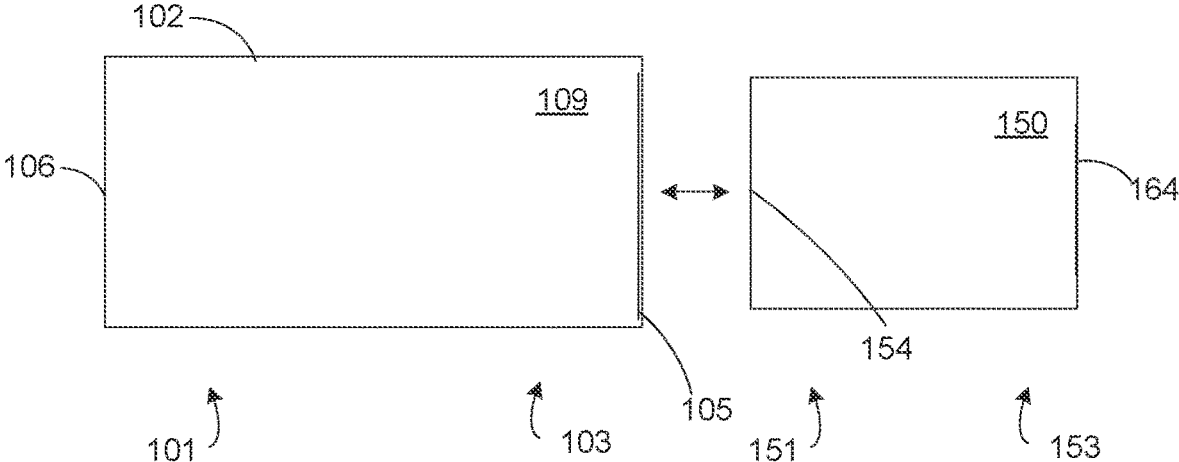
FIG. 2 is a schematic of an example of a cessation system that includes a housing and an aerosolizer system (or "aerosolizer pod") that can be removably coupled to the housing.

FIG. 10B-2 is a graph illustrating the dosage map specification of freebase nicotine.

FIG. 10B-3 is a graph illustrating the dosage map specification of dimensionless values for freebase nicotine ratio and enantiomeric ratio.

Figure 10C:
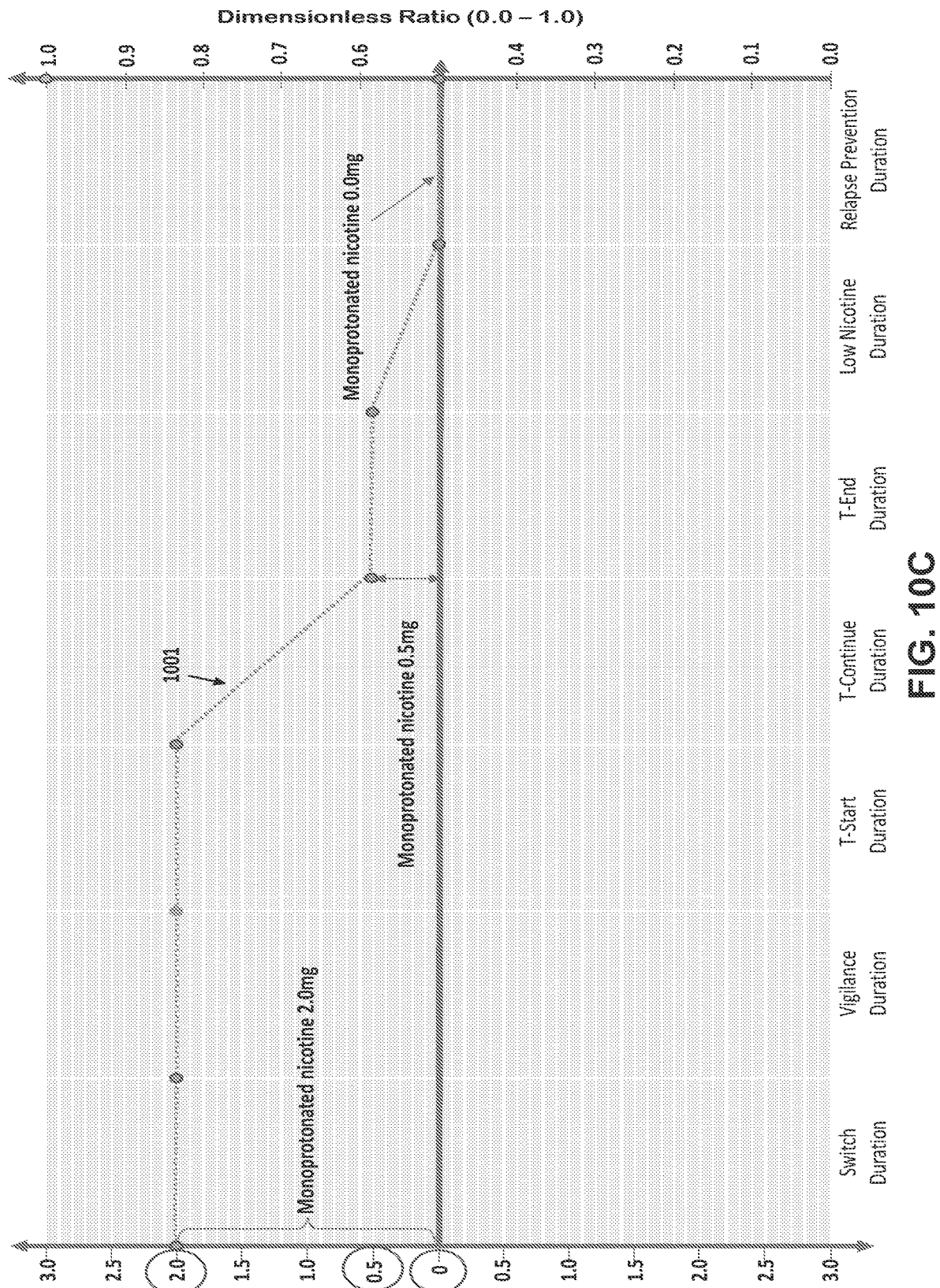

FIG. 10C is a graph illustrating the hypothetical dosage map specification of monoprotonated nicotine dose.

Figure 10D:
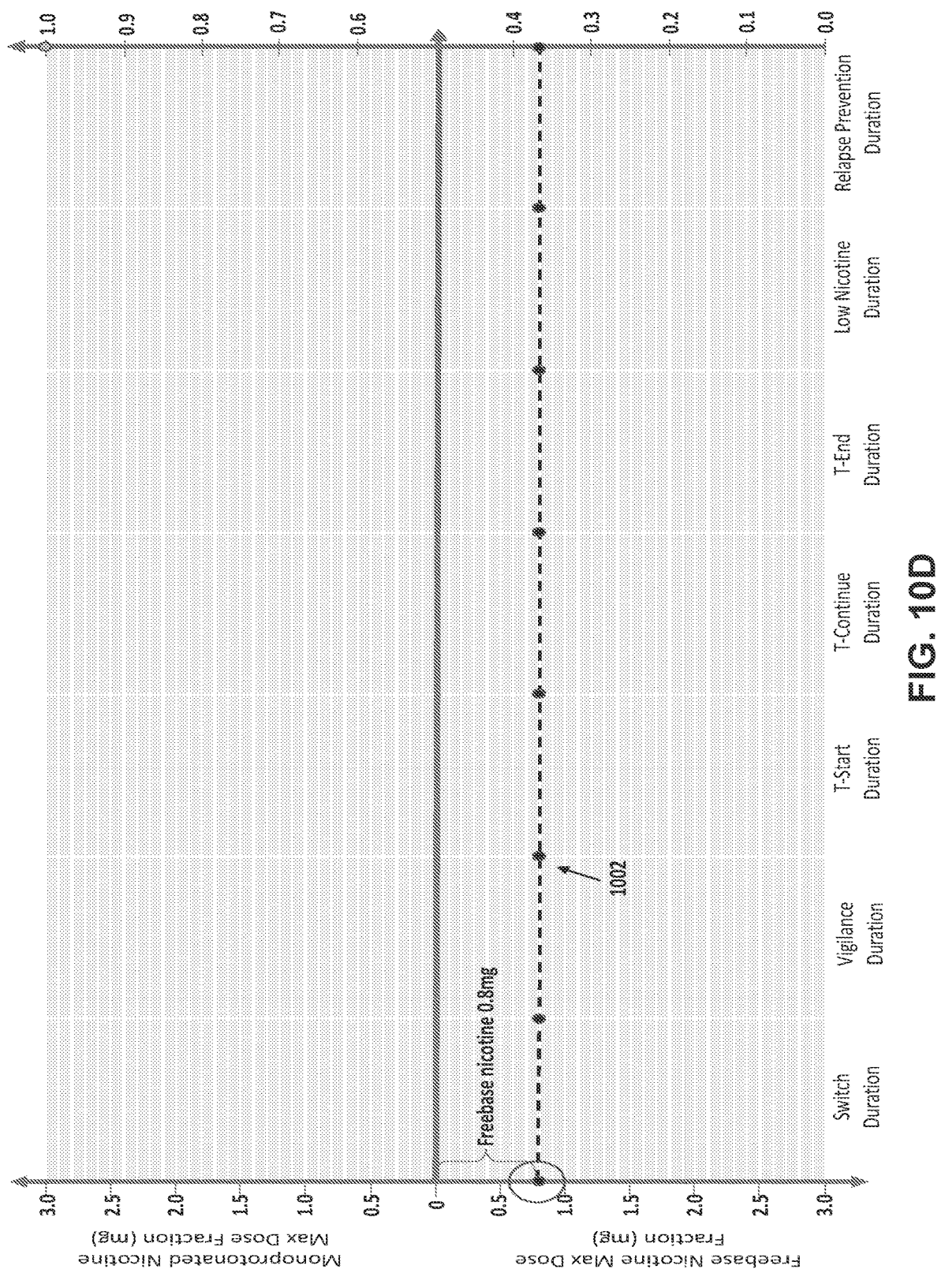

FIG. 10D is a graph illustrating the hypothetical dosage map specification of freebase nicotine dose (FND).

Figure 10E:
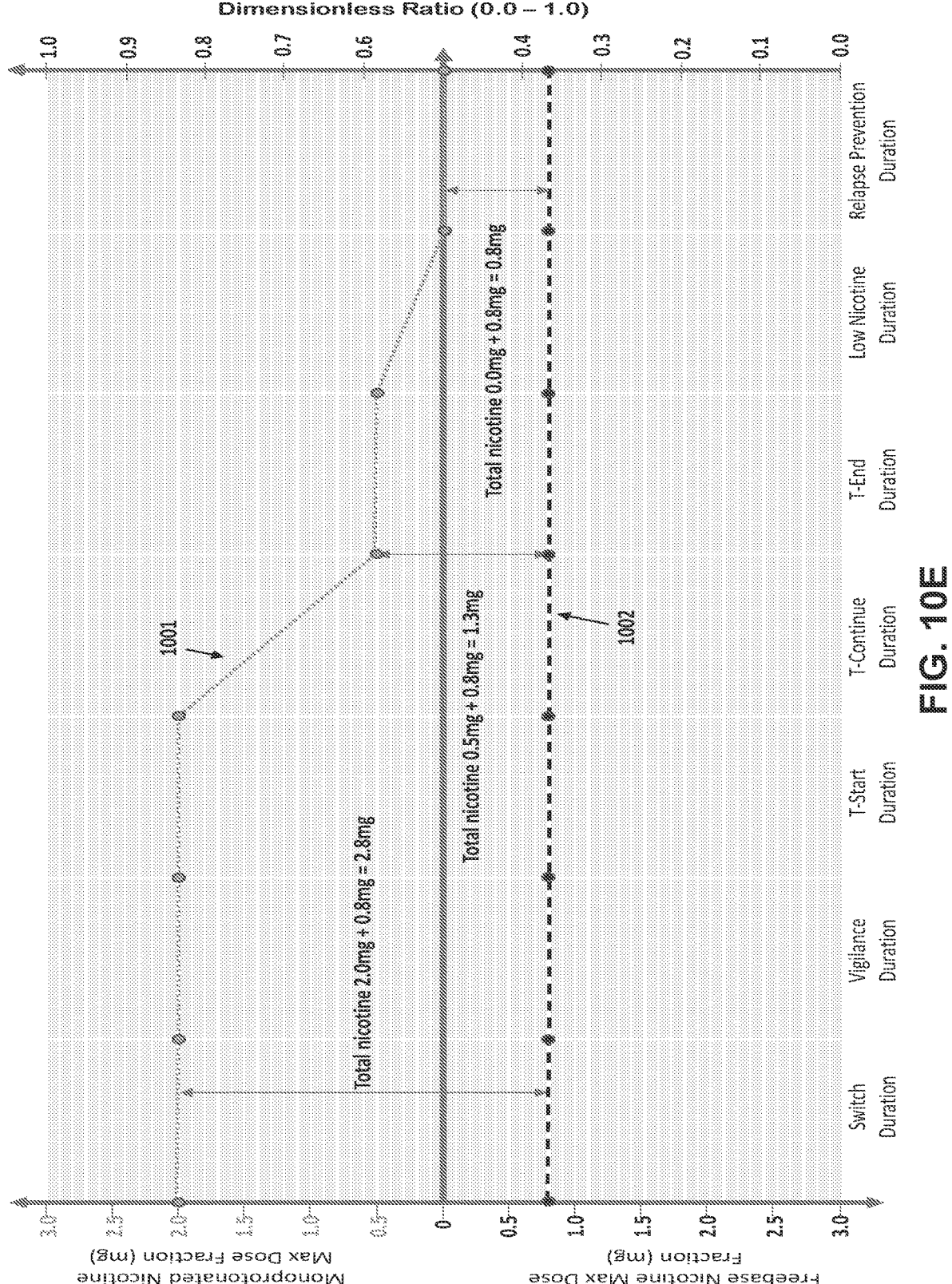

FIG. 10E is a graph illustrating the hypothetical dosage map specification of total nicotine dose (TND) (sum of monoprotonated and freebase).

Figure 10F:
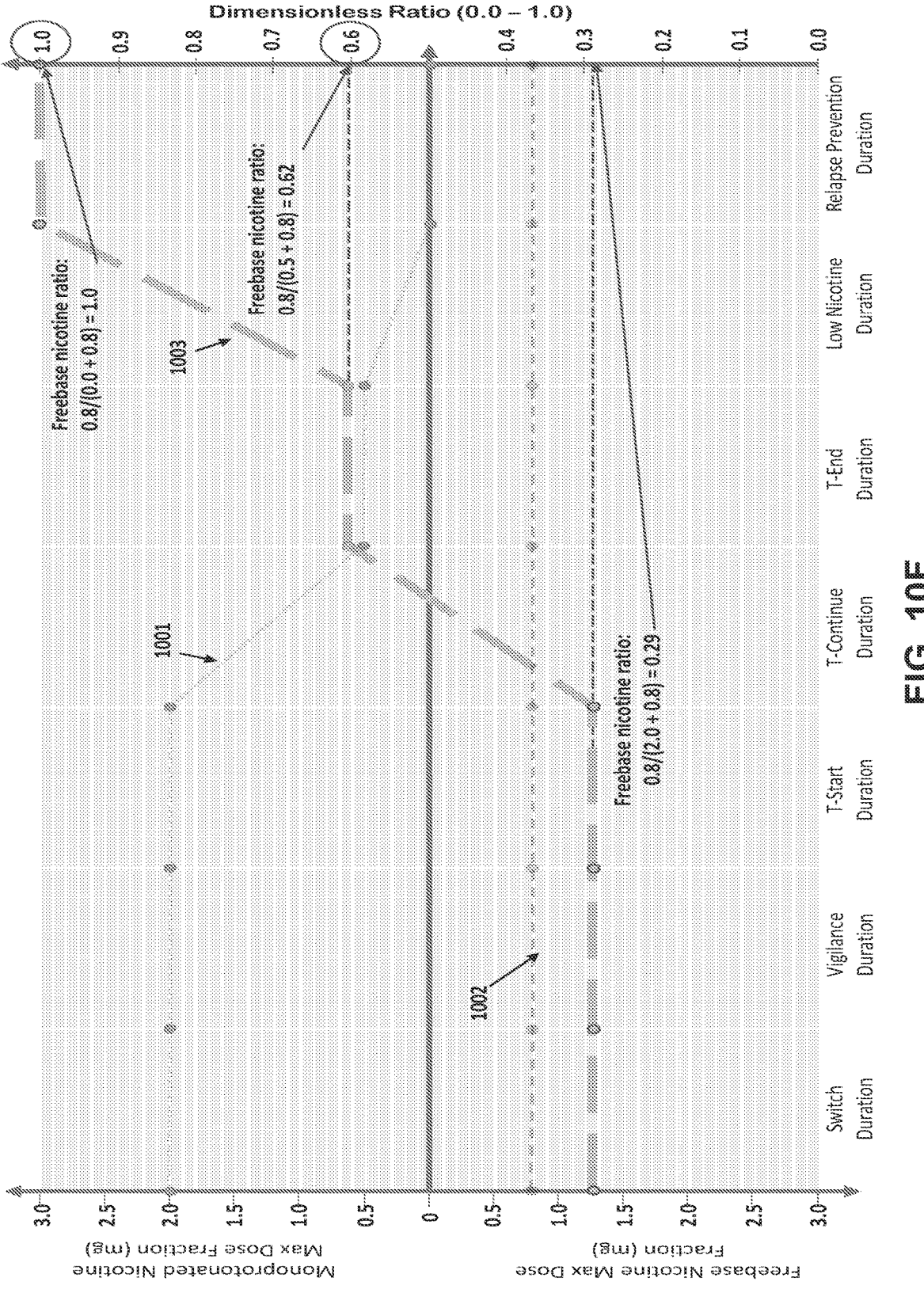

FIG. 10F is a graph illustrating the hypothetical dosage map specification of freebase nicotine ratio (FNR) (ratio of (free dose)/(total dose)).

Figure 10G:
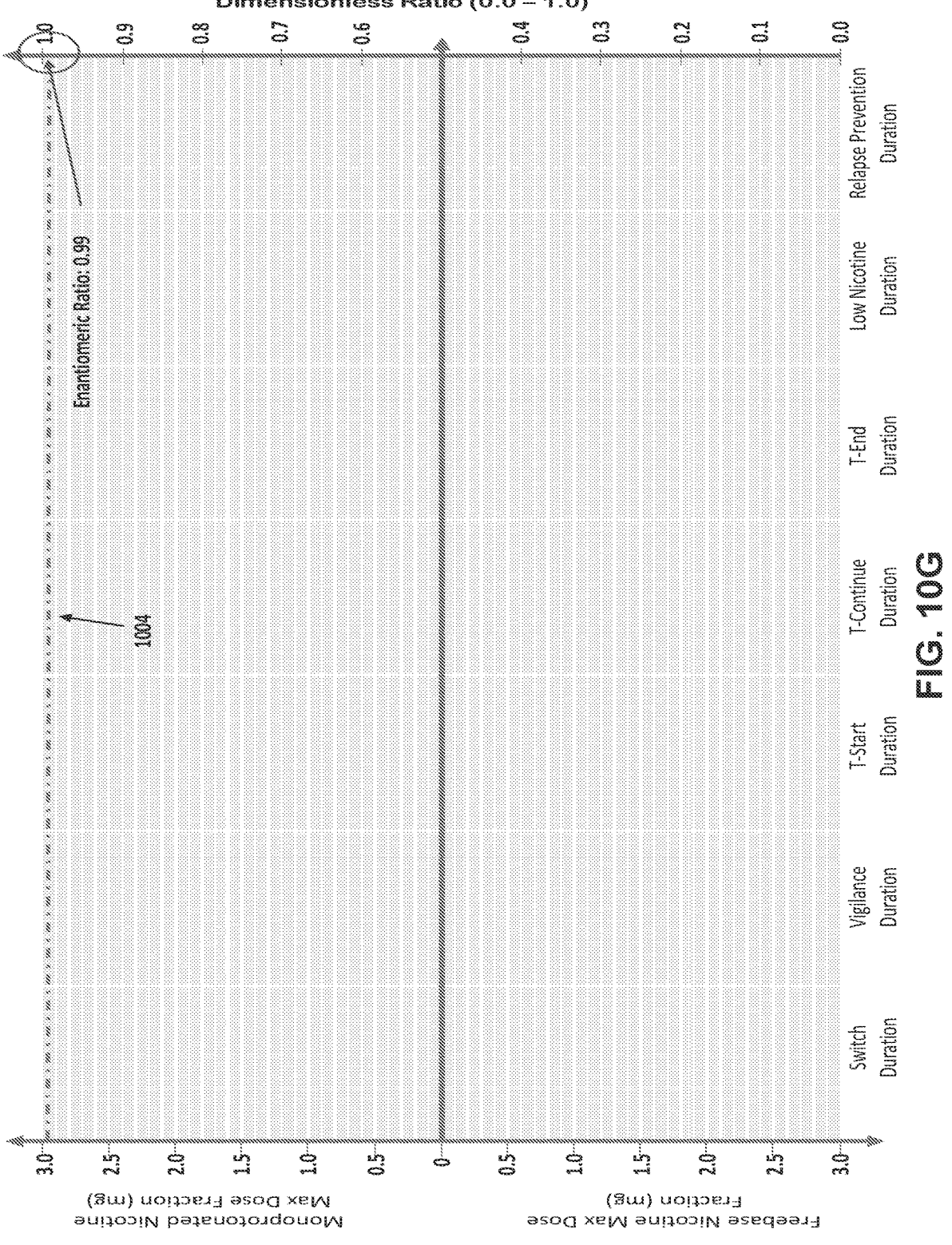

FIG. 10G is a graph illustrating the hypothetical dosage map specification of enantiomeric ratio (ratio of (S-nicotine)/(R-nicotine)).

Figure 10H:
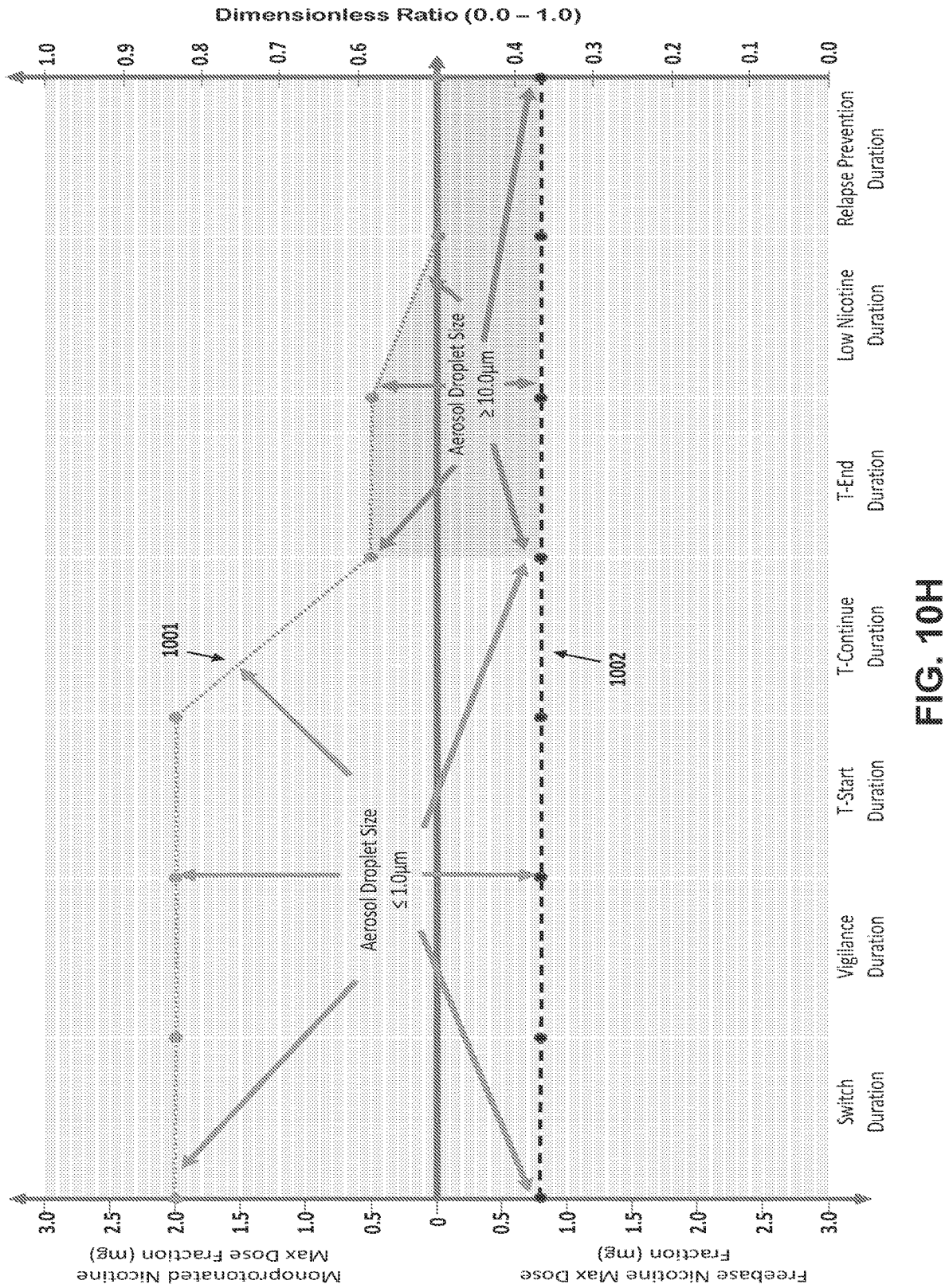

FIG. 10H is a graph illustrating the hypothetical dosage map specification of variable aerosol droplet size (ADS).

Figure 10I:
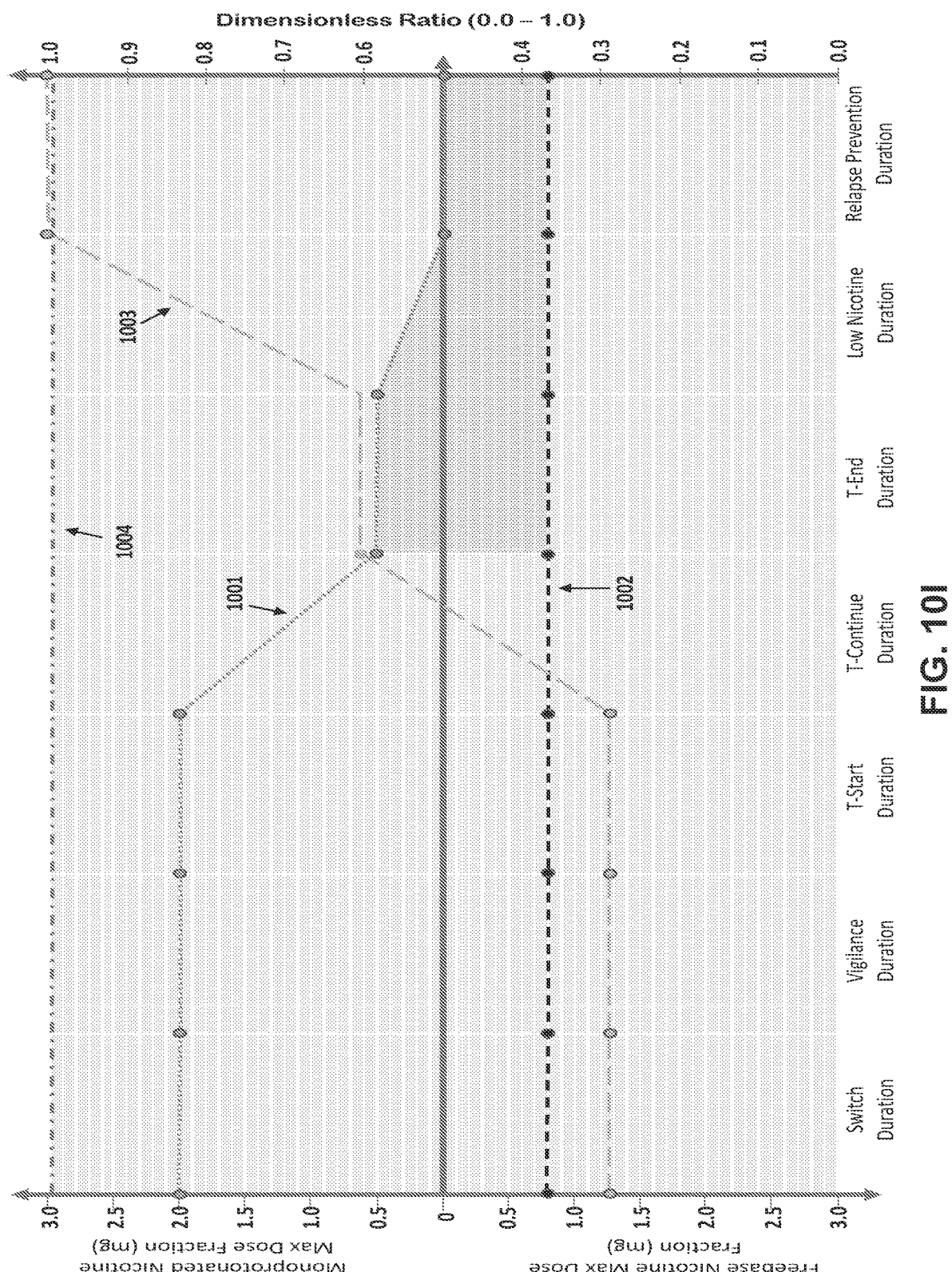

FIG. 10I is a graph illustrating the hypothetical dosage map specification of combined previous 6 taper variables shown as a function of the quit journey period, based on initial values of TND, FND and FNR, plus taper TND reduction targets.

Figure 10J:
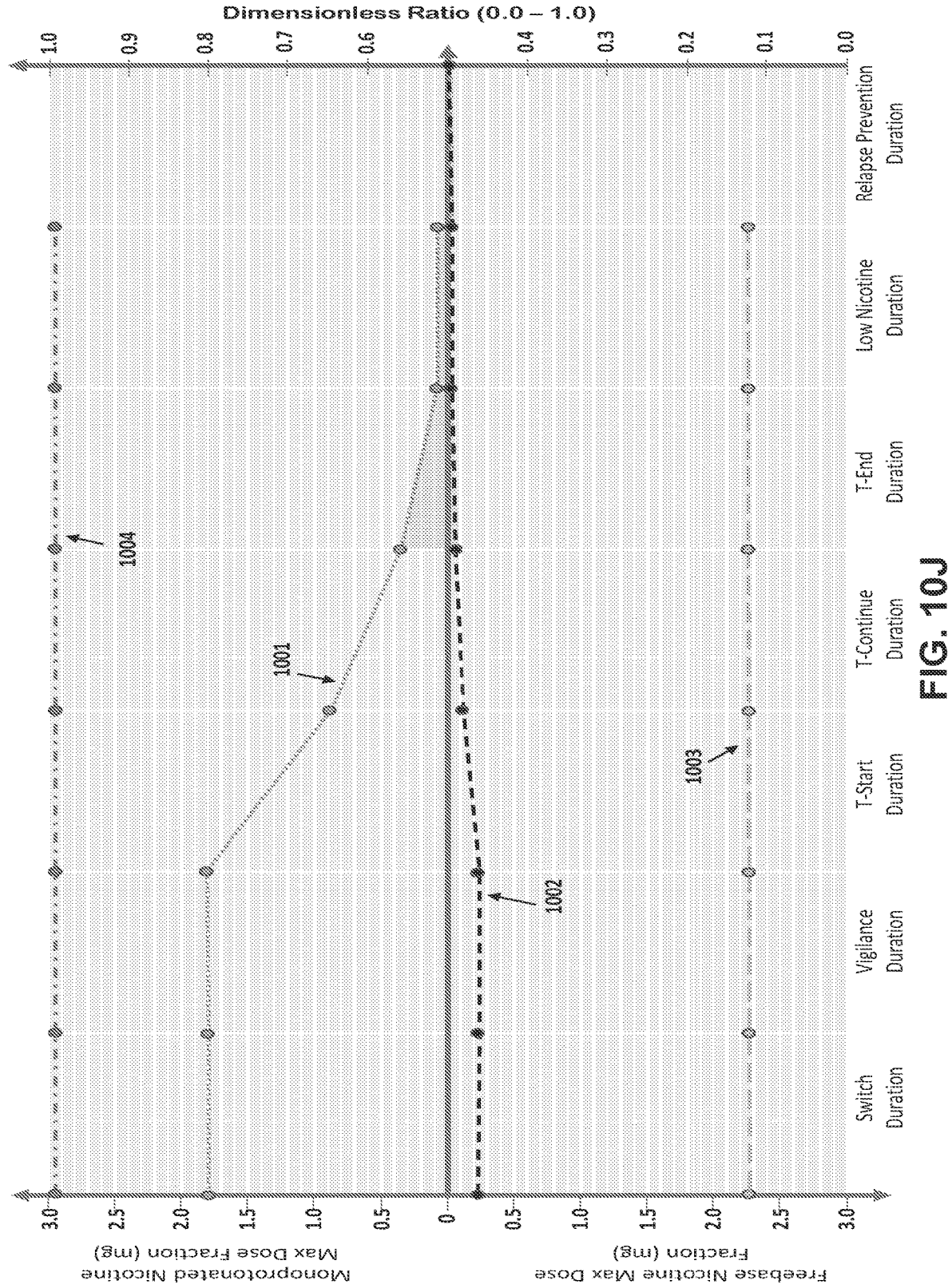

FIG. 10J is a graph illustrating an example of a representative dosage map specification of a cigarette-smoking patient (Patient 1—Marlboro Red@ 2.6 mg/cig with FNR=0.11, Taper regime $T_{FND}$(FNR constant)).

Figure 10K:
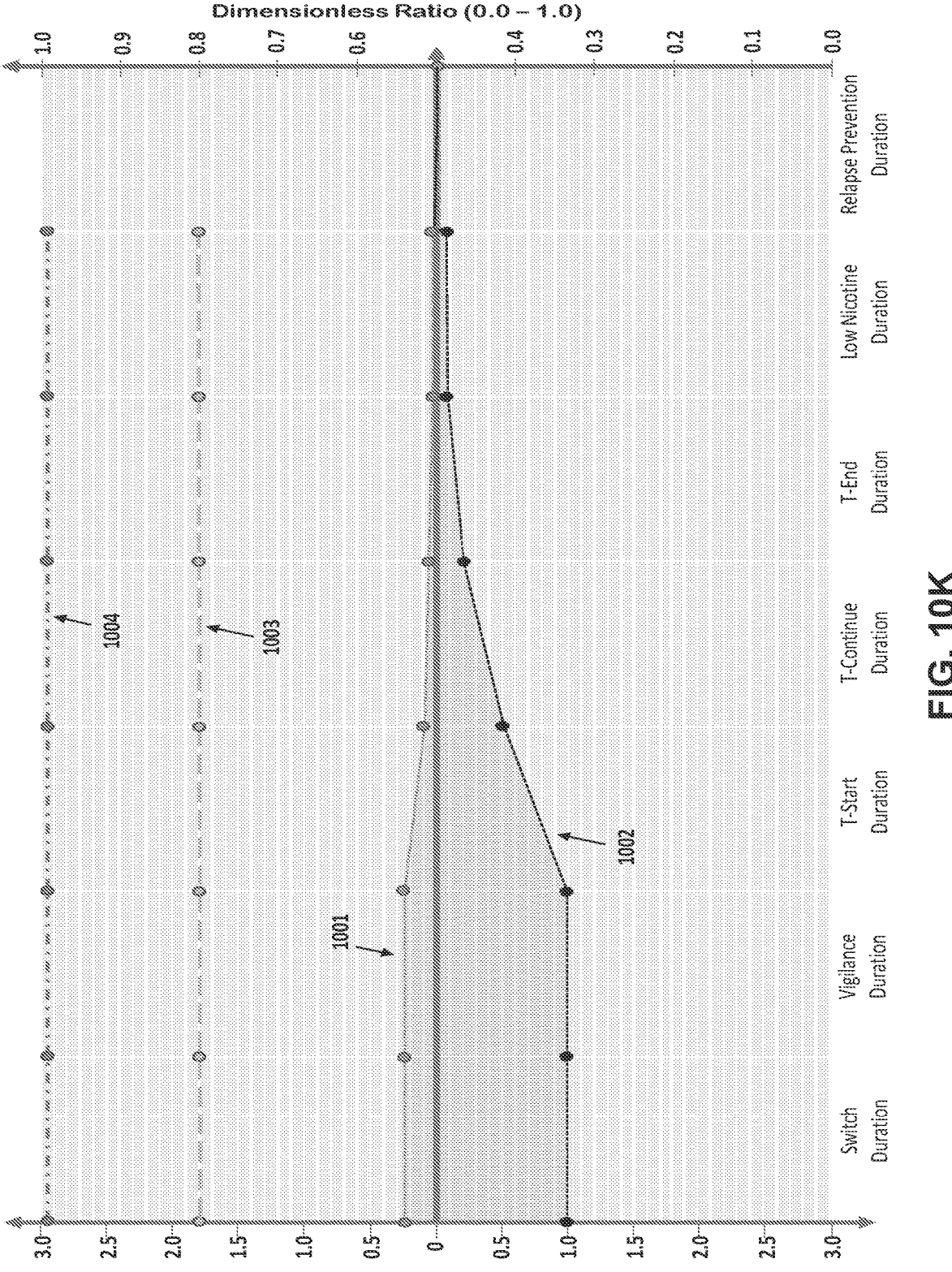

FIG. 10K is a graph illustrating an example of a representative dosage map specification of a vaping patient (Patient 2—Vapors' XROS & Zen-Haus e-Liq@ 17 mg/mL with FNR=0.84, Taper regime $T_{FND}$(FNR constant)).

Figure 10L:
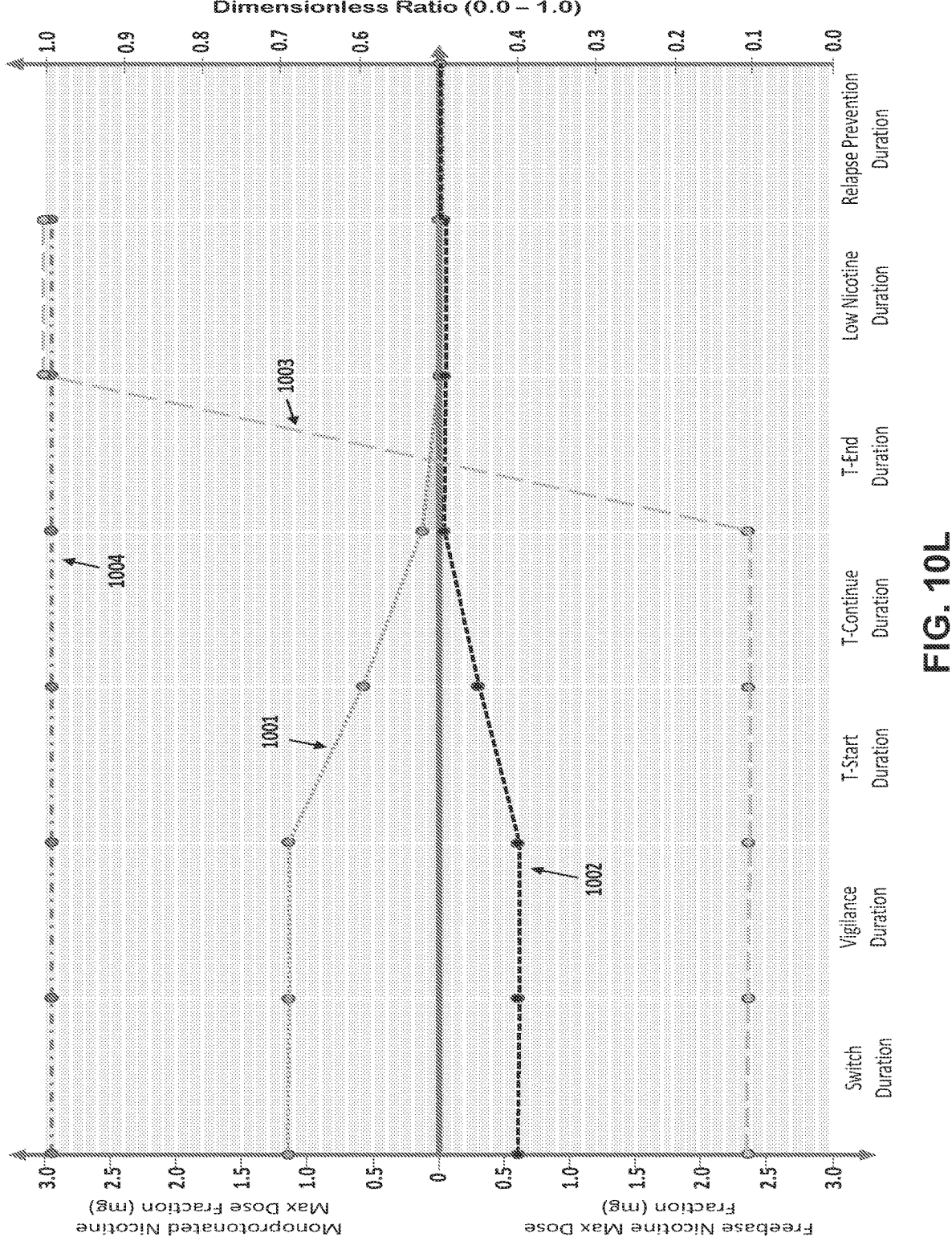

FIG. 10L is a graph illustrating an example of a representative dosage map specification of a cigarette-smoking patient (Patient 3—Winston Blue@ 1.7 mg/cig with FNR=0.05, Taper regime $T_{FND}$ initial (FNR constant) $T_{FNR}$ (FND constant)).

DETAILED DESCRIPTION OF CERTAIN INVENTIVE ASPECTS

The detailed description of various exemplary embodiments below, in relation to the drawings, is intended as a description of various aspects of the various exemplary embodiments, components, and methods implemented with a system for delivering substances to a user in accordance with an individually tailored treatment program, and is not intended to represent the only aspects in which the various exemplary embodiments described herein may be practiced. The detailed description includes specific details for the purpose of providing a thorough understanding of the various exemplary embodiments of the present invention. However, it will be apparent to those skilled in the art that some aspects of the various exemplary embodiments of the present invention may be practiced without these specific details. In some instances, well-known structures and components are shown in block diagram form in order to avoid obscuring various examples of various embodiments. It will be understood that unless a term is expressly defined in this disclosure to possess a described meaning, there is no intent to limit the meaning of such term, either expressly or indirectly, beyond its plain or ordinary meaning. Any element in a claim that does not explicitly state "means for" performing a specified function, or "step for" performing a specific function is not to be interpreted as a "means" or "step" clause as specified in 35 U.S.C. § 112.

This disclosure relates to systems and methods for delivering substances to a user in accordance with an individually tailored treatment program. For ease of reference, unless specifically indicated otherwise, the terms substance, drug, medicant, or active pharmaceutical ingredient (API) are used herein interchangeably unless indicated otherwise, explicitly or by context, and all may be referred to as a "substance." As a specific illustrative example, systems and methods are described are for delivering substances to a user for a smoking cessation treatment program. The disclosed systems, devices and processes can be used for many other treatment programs, as well, for example but not limited to, hormone replacement programs, programs for cessation of other addictions, etc. where it is desired to educate the patient, control administration of a plurality of drugs to the patient (e.g., substances, medicants, API's, etc.), and automatically monitor the drugs provided for precise tracking of the patient in the treatment program.

Accordingly, as an illustrative example, in some implementations, the systems, devices, and methods are employed to help a user stop smoking or vaping. For ease of reference, as used herein "smoking" is used in reference to smoking and/or vaping. Reference to a "smoking cessation device," a "smoking cessation system," or "a method for smoking cessation," or similar phrases, refer to either, or both, a device, system, or a method that can be used to facilitate a user to stop smoking, or to stop vaping. For example, a device, system, or a method that can be implemented in a cloud-based (or server-based) system for helping a user quit smoking or vaping, such as illustrated in FIG. 1, and described in further details in the subsequent figures. As mentioned above, the cessation systems, devices, and processes can be implemented in a smoking cessation program, or a vaping cessation program, the systems, devices, and processes can also be used to address, and quit, many other types of addictions. For example, the systems, devices, and processes can be used in many types of an addiction quitting program that benefits from having an individually tailored program based on user physiological and psychological characteristics, administering mixtures of multiple substances to a user via an inhalation device, daily automatic monitoring of the user's progress in the quitting program, and providing nearly instantaneous feedback to the user throughout each day of the quitting program, as needed. Accordingly, although many of the examples herein may relate to a smoking cessation program or a vaping cessation program, the uses of the disclosed systems, devices, and processes are not limited to these applications. For ease of reference, "smoking" is used herein to refer to either and both smoking and vaping unless otherwise indicated explicitly or by the context of the disclosure, such that a "smoking cessation program" refers to a smoking and/or a vaping cessation program. In addition, smoking is not limited to a tobacco product, but instead the applies to any substance or material that can be smoked, atomized, aerosolized, or sprayed, and inhaled by a user.

The difficulty of quitting smoking is well-known. The likelihood a smoker's attempt to quit smoking will be successful is greatly increased when both physiological and psychological aspects of smoking are addressed. To date, the physiological and psychological aspects of quitting smoking are generally addressed at least somewhat separately. Therefore, many smokers attempt to quit smoking or vaping using one or the other. Additionally, the lack of integration between the physiological and psychological aids also reduces the effectiveness of an attempt to quit smoking. In addition, during many, if not all, smoking cessation programs monitoring of the user's smoking behavior is based on user provided information and is not objectively collected, and there has been no way to accurately monitor and track the user's daily behavior. User provided information can be inconsistent and inaccurate at least for the reasons that as it may be unreliably collected and even falsely provided.

Figure 7A:
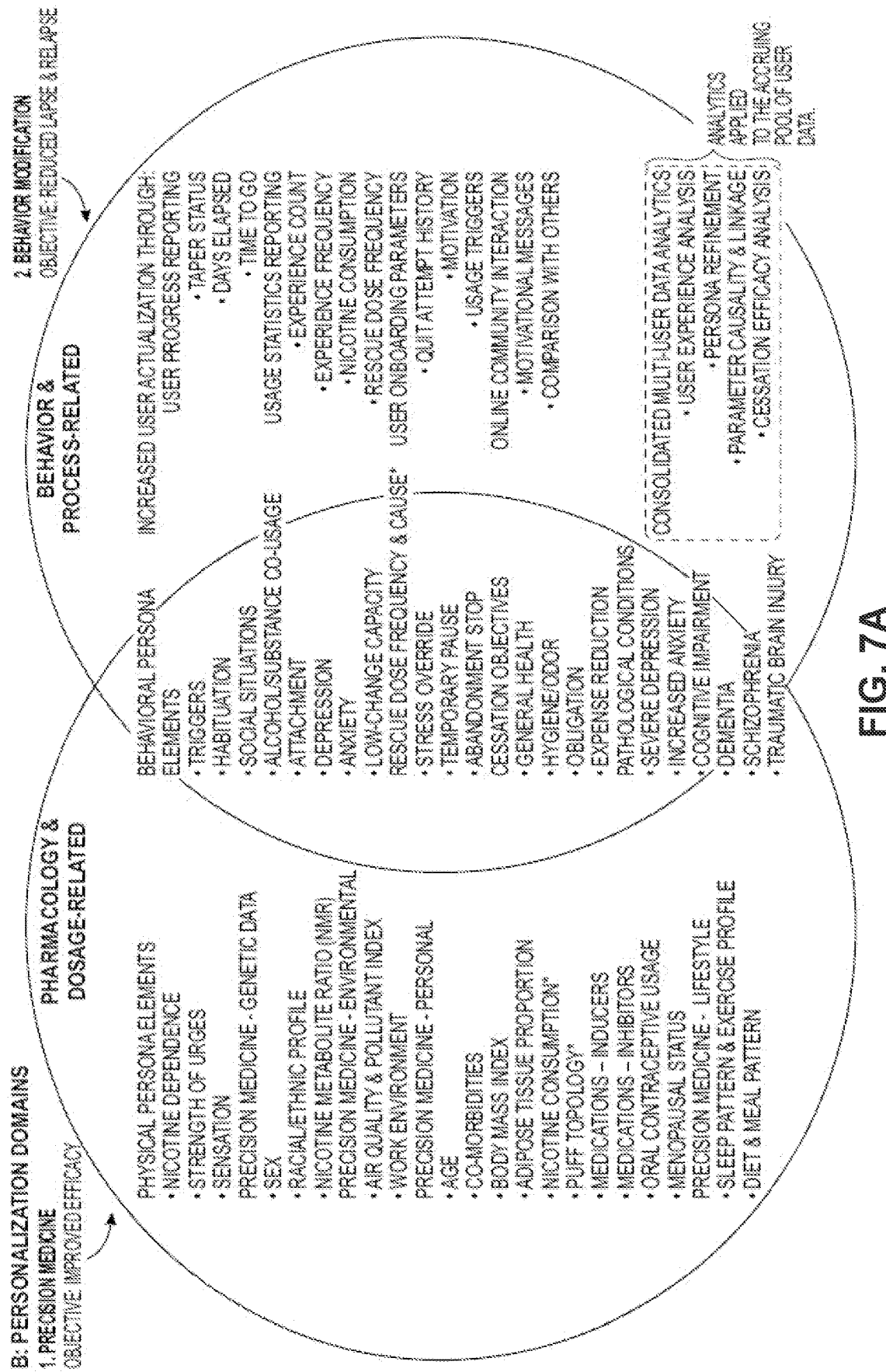
FIG. 7A is a diagram illustrating an example of intersecting personalization domains utilized by the smoking cessation system.

The systems, devices, and methods disclosed herein address these problems, and others. They advantageously can objectively monitor a user's activities, collecting accurate and detailed information of a user's use of a smoking cessation device as the user progresses through a cessation program, the collected information being relating to use characteristics of the cessation device that are impossible for a user to collect themselves. In the disclosed embodiments of a cessation program, is "onboarded" where a cessation program is individually generated based on user individual characteristics that may be genetic, determined from a user interview, and/or testing. For example, for smoking, one or more of nicotine dependence, strength of urges, perceived sensation of smoking, sex, race/ethnicity, nicotine metabolite rate (NMR), environmental (e.g., air quality, pollution index, work environment), age, co-morbidities, body mass index (BMI), adipose tissue proportion, nicotine consumption, puff topology, medications, oral contraceptives use, menopausal status, sleep pattern, exercise profile, and diet, nutrition, and meal pattern. These factors and others are illustrated in FIGS. 7A-7P, which disclose aspects of personalization of a smoking cessation treatment program, behavior modification objectives, and steps of the treatment program. For example, disclosing an exemplary smoking cessation process that includes on-boarding a user into the cessation program, cigarette taper, nicotine taper, placebo usage, and relapse protection (see, for example, FIG. 7Q). Information relating to onboarding is also described at least in reference to FIG. 8A.

Accordingly, in one implementation, a treatment system can provide an individually tailored dynamically controlled smoking cessation program to help a user quit smoking. The system can be a server-based system (e.g., cloud-based system), which is running at least a portion of the treatment program. The system can also include a user device (computer) that communicates with the server-based system. The user device includes a display that can provide information relating to the treatment program to the user. The system can also include a delivery device (e.g., an inhalation device) that administers an aerosol mixture to the user based on the treatment program. The delivery device can include components, a (computer) hardware controller and one or more sensors for providing the aerosol mixture to the user and monitoring the user of the delivery device. Signals from the sensors are used to monitor the user's use of the delivery device which can then be used to determine a user's progress through the treatment program and to dynamically tune the treatment program, as needed. For example, the hardware controller in the delivery device may monitor and record the number of "puffs" a user takes from the delivery device, determine a flow rate of air provided to the user during a puff, determine a duration of each puff (e.g., the length of time of a certain amount of air flow), determine a total inhaled time (e.g., cumulative), and/or determine an amount of substances ingested by the user based on its control of individual aerosolizers of the delivery device. Information indicative of the change in the rate of airflow during a puff can also be determined, and used to determine when to generate an aerosol mixture for most effective inhalation of aerosol mixture. Information is sensed by sensors of the delivery device (e.g., flow sensor, ambient temperature, and/or ambient pressure, and the like) can also be communicated to the user device and server system, and used to change (e.g., optimize) the treatment program. Information generated from the delivery device can be communicated to the user device (e.g., via a Bluetooth link), and certain information relating to the user's use of the delivery system may be displayed on the user device. Information received by the user device can also be communicated to the server-system to be used in the treatment application, The systems described herein can include a delivery device that is configured to control an aerosolizer system which can have a plurality of aerosolizers. The aerosolizer system can be incorporated in a pod (sometimes referred to herein a an "aerosolizer pod"). In some examples, a pod includes an aerosolizer system having two aerosolizers, each aerosolizer having a corresponding container holding a substance (e.g., a fluid) that is provided to the aerosolizer for use in generating aerosol. In some implementations, an aerosolizer system has two or more containers corresponding to each aerosolizer, such that the fluids held in the two or more containers are provided to a single aerosolizer. Each container can hold a substance (e.g., drug, medicant, etc.) that is needed to provided to the user according to the treatment program. In some examples, the containers hold the same substance, but typically they hold different substances to allow aerosol mixtures of the different substances to be administered to the user. In an example of a delivery device used in a smoking cessation treatment program, the delivery device includes two aerosolizers and two containers (a container corresponding to each aerosolizer). The first container can hold a first fluid comprising monoprotonated nicotine. The first fluid can also include a flavorant (e.g., any substance that provides a perceived flavor to the user when inhaled as an aerosol). The second container can hold a second fluid comprising freebase nicotine. The second fluid can also include a flavorant (e.g., any substance that provides a perceived flavor to the user when inhaled as an aerosol). In some examples, including examples illustrated in FIGS. 3A, 3B, 3C, and 4, an aerosolizer system includes three aerosolizers. In some examples, the aerosolizer system can include four or more aerosolizers. Each aerosolizer is associated with a substance and generates an aerosol from its associated substance. The delivery device is configured to control each aerosolizer individually such that the plurality of aerosolizers generate aerosol mixtures based on an individually tailored treatment program (e.g., a smoking cessation treatment program). That is, the delivery device is configured to control the aerosolizers, in accordance with the treatment program, to produce an aerosol mixture that includes an amount of two or more substances. The delivery device is configured to control each aerosolizer individually, in accordance with the treatment program, to produce an aerosol mixture that includes an amount of two or more substances. In addition, in some embodiments (e.g., where the aerosolizers are thermal-based aerosolizers) the delivery device can control each aerosolizer individually, in accordance with the treatment program, to generate aerosol having a desired droplet size such that the resulting aerosol mixture comprises droplets of a desired size, which affect where the aerosol is deposited in the mouth, throat, and/or lungs of the user. Additional details and certain illustrative embodiments of the treatment system, the delivery system, the user device, and related methods are described hereinbelow.

Although particular aspects various exemplary embodiments are described herein, numerous variations, combinations and permutations of these aspects fall within the scope of the disclosure. Although some benefits and advantages of certain aspects are mentioned, the scope of the disclosure is not intended to be limited to particular benefits, uses or objectives.

LIST OF CERTAIN COMPONENTS

For ease of reference, below is a list of certain components that are described and enumerated in this disclosure in reference to the above-listed figures of a cessation system. Other components not listed below may also be included in a drug-delivery treatment system. Any aspect of the items in the list below, or illustrated and/or described in the figures and description, whether or not named out separately herein, can form a portion of various embodiments of the invention and may provide basis for claim limitation relating to such aspects, with or without additional description. Certain enumerated items of the figures include:

10—treatment system (e.g., smoking cessation system)

15—user device (e.g., mobile device/smart phone/computer)

17—sensor(s) (e.g., wearable, patch, etc.)

20—network

25—server system (e.g., cloud-based server system)

30—user

35—advisor(s)/medical practitioner(s)

40—communication link between delivery device and user device

41—communication link between mobile device and network

42—optional communication link between cessation device and network

43—communication link between network and advisor (s)/medical practitioner(s)

44—communication link between server system and network

46—communication link between sensor and user device

47—communication link between sensor and delivery device

100—delivery system (e.g., delivery device 109 and pod 150)

101—distal end of housing

102—housing

103—proximal end of housing

104—channel

105—opening in housing for receiving aerosolizer system

106—opening for receiving air

107—proximal end of channel

108—opening on proximal end of channel for providing air to aerosolizer system

109—delivery device (or "pen")

110—aerosolizer driver

111—electrical connection(s)

112—flow sensor

113—circuit

114—power source (e.g., battery)

116—rescue button

118—fingerprint sensor

119—carbon dioxide sensor/oxygen sensor

120—antenna

121—carbon dioxide sensor

122—distal end of channel

130—controller

140—cavity for receiving aerosolizer system

141—cessation device exhaust port

145—substance (in aerosolizer container)

150—aerosolizer system (pod)

151—distal end aerosolizer system

152—heating element

153—proximal end aerosolizer system

154—intake (opening) of aerosolizer

155—proximal end passage

156—passage

157—distal end of passage

158—temperature sensor

159—aerosolizer container

160—density sensor

161—aerosolizer (unit)

162—aerosol mixing chamber

163—pod ID chip

164—exhaust port (opening) of mixing chamber for providing aerosol mixture

165—case

166—walls of mixing chamber

167—mixing space (volume) in mixing chamber

167—charging connection to pen

168—case battery

169—charging port

170—mixing chamber intake opening

171—sensing port

172—exhaust port sensor(s)

405—ambient temperature sensor

407—ambient pressure sensor

410—flash memory

415—LEDs

420—Battery Manager

425—case data interface

430—case charge interface

465—pod ID chip interface

500—computer system

502—communication bus

504—hardware processor

506—non-transitory memory (component)

510—storage device (e.g., solid-state memory)

512—display

514—input controls

518—communication interface

601—puff data

602—usage

603—profile

604—data input

605—progress

606—output

607—cessation schedule

608—cessation application

801—on-boarding phase

802—cigarette taper phase

803—nicotine taper phase

804—placebo usage phase

805—software support phase

850—treatment program phase 1 (after onboarding)

851—treatment program phase 2

852—treatment program phase n−1

853—treatment program phase n

900—drug delivery system

901—distal end

902—housing

903—proximal end

904—channel

905—opening in housing for receiving pod

906—opening for receiving air

907—ambient temperature sensor

908—opening

909—drug delivery device

910—aerosolizer drivers

911—electrical connections

912—flow sensor

913—ambient pressure sensor

914—power source (e.g., battery, capacitor(s))

916—rescue button

918—fingerprint sensor

920—antenna

930—controller circuit

940—cavity for receiving pod

950—pod

951—distal end of pod

952—non-thermal aerosol generating component

953—proximal end of pod
954—container (for holding drug)
955—distal end passage
956—passage
957—proximal end passage
959—drug container
960—sensor (e.g., density, temperature)
961—non-thermal aerosolizer assembly
962—mixing chamber
963—pod ID chip
964—opening, exhaust port where aerosol exits pod
966—walls
967—mixing space (cavity)

Illustrative Example of Treatment System for Smoking Cessation

FIG. 1 illustrates an example of system 10 that can be used to precisely and dynamically administer substances in accordance with a treatment program, monitor the patient's use of the substances throughout the treatment program, and provide feedback to the patient and others on the patient's progress in the treatment program. For ease of reference, a provided or administered "substance," as used herein, is a broad term that refers to drugs, medicants, API's, or another material that is provided to a user by a delivery device as part of a treatment program. As an illustrative embodiment, a system, delivery devices, and methods are described for a smoking cessation treatment program. Smoking cessation treatment programs include cessation of any type of smoking, or inhaling any type of tobacco or non-tobacco product, including vaping, using an electronic device. Although the illustrative embodiment is for a smoking cessation treatment program, the described system, devices and methods are not limited to smoking cessation but instead can be used for other types of treatment programs where substances are administered to a patient over a duration of time. In particular, treatment programs where a combination of substances are delivered to a patient over a period of time, and the amount of the substances is dynamically changed over time based on the treatment program. Examples of other treatment programs can include treatment programs related to hormones or hormone replacements, drug addiction, allergies, pain mitigation, and the like.

Specifically, FIG. 1 illustrates examples of components and communication links that can exist between the components of a treatment system ("system") 10. In this example, the system 10 includes a server system 25, a delivery system 100 used by a user 30, and a user device 15. One or more advisors or medical practitioners 35 can also receive information relating to the treatment program and the user's progress in the cessation program, and provide input to the cessation program or to the user 30. In some embodiments, the system 10 can also include a sensor 17, which can be in communication with the delivery system 100 and/or the user device 15.

The components of the system 10 can communicate via a network 20, and one or more communication links. This example includes a communication link 40 between the delivery system 100 and the user device 15, a communication link 41 between the user device 15 and the network 20, a communication link 43 between the advisors 35 and network 20, a communication link 44 between the server 25 and the network 20. In embodiments having a sensor 17, a communication link 46 can exist between the sensor 17 and the user device 15, and/or a communication link 47 can exist between the sensor 17 and the delivery system 100. One or more portions of the network 20 and communication links 40-44, 46, 47 can be a wired or wireless communication link, and can include Wi-Fi, Bluetooth, cellular, or any suitable communication link. The network 20 can be, for example the Internet, or another large area network (LAN), or a wide area network (WAN). In some examples, the delivery system 100 can include directly to the network 20 via a communication link 42 (e.g., a wireless communication link).

Figure 3B:
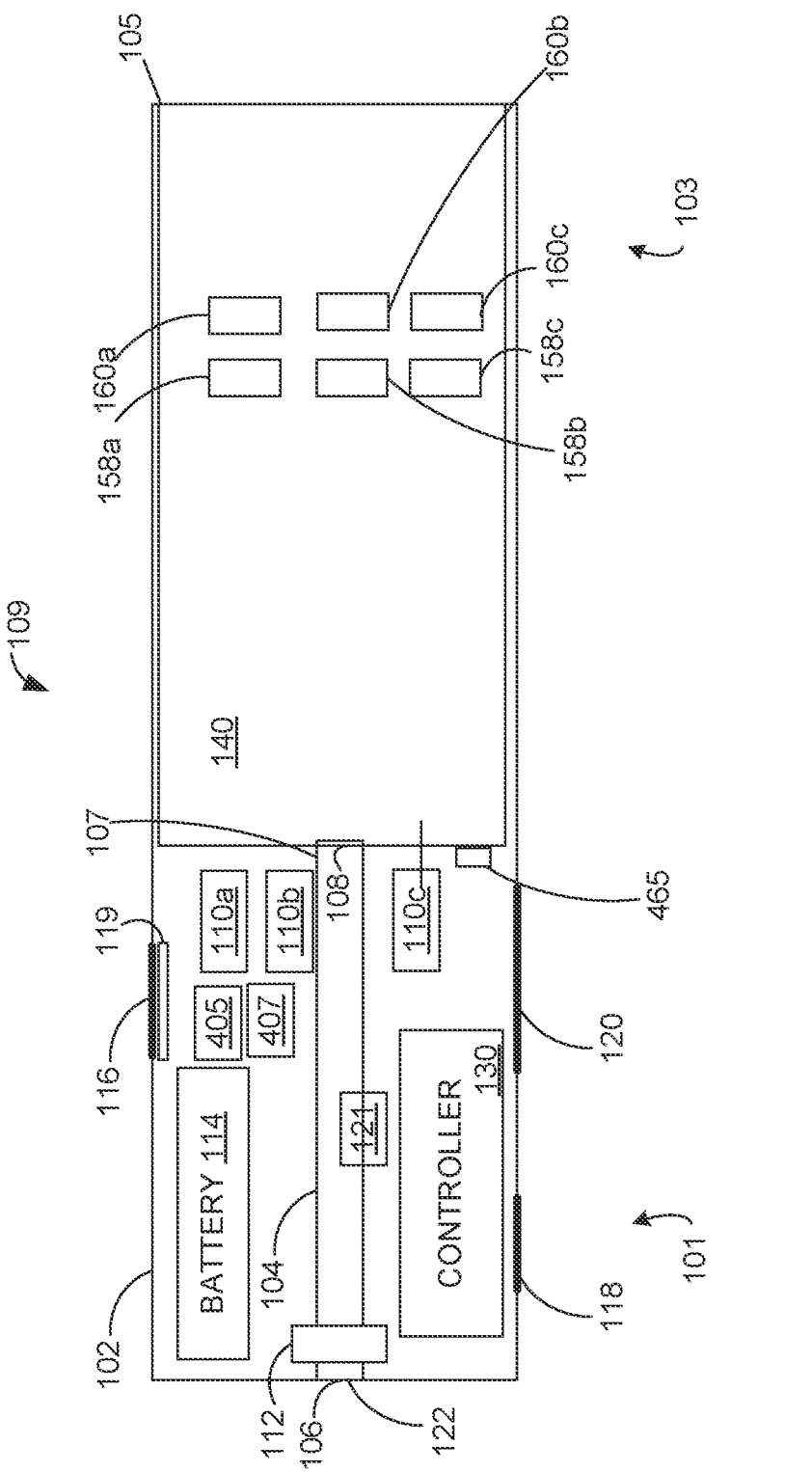
FIG. 3B is a schematic of the housing of the cessation system illustrated in FIG. 3A.
Figure 4:
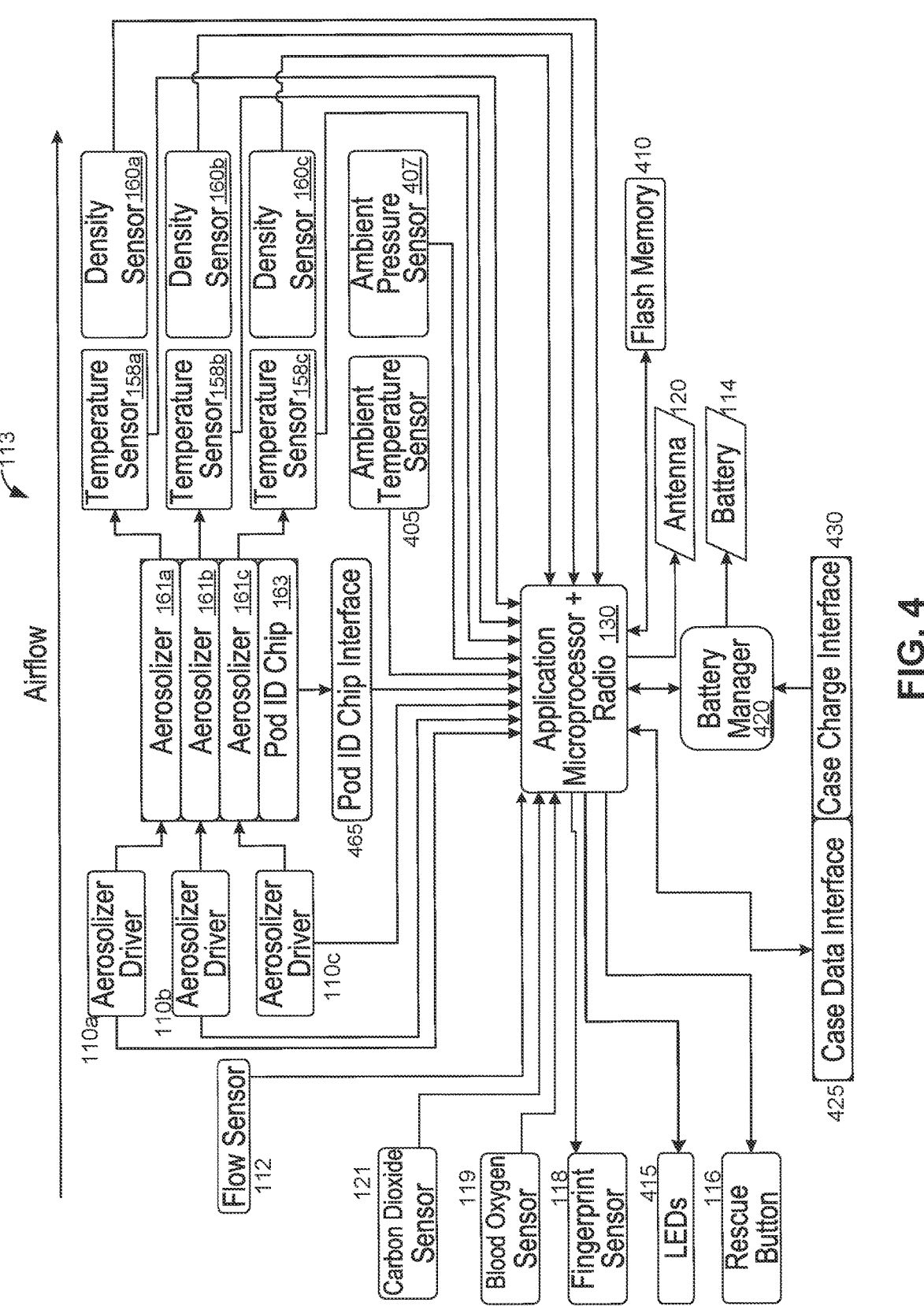
FIG. 4 is a schematic of an example of a controller that can be used in a cessation system, showing communication lines between a hardware processor and other components of the cessation system.

In this example, the server 25 is configured with a smoking cessation treatment program which is tailored to an individual user. As described below (for example in reference to FIGS. 7A-7Q, 8) at the beginning of the treatment program the user is "onboarded" and an individually tailored program is generated using factors specific to the user (see, for example, one or more of factors as shown in FIGS. 7A, 7B-1, and 7B-2). The server 25 provides information to the user device 15 to operate the treatment program, and the user device 15 provides information to the delivery system 100, which may include software updates, revised treatment program information and control parameters, and the like. During a treatment program, the use of the delivery system 100 is monitored by the delivery system 100 using one or more sensors incorporated into the delivery system 100. FIGS. 3A, 3B, and 4 illustrated examples of sensors that may be included on the delivery system 100. Information related to the treatment program can be communicated from the delivery system 100 to the user device 15, and then to the server 25. The information received by the server 25 can be used by the server 25 to monitor and/or revise the cessation program. The information received by the sever 25 can also be used to provide reports to advisors 35. In addition, the information received by the server 25 for each user can may be used as information to change overall parameters of the treatment program for other users. For example, information from hundreds, thousands, tens of thousands or more of users can be used to increase the efficiency and the effectivity of the treatment program for current users and/or new users. In some examples, machine learning processes can be used with a dataset of information of numerous users to determine parameters of the treatment program.

The user device 15 can be a smart phone, a tablet computer a laptop computer, or another mobile computing device. The user device 15 can also be a desktop computer, a specialized computer in a medical practitioner's facility, or another suitable computer resource. In some preferred embodiments, the user device is a mobile computing device that a user can conveniently have with them at all times, or most of the time (e.g., a smart phone). The user device 15 can provide treatment program information to the cessation (or "delivery") device 100, including information which is used to control generation of an aerosol mixture that the delivery system 100 controls the generation of, from a plurality of aerosolizers. The aerosolizers can be dynamically controlled to provide desired aerosol mixtures as required by the cessation program. In some embodiments, the user device 15 can run at least a part of the cessation program, for example, through an app running on the user device 15. The user device 15 includes a display, and provides certain cessation program information to the user 30 on various graphical user displays (GUI's) of the display based on the received information, for example, information relating the user's progress, or encouraging information for the user to adhere to the cessation program. The user device 15 also receives information from the delivery system 100 relating to the user's use of the device (including information from sensors on the delivery system 100), and can communicate some or all of the received information to the server 25. As indicated above, the user device 15 can communicate changes/revisions of the cessation program and related information, including revisions to software or new software, to the cessation system 100, including information the user device 15 receives from the server 25.

In this embodiment, the delivery system 100 is an aerosol generating inhalation-type device used by the user 30 to help the user 30 stop smoking or vaping. The delivery system 100 can include a delivery device 109 and an aerosolizer pod 109 (e.g., illustrated in FIG. 2). In some embodiments, the delivery device includes a plurality of aerosolizers and the pod includes containers that hold substances (e.g., fluids) that are provided to the aerosolizers. In the embodiment illustrated in FIGS. 2, 3A-3C, the delivery device 109 includes a controller, one or more sensors, and other components that are used to control the generation of an aerosol mixture, and the pod 150 includes a plurality of aerosolizers and a plurality of containers each containing a substance that is provided to the aerosolizers.

Figure 3C:
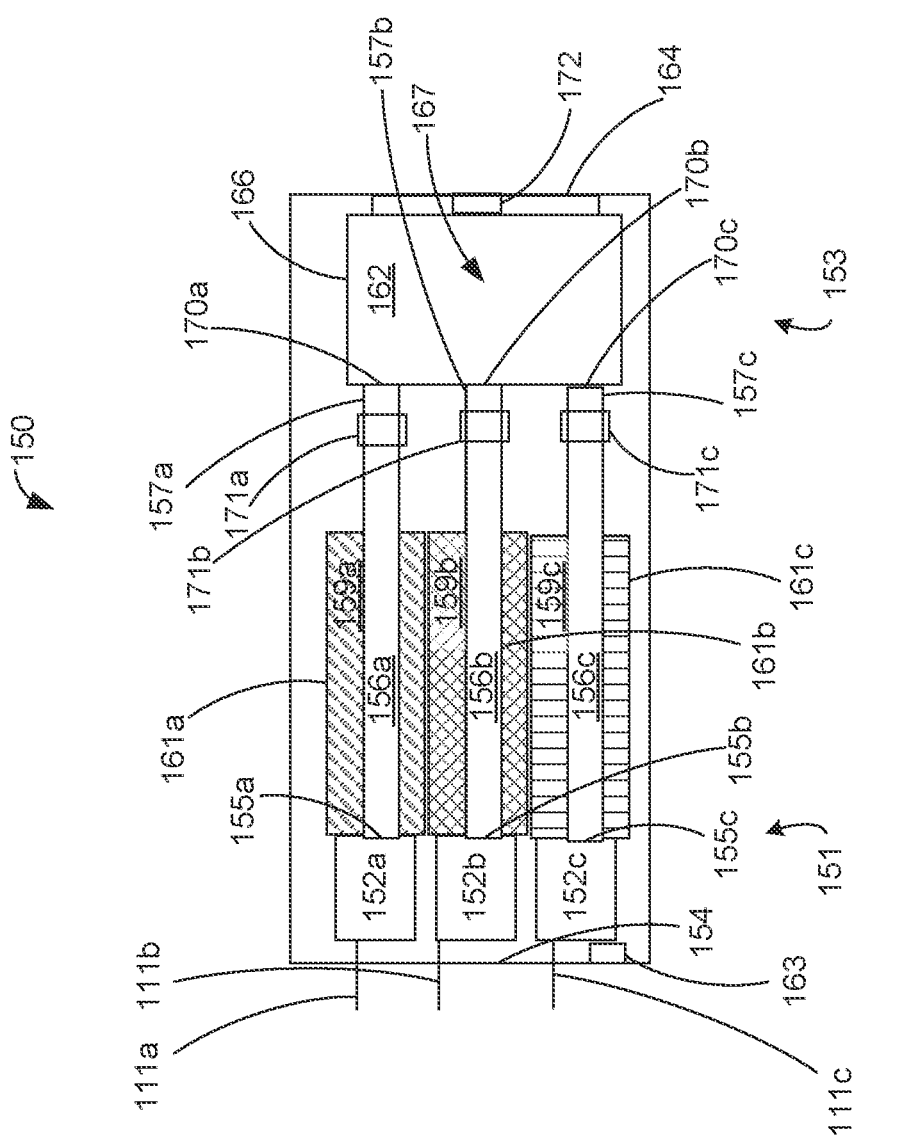
FIG. 3C is a schematic of the aerosolizer system of the cessation system illustrated in FIG. 3A.

The delivery device 109 and the pod 150 are configured to be coupled together, such that the delivery device 109 can provide control signals to the pod 150 and control aerosolizers in the pod 150 to generate an aerosol mixture in accordance with the treatment program. An example of a delivery device 109 and an aerosolizer pod 150 having three aerosolizers is illustrated in FIGS. 3A-3C. The delivery device 109 can include structure and a variety of sensors and components that are used to monitor use of the cessation device and implement the treatment program including revisions to the cessation program when needed. In an example, a delivery device 109 can include a housing having a distal end and a proximal end, a channel having an opening on a portion of the housing (e.g., a distal end of the housing or in a center portion of the housing) for receiving air. the cessation device can also have an opening on a proximal end of the channel to communicate air to an aerosolizer pod coupled to the housing.

The delivery device 109 can also include an aperture (e.g., on the proximal end of the housing) configured to receive an aerosolizer pod therein (e.g., pod 150 FIG. 2). The housing can be configured to at least partially surround the pod when the pod in positioned in the housing. The cessation device can include a plurality of sensors. The sensors can include, for example, one or more of a flow sensor positioned to sense air flowing through the channel, one or more density sensors for sensing density of aerosol generated by one or more aerosolizers, one or more temperature sensors configured to sense a temperature of aerosol generated by the one or more aerosolizers (respectively), an ambient temperature sensor, an ambient pressure sensor, a fingerprint sensor, a carbon dioxide sensor, and/or an oxygen sensor.

The delivery system 100 can also include a plurality aerosolizer driver ("driver") configured to electrically couple to and drive aerosolizers in a pod. In some embodiments, the delivery system 100 includes two or more drivers to control two or more aerosolizers in a pod. In some embodiments, the delivery system 100 includes three drivers to control three aerosolizers in a pod. In some embodiments, the delivery device 100 includes four or more drivers to control four or more aerosolizers in a pod. A controller circuit of the delivery system 100 can include a hardware controller coupled to the flow sensor, other sensors, the aerosolizer drivers, the rescue button and the fingerprint sensor. The hardware controller can include a hardware processor and a non-transitory computer readable medium in communication with the hardware controller, the computer readable medium configured to store smoking cessation program information, and to store executable instructions that, when executed, configure the hardware controller to perform a smoking cessation program that includes receiving input signals from the flow sensor, other sensors, and the rescue button, and individually controlling the aerosolizer drivers to provide aerosolizer generation signals to control the multiple aerosolizers of the aerosolizer pod to generate an aerosol mixture based at least on the received input signals and the smoking cessation program information. These, and other components, are described in more detail below, for example, in FIGS. 2-5. FIG. 1 illustrates a simplified view of the treatment system 10 that includes only one delivery system 100 associated with one user 30. In operation, the system 10 can include a plurality of delivery systems 100 each associated with a different user, and the server 25 can include a treatment program that is configured to control each of the plurality of delivery systems in accordance with its associated user their individual treatment program.

Sensor(s) 17 can be optionally included in the system. Sensor 17 can include one or more sensors that sense a characteristic of the user, and communicates information of the sensed characteristic to the delivery system 100 and/or the user device 15. In various embodiments, the sensor 17 can include a patch, a wearable, or any other sensor that can sense a characteristic of the user. As a non-limiting example, the sensor may be configured to sense a characteristic in the blood, sweat, urine, or saliva of the user (e.g., sugar level, nicotine level, pH, level of a drug/medicant/hormone, and the like).

FIG. 2 is a schematic of an example a delivery device 109 and an aerosolizer system (or "pod") 150 that can be used in the cessation system 10. As described in more detail in reference to FIG. 3A, the delivery device 109 includes components to perform a treatment program including components to control multiple aerosolizers in the pod 150 to generate an aerosol mixture in accordance with the treatment program, which is then inhaled by a user. The pod 150 is configured to be removably coupled to the delivery device 109. The pod 150 can be a consumable item. During a treatment program, a series of pods maybe provided to the user to in the delivery device. Each of the pods can include a substance, or multiple substances. As dictated by the treatment program, the substances in the series of pods provided to the user may be the same in each of the pods, in some of the pods, or in none of the pods.

In this example, the pod 109 is at least partially inserted into the delivery device 109 to couple them together. Also in this example, when the pod 150 is coupled to the delivery device 109, the aerosolizer drivers in the delivery device electrically connect to corresponding aerosolizers in the pod 109. The aerosolizer drivers 110 (FIG. 3A) can independently and separately provide signals to each aerosolizer 152 in the pod 109, and in this way generate desired aerosol mixtures of the different substances in the multiple aerosolizers of the pod 150 in accordance with the cessation program. For example, the aerosolizers 110 can be independently controlled to generate an aerosol mixture having various portions (e.g., percentages) of the various substances in the three containers 159 (FIG. 3A) of the pod 150. Also, the aerosolizers 152 can each be independently controlled to generate an aerosol having different droplet sizes. Other configurations are possible. For example, in some embodiments, the aerosolizers can be part of the delivery system 100, the pod includes containers of substances, and when the pod is inserted into the delivery device the substance in each pod is provided to a corresponding aerosolizer in the delivery device.

The delivery device 109 includes a distal end 105 having an opening 106 for receiving ambient air into the delivery device 109. The delivery device 109 is configured with one or more air communication channels such that air received through the opening 106 is provided to the pod 150. The pod 109 also can includes one or more air communication channels to provide air to each aerosolizer in the pod 150. The delivery device 109 includes a second opening 105 in the housing 102 which is configured to receive the pod 150 such that at least a portion of the pod 150 is positioned within the housing 102 in his coupled to the housing 109. The pod 150 includes an opening 154 on a distal end 151 through which to receive air passing through the delivery device 109. The pod 150 further includes, on its distal end 153, an opening 164 for providing an aerosol mixture to a user. Examples of certain components that can be included in the delivery device 109 and the pod 150 are illustrated in FIGS. 3A-3C, 4, and 5.

Figure 3D:
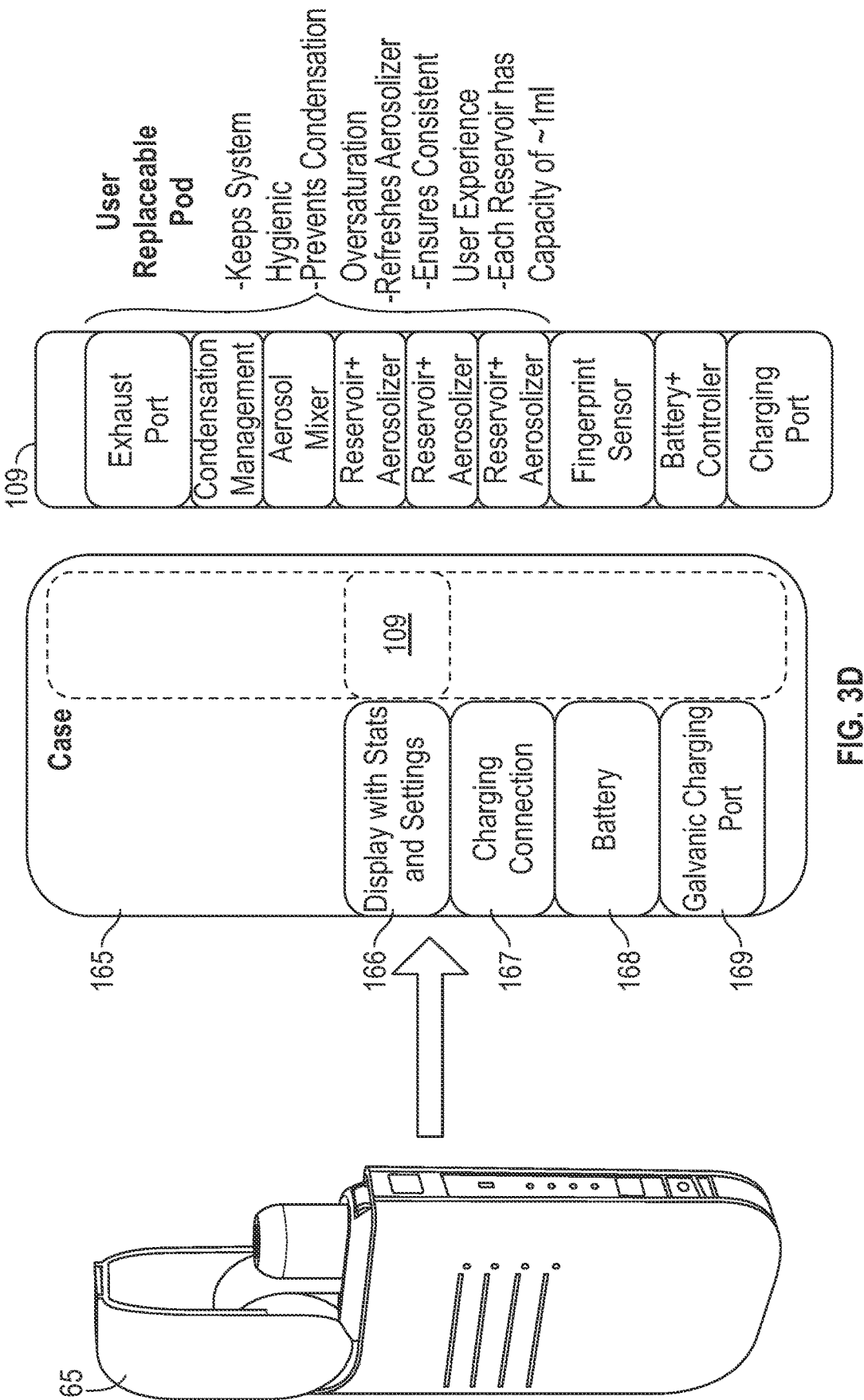
FIG. 3D is a schematic of the case and the cessation device containing the components illustrated in FIG. 3A.

An example of a delivery device 109 and a pod 150 that is coupled to the delivery device 109 and used as the delivery system 100 in the cessation system 10 are illustrated in FIGS. 3A-3D. Specifically, FIG. 3A illustrates an example of the delivery device 109, with the pod 150 inserted into and coupled to the delivery device 109. FIG. 3B further illustrates the delivery device 109 shown in FIG. 3A. FIG. 3C further illustrates the pod 150 of the shown in FIG. 3A. FIG. 3D illustrates a case 165 that can be used to house the delivery device 109 and pod 150. In various embodiments, the case 165 can include one or more additional components for facilitating use of the delivery device 109. Referring to FIG. 3A, in this example, the entire pod 150 is positioned within the housing 102 when the pod 150 is coupled to the delivery device 109. In other examples, a portion of the pod 150 may from the proximal end 103 of the delivery device 109 when the pod 150 is coupled to the delivery device 109. In this example, the pod 150 is coupled to the delivery device 109 such that it is in electrical communication with the delivery device 109 and in fluid communication with air flow into and through the housing 102 (e.g., through opening 106, through channel 104, and through opening 108).

A number of components and structures can be positioned within the housing 102 of the delivery device 109, for example but not limited to those illustrated in FIGS. 3A and 4. In this example, the delivery device 109 includes a channel 104 for providing ambient air to the pod 150, the channel having a distal end 122 at the distal end 101 of the housing 102. The channel extends from the opening 106 towards a proximal end 107 of the channel to opening 108. When the pod 150 is in the housing 102, an intake 154 of the pod 150 is aligned with the opening 108 such that air is communicated through the channel 104 to the pod 150. In other examples, instead of a single opening 106, the delivery device 109 may include one or more openings 106 and/or one or more channels 104 to receive air into the housing 102 and communicate the air to the pod 150. In some embodiments, the opening 106 may be located at a different portion of the housing instead of at the distal end 101. In an example, the housing may include one or more openings 106 on a side surface of the housing 102 instead of, or in addition to, the distal end 101. In some embodiments, one or more openings 106 are located in a gap, or near a gap, between the housing 102 and the pod 150. The delivery device 109 also includes an opening 105, in the housing 102 on the proximal end 103 of the delivery device 109, which is structured to allow the pod 150 to be placed into the housing 102 through the opening 105. In this example, the delivery device 109 includes a cavity 140 which extends from the proximal end 103 of the housing 102 into the housing 102. The cavity 140 and walls of the housing 102 surrounding the cavity are structured to receive and hold the pod 150.

The delivery device 109 also includes a controller circuit 130 which is connected to a power source 114. The controller circuit 130 can include one of more hardware processors and non-transitory computer readable medium, for example, as described in reference to FIG. 5. The power source 114 can include, for example, a battery, capacitor, super-capacitors, or another energy storage medium, or a combination thereof. The power source 114 can be configured to provide electrical power to the pod 150 when the pod 150 is coupled into the delivery device 109. In some examples, the pod 150 also includes a power source. The controller circuit 130 is in communication with one or more sensors to receive information (e.g., signals) from the sensors that the controller circuit 130 can use (at least in part) to operate a treatment program. For example, the delivery device 109 can include a flow sensor 112 which is positioned and configured to sense airflow into the delivery device 109 through the channel 104. The controller circuit 130 is connected to the flow sensor 112 and receives information indicative of the of air passing through the channel 104 from the flow sensor 112. Based on information from the flow sensor 112, the controller circuit 130 can determine information indicating the use of the cessation system by a user. For example, a "puff" (an inhalation of air/aerosol from the cessation system by a user) frequency, a puff duration, and/or a puff amount, can be determined by the controller circuit 130 based on information from the flow sensor 112. A puff profile can also be determined by the controller circuit 130 based on information from the flow sensor 112. The "puff profile" at least in part refers to how changes in the air flow during the duration of a puff. For example, whether the profile (e.g., airflow as a function of time) of the puff is a square wave, trapezoidal-shaped, sinusoidal-shaped, and the like). The determined puff frequency, puff duration, puff amount, and/or the puff profile can be used by the cessation program to dynamically tailor the cessation program to a particular user's needs. Any signals/information the controller circuit 130 receives can be communicated one or more of the user device 15 and the server 25, and used to monitor the user's progress in the cessation program, and used to modify the cessation program.

In this example, the delivery device 109 is configured to be used with a pod 150 that has three aerosolizer units ("aerosolizers") 161 (as shown in the example in FIG. 3C. Each aerosolizer 161a-c can generate an aerosol from a substance contained in the pod 150. In this example, each aerosolizer 161a-c includes a heating element 152a-c (e.g., a resistive heating element) that can be controlled by the controller circuit 130 via the aerosolizer drivers 110a-c to produce aerosol in accordance with the cessation program. The aerosol is communicated via passages 156A-c and enters the mixing chamber 162 through the mixing chamber intake openings 170a-c (FIG. 3C), where it forms an aerosol mixture which can be inhaled by a user. Each aerosolizer driver 110a-c can interact with a corresponding aerosolizer 161a-c to cause it to produce some or all of the aerosol mixture such that the aerosol mixture can include any proportion of a plurality of substances in the aerosolizers. In some embodiments, a temperature value is determined by the controller circuit 130 for each aerosolizer 161 by using the heating element 152 as a temperature sensor. For example, by sensing a change in a resistance (or impedance) value of the heating element as the temperature of the heating element 152 increases and correlating the resistance value to a temperature. Other embodiments may sense the temperature of an aerosolizer in different ways. For example, in some embodiments, the delivery device 109 can include temperature sensors 158*a-c* (shown in dashed lines) that are configured to sense the temperature of aerosol generated by the three aerosolizers 161*a-c* of the pod 150. The temperature sensors 158*a-c* can be positioned in the delivery device 109 such that when the pod 150 is coupled to the delivery device 109, each temperature sensor 158*a-c* is adjacent to one of the passages 156*a-c* that communicate aerosol from heating elements 152*a-c* to the mixing chamber 162 of the pod 150. The delivery device 109 can also include density sensors 160*a-c* that are configured to sense the density of aerosol generated by the three aerosolizers 161 of the pod 150. The density sensors 160*a-c* can be positioned on the delivery device 109 such that when the pod 150 is coupled to the delivery device 109, each density sensor 160*a-c* is positioned adjacent to one of the passages 156*a-c* that communicate aerosol from heating elements 152*a-c* of the pod 150 to the mixing chamber 162 of the pod 150. In some embodiments, the density sensors 160*a-c* can be optical sensors.

The delivery device 109 can also include a fingerprint sensor 118 which is connected to the controller circuit 130 and is used to sense a user's fingerprint to unlock the delivery device 109. In addition, the delivery device 109 can include an ambient temperature sensor 405 in ambient pressure sensor 407, in the controller circuit 130 can be configured to use information from the ambient temperature sensor 405 in the ambient pressure sensor 407 to control the cessation program provided to the user. For example, to control the aerosol mixture generated by pod 150 based at least in part on the ambient temperature and/or the ambient pressure.

In some examples, the delivery device 109 optionally also includes a carbon dioxide sensor 121 that is coupled to the controller circuit 130 and provides a signal to the controller circuit 130 indicative of an amount of carbon dioxide. The delivery device 109 can also include a control (e.g., a button, or fingerprint sensor 116) to activate the carbon dioxide sensor 121. In operation, after activating the sensor, a user exhales into the opening 106 to provide a flow of air to the carbon dioxide sensor 121 which provides a signal to the controller circuit 130. The information from the carbon dioxide sensor 121 can be used to determine a carbon dioxide level of the user and used in the cessation program, for example, to modify the cessation program.

In some examples, the delivery device 109 optionally also includes a blood oxygen sensor 119 that is coupled to the controller circuit 130 and provides a signal to the controller circuit 130 indicative of an amount of oxygen in the blood. In an example, the blood oxygen sensor 119 can be a pulse oximetry sensor. In some examples, the blood oxygen sensor 119 can be incorporated into the fingerprint sensor 116. In some embodiments, the blood oxygen sensor 119 can be separate from the fingerprint sensor 116.

The delivery device 109 can also include a pod ID chip interface 465, which can be positioned near the cavity 140 that receives the pod 150. A pod 150 configured to be used with the delivery device 109 can include a pod ID chip 163. In some embodiments, the pod ID chip 163 can be positioned on a portion of the pod 150 such that when the pod 150 placed into the delivery device 109, the pod ID chip interface 465 physically and/or electronically aligns with pod ID chip 163 such that information may be communicated from the pod ID chip 163 to the pod ID chip interface

465. The information can relate to one or more aspects of the configuration of the pod 150. In an example, the information can relate to one or more of the substances in the aerosolizer's of the pod 109 (e.g., type of substance, amount of substance left). In another example, the information can relate to a pod ID which the delivery device 109 can compare to stored data to determine information relating to the pod 109 (e.g., information related to the aerosolizers 152) that the delivery device 109 may use to properly provide the desired aerosol mixture to a user.

In this example, the delivery device 109 also includes a "rescue" button 116 which can be activated to provide a user an additional (or "rescue") dose of one or more of the substances in the pod 150, for example, an additional nicotine dose in a smoking cessation program. When the rescue button 116 is used, the controller circuit 130 saves information relating to its use (e.g., date/time information of each use). The rescue button use information can be used by the delivery system to modify the cessation program. In some examples, the rescue button use information is communicated by the delivery device 109 to the user device 15 and/or the server 25, and used to track the user's progress in the cessation program and/or dynamically modify the cessation program as a result of the user needing a rescue dose. Modifications made to the cessation program, based on actuation of the rescue button 116 can be communicated from the server system 25 to the user device 15, and then communicated to the delivery device 109 from the user device 15. The delivery device 109 can include one or more other features, including an antenna 120, and communication circuitry in the controller 130, or implemented in a separate hardware component in communication with the controller 130, that allows the delivery device 109 to communicate with the user device 15 or to another computer device either directly or indirectly via a network. Certain features of the controller circuit 130, or components of the delivery device 109 that are in communication with the controller circuit 130, are further illustrated in FIGS. 4 and 5.

Figure 5:
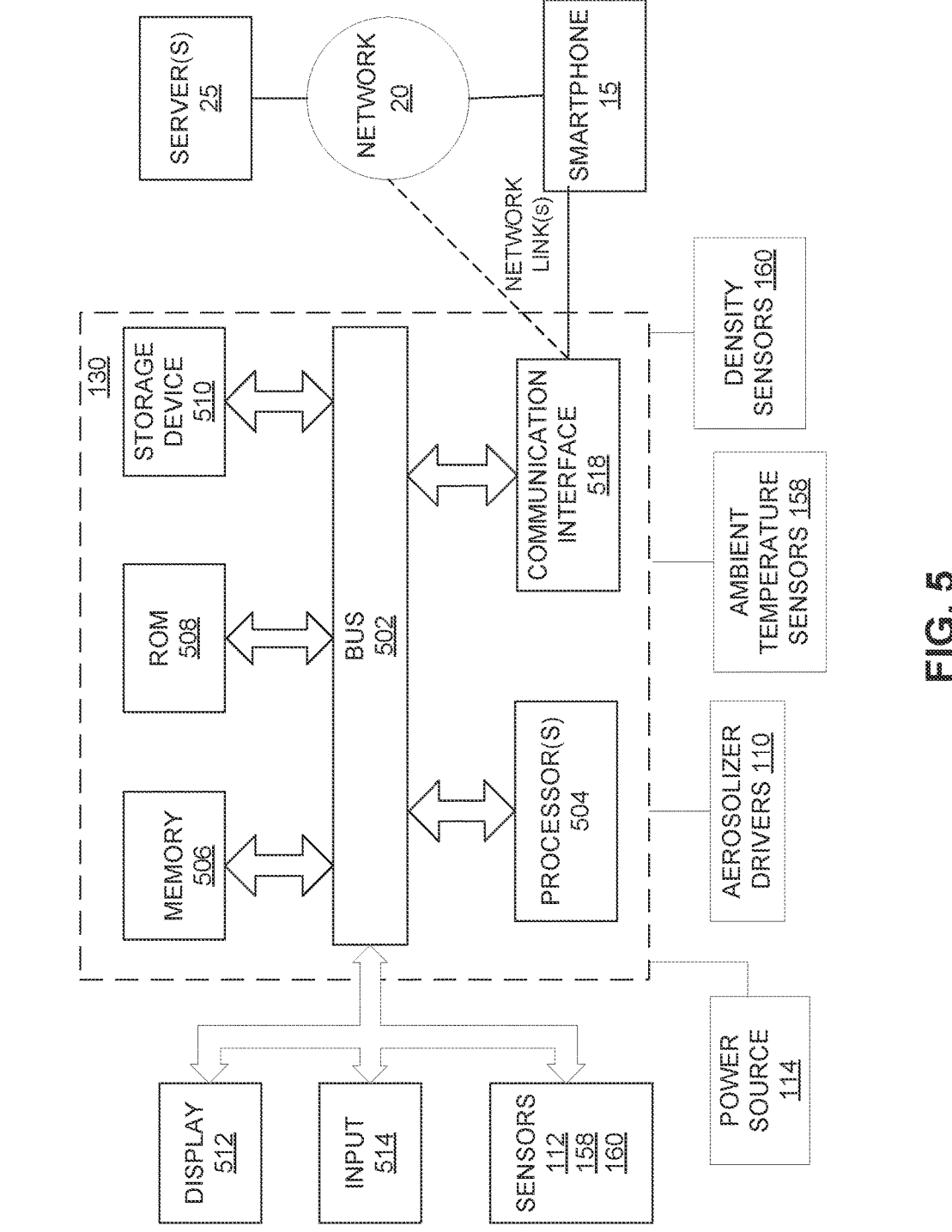
FIG. 5 is an example of a computer system that may be used to implement the functionality described herein.

As described in further detail in reference FIG. 5, the controller circuit 130 includes one or more hardware processors 504 in communication with at least one non-transitory memory component 506, 508 that includes executable instructions that configure the one or more hardware processors 504 to run a treatment program. The delivery device 109 includes an aerosolizer driver 110*a-c* that corresponds to each of the aerosolizers 161 in the pod 150. The controller circuit 130 is connected to the aerosolizer drivers 110*a-c* and controls the aerosolizer drivers 110*a-c* to operate the respective aerosolizers 161*a-c* to generate aerosol such that a desired aerosol mixture reduced by the aerosolizer system provided to a user, as prescribed by the cessation program. For example, the controller circuit 130 can control the aerosolizers 161*a-c*, via the aerosolizer drivers 110*a-c*, to each generate a certain amount of aerosol from a substance (a fluidic mixture of nicotine) that in each aerosolizer 161*a-c*, such that the aerosol from each of the aerosolizers 161*a-c* is combined in the aerosol mixing chamber 162 of the pod 150 forming a desired aerosol mixture is provided to a user.

The controller circuit 130 can also independently control the aerosolizers 161*a-c*, via the aerosolizer drivers 110*a-c*, to affect the aerosol droplet size (ADS) in the aerosol generated by each of the aerosolizers 161*a-c*. The ADS of an aerosolized substance can determine where it will be absorbed in the user. Smaller ADS's generally travel to and are absorbed in the lungs, and larger ADS's generally travel to and are absorbed in the mouth or throat. The controller circuit 130 can independently control the aerosolizers 161*a-c*, via the aerosolizer drivers 110*a-c*, to produce ADS's of different sizes based on the treatment program. For example, depending on what portion or stage of a treatment program the user is in (for example, as illustrated in FIG. 10H). In some embodiments, the aerosol droplet diameters will be less than or equal to 20 μm. In some embodiments, the aerosol droplet diameters will be less than or equal to 10 μm. In some embodiments, the aerosol droplet diameters will be less than 1 μm, or equal to 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, or 20 μm, plus or minus 0.5 μm. In some embodiments, aerosol droplet diameters will be less than or equal to 1 μm (at least for a portion of the treatment program). In some embodiments, aerosol droplet diameters will be greater than or equal to 10 μm (at least for a portion of the treatment program). In some embodiments, aerosol droplet diameters for one portion of the treatment program can be less than or equal to 3 μm and for another portion of the treatment program are greater than or equal to 8 μm. In some embodiments, the aerosol droplet diameters for one portion of the treatment program can be less than or equal to 1 μm and for another portion of the treatment program are greater than or equal to 10 μm. Practically speaking, when the aerosolizers are controlled to generate a certain aerosol droplet diameter, the aerosol droplet diameters may have a range of diameters but are mostly of the target diameter such that the deposition site of the aerosol is effectively the target deposition site (e.g., the mouth, lungs, etc.). Accordingly, when referring to certain aerosol diameters, this is understood to indicating that an effective amount of aerosol droplets are generated of the specified diameter. In an example, more than 30%, 40%, 50%, 60%, 70%, 80%, 90%, or 95% of the aerosol has the specified diameter. In another example, more than 50%, 60%, 70%, 80%, 90%, or 95% of the aerosol has the specified diameter. In an example, more than 70%, 80%, 90%, or 95% of the aerosol has the specified diameter.

As illustrated in the example of FIG. 3C, the pod 150 includes three aerosolizers 161*a-c*. Electrical connections 111*a-c* are connected to one of the aerosolizers 161*a-c* respectively, and can provide electrical power and/or control information to the aerosolizers 161*a-c*. When the pod 150 is coupled to the delivery device 109, the electrical connections 111*a-c* are coupled to the aerosolizer drivers 110*c-c* respectively. In some embodiments that include thermal aerosolizers 161. Control of the operation of the aerosolizers is achieved by changing the electrical power supplied by the aerosolizer drivers 110, to each heating element 152 of each aerosolizer 161, via the electrical connections 111. The controller circuit 130 can individually control the multiple aerosolizer drivers 110 to supply the electrical power, and correspondingly, can individually control each aerosolizer to produce a certain amount of aerosol and to produce aerosol with a desired droplet size, according to the smoking cessation treatment program. Each thermal aerosolizer 161 can include a heating element 152, a container 159 that is configured to hold a substance (e.g., a fluid containing nicotine for the smoking cessation example), and a passage 156. In an example of the fluids that can be in the containers 159, in an example, a first container 159*a* contains a fluid comprising monoprotonated nicotine. In an example, a second container 159*b* contains a fluid comprising freebase nicotine. In an example, a third container includes a fluid comprising another medicant, a flavored substance (flavorant), or a non-nicotine placebo.

In an example, the three containers 159*a-c* contain 2.5 mL of liquid comprising 5% flavor system, and a propylene glycol (PG) and glycerin (G) mix, in a 60:40 PG:G ratio. In addition, container 159*a* contains 60 mg/mL synthetic nicotine plus a pH adjuster to create a pH of 4.0 thus ensuring that the species in this container 159*a* is monoprotonated nicotine. Container 159*b* contains 60 mg/mL synthetic nicotine at pH 10.0 thus ensuring that the nicotine species in this container 159*b* is freebase nicotine. 5% of container 159*c*'s volume is flavor system, and the remainder is a PG:G in the ratio 60:40. Container 159*c* contains no nicotine. In various examples, the precise ratio of PG:G, the amount of flavor system, the amount of pH adjuster, the final dosage algorithm settings, and the aerosolization power settings, can be different, and may be based on characterization of the actual aerosolizer components that are used in an implementation. A number of factors can affect aerosol delivered to the user including, but not limited to, micro-aerodynamics of droplet collision and condensation change what aerosol exits the mouthpiece. Information relating to these factors can be determined during bench-testing, and then used to calibrate a delivery device 109 based on the aerosolizers and the pod design. Correspondingly, the algorithms can be adjusted to ensure that the aerosol mixture delivered to the user is according to the treatment program across the full aerosol parameter ranges in a quit journey treatment program, for example, the quit journey program illustrated in FIG. 7Q.

Different aerosol droplet sizes are achieved by changing the power that is supplied to the surface electrodes. In principle any porous material can be used with a conductive electrode—earlier generations used cotton wicks with electrode coils surrounding them. In an example of a thermal aerosolizer, each aerosolizer can use of a ceramic wick and a surface electrode to permit more precise aerosolization. As an example, the amount of aerosol produced by each aerosolizer 161 can be controlled by the duration the aerosolizer is supplied electrical power such that a thermal component of the aerosolizer reaches a temperature sufficient to generate an aerosol from the liquid in the respective container of the aerosolizer. As an example, the size of the aerosol produced by each aerosolizer 161 can be controlled by the amount of power the aerosolizer is supplied electrical power, changing the temperature of the thermal component which can correspondingly cause generation of aerosol of different droplet sizes.

Each passage 156 includes a distal end 155 closest to the aerosolizer 159 and a proximal end 157 adjacent to the mixing chamber 162. The passage 156 provides a flowpath for aerosol generated by the heating element 152 to flow to the mixing chamber 162. The mixing chamber 162 includes walls 166 which enclose a mixing space 167. In the mixing chamber 162, the individual aerosols generated by each of the aerosolizers 161*a-c* mixes together and forms an aerosol mixture, which a user can inhale (ingest) through opening 164. In this example, power for the heating elements 152 is provided by the delivery device 109 via the connections 111. In some embodiments, the pod 150 includes one or more power sources that can provide electrical power to the heating elements 152, or provide power to other electrical components of the pod 150. The controller circuit 130 can control the aerosolizers 161 to generate an aerosol mixture of a certain total nicotine concentration by controlling the aerosol generated by each of the aerosolizers 161 in accordance with the treatment program.

The controller circuit 130 can be configured by treatment program information (e.g., algorithms) the delivery device 109 has coded in its firmware and/or that it receives to drive the aerosolizers to produce the desired aerosol amount and droplet diameter size from each of the aerosolizers (e.g., the three aerosolizers). The process begins with the target delivery parameters for a puff on the nth day of the Quit Journey. These parameters inform a dosage algorithm that determines how much liquid is required from each of the three containers 159*a-c*. Then, given the known microfluidic performance of the wick system of the aerosolizers that are implemented in the delivery device 109, a mass conversion algorithm determines how much energy must be delivered to each aerosolization electrode to achieve this. One or more sensors in the delivery device 109 (e.g., the flow sensor 112) determine the topography of the patient's puff, and from this data the algorithm ensures that the correct proportion of the fluid in containers 159*a*, 159*b*, and 159*c* is aerosolized, and that energy is provided to the electrodes for the duration of the puff to achieve the desired aerosol mixture. The aerosolization "drivers" can incorporate data that adjusts parameters to account for condensation losses in the aerodynamic channel before mouthpiece exit, and for the aggregation of aerosol droplets in this channel (for example, based on previously determined test data and/or based on one or more sensors in the delivery device, e.g., an ambient temperature sensor) thus ensuring that the aerosol droplet size at mouthpiece exit is what is expected. The pod 150 can optionally include a sensor 172 positioned on or near the exhaust port 164 that can sense a characteristic of a user when the user is using the delivery system 100. Specifically, when the sensor 172 is in contact with, or is adjacent to or near, the user's mouth. In some examples, the sensor 172 is configured to sense a characteristic of the user's saliva or the user's breath. The sensor 172 can include a hardware processor and other hardware components (e.g., sensor, transceiver, antenna, etc.) to sense the characteristic and communicate information about the sensed characteristic to the delivery device 109 (for subsequent communication to the user device 15) or to the user device 15.

Control of the aerosolizes 161 can be based on the smoking treatment program and based on inputs received from one or more of the sensors (e.g., the flow sensor). Nicotine in e-liquids can exist in two forms: free base (meaning free from protons), and monoprotonated (meaning has one proton, also called a "salt"). There is a correlation between the pH level of the liquid and the ratio between the two forms. A common way to control the pH levels (and free base ratio) in the liquid is by using an organic acid in certain amounts to adjust the pH. In some embodiments, the total nicotine concentration delivered in the aerosol can range from 0 to 58 mg/mL. This total concentration is the sum of monoprotonated nicotine concentration, $[NicH^+]$, and free-base nicotine concentration $[Nic]$. Note that nicotine can also exist in a di-protonated state, but this is practically never reached in tobacco aerosols because conditions in the aerosol droplets are not sufficiently acidic.

The free nicotine ratio ("FNR") can be calculated as:

$$FNR=[Nic]/([Nic]+[NicH^+])$$

$$FNR=1/(1+10^{-pH}/K_a)$$

where $K_a$ is the acidity constant for NicEt which is 8.01. So given a target FNR, the controller circuit 130 (e.g., firmware in the hardware processor of the controller circuit 130) may determine the required pH, and the microfluidics mix the high and low pH solutions (which contain exactly the same total nicotine concentration) to achieve the target pH thereby ensuring that the FNR is the value required by the treatment program.

An embodiment of a portable charging case 165 is illustrated in FIG. 3D. The delivery device 109 can be stored and charged within the portable charging case 165. In this embodiment, the case 165 includes a display 166 for the user to observe both statistics and settings to which the system is set. The case 165 houses and can be powered by a rechargeable power source, for example, battery 168, which can be accessed via a charging port 169 located on the case 165, the charging port 169 configured to receive a mating plug connector to charge the battery 168. When the delivery device 109 is not in use, it can be stored in a cavity within the case 165. In some implementations, power source 114 of the delivery device can be charged from the battery 168 through a wired or wireless connection.

FIG. 4 is a schematic of an example of a circuit 113 that can be used in a delivery device, for example, the delivery device 109 illustrated in FIGS. 1 and 3A. As illustrated in FIG. 4 communication lines can connect the controller circuit 130 and other components of the delivery device to form the circuit 113. The controller circuit 130 can include one or more hardware processors (e.g., hardware processors 504, FIG. 5). An airflow is created when a user sucks in air through the delivery device. In this schematic, the airflow is generally from left to right such that intake of air is sensed by the flow sensor 112 and is received by the aerosolizers 161. The aerosolizers 161 generate aerosol in the airflow, and the airflow then may (in some embodiments) pass by sensors (e.g., temperature sensor 158 and/or density sensor 160), into a mixing chamber, and then out of the pod to the user's mouth. FIG. 4 illustrates many components that are illustrated in FIG. 3A-3C, and also illustrates some additional components. For example, in this embodiment, a flash memory 410 is in communication with the controller circuit 130. The controller circuit 130 can include a transceiver or other communication circuitry that is coupled to an antenna 120 which allows the delivery device 109 to communicate with a smart phone, another device, or a network. As illustrated in FIG. 4, the circuit 113 can also include a pod ID chip interface 465. In such embodiments, when the pod 150 is coupled to the delivery device 109, the pod ID chip interface 465 is in communication with a pod ID chip 163 of the pod 150 for communicating information between the pod and the delivery device. The circuit 113 can also include a case data interface 425 which is in communication the controller circuit 130, and a case charge interface 430 which is in communication with a battery manager 420 which manages power provided to the controller circuit 130 from a power source (e.g., battery) 114 to, for example, manage the charging of the battery 114 by a case or another power source.

FIG. 5 is an example of a computer system 500 that may be used to implement the functionality described herein for a treatment system, e.g., a delivery device, a user device, and/or a server system. In some embodiments, the computer system 500 can be characterized as including all electrical and electronic components of the treatment system. In some embodiments, the computer system 500 can be characterized as being the system illustrated in FIG. 1. In this particular example, the computer system 500 is described broadly as including the controller circuit 130 in a delivery device 109, and other components are in communication with the controller circuit 130. However, nothing in this description is intended to limit the computer system 500 to be interpreted as referring to only the controller circuit 130 and its components.

The controller circuit 130 can include a bus 502 or other communication mechanism for communicating information between components of a cessation system, and a hardware processor, or multiple processors, 504 coupled with bus 502 for processing information. Hardware processor(s) 504 may be, for example, one or more general purpose microprocessors. The hardware processor(s) 504 include non-transitory memory 505. In some examples, the functionality the components illustrated in the controller circuit 130 can be implemented in a single chip (e.g., an ASIC) and the classification policy is stored in memory and/or in circuitry, for example, memory 505.

Computer system 500 also includes a main memory 506, such as a random access memory (RAM), cache and/or other dynamic storage devices, coupled to bus 502 for storing information and instructions to be executed by processor 504. Main memory 506 also may be used for storing temporary variables or other intermediate information during execution of instructions to be executed by processor 504. Such instructions, when stored in storage media accessible to processor 504, including on memory 505 integrated on a processor chip, render computer system 500 into a special-purpose machine that is customized to perform the operations specified in the instructions for a smoking or cessation program. Computer system 500 further includes a read only memory (ROM) 508 or other static storage device coupled to bus 502 for storing static information and instructions for processor 504. A storage device 510, such as a magnetic disk, optical disk, or USB thumb drive (Flash drive), etc., is provided and coupled to bus 502 for storing information and instructions.

Computer system 500 may be coupled via bus 502 to a display 512, such as a LCD or liquid crystal display, and which may include a touchscreen, for displaying information to a network operator. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 504 and for controlling cursor movement on display 512 by a network operator.

Computing system 500 may include a user interface module to implement a GUI that may be stored in a mass storage device as computer executable program instructions that are executed by the computing device(s). Computer system 500 may, as described below, implement the techniques described herein using customized hard-wired logic, one or more ASICs or FPGAs, firmware and/or program logic which in combination with the computer system causes or programs computer system 500 to be a special-purpose machine. According to one embodiment, the techniques herein are performed by computer system 500 in response to processor(s) 504 executing one or more sequences of one or more computer readable program instructions contained in main memory 506. Such instructions may be read into main memory 506 from another storage medium, such as storage device 510. Execution of the sequences of instructions contained in main memory 506 causes processor(s) 504 to perform the process steps described herein. In alternative embodiments, hard-wired circuitry may be used in place of or in combination with software instructions.

Various forms of computer readable storage media may be involved in carrying one or more sequences of one or more computer readable program instructions to processor 504 for execution. The instructions can be for operating a cessation program using a user device 15 and/or a delivery system 100. For example, the instructions may initially be carried on a magnetic disk or solid state drive of a remote computer (for example, server 25). The remote computer can load the instructions into its dynamic memory and send the instructions over a network. A transceiver in the computer system 500 and place the data on bus 502. Bus 502 carries the data to main memory 506, from which processor 504 retrieves and executes the instructions. The instructions received by main memory 506 may optionally be stored on storage device 510 either before or after execution by processor 504.

Computer system 500 also includes a communication interface 518 coupled to bus 502. Communication interface 518 provides a two-way data communication coupling to a network link 520 that is connected to a network 20. For example, communication interface 518 may be an integrated services digital network (ISDN) card, cable modem, satellite modem, or a modem to provide a data communication connection to a corresponding type of telephone line. As another example, communication interface 518 may be a local area network (LAN) card to provide a data communication connection to a compatible LAN (or WAN component to communicated with a WAN). Wireless links may also be implemented. In any such implementation, communication interface 518 sends and receives electrical, electromagnetic or optical signals that carry digital data streams representing various types of information.

Network links typically provides data communication through one or more networks to other data devices. For example, the network link may provide a connection through a smartphone 15 to a server 25 via network 20. Computer system 500 can send messages and receive data, including program code, through the network(s), network links and communication interface 518. In an Internet example, a server 25 might transmit a requested code for an application program through network 20 and communication interface 518. The received code may be executed by processor 504 as it is received, and/or stored in storage device 510, or other non-volatile storage for later execution.

In various embodiments certain functionality may be accessible by a user through a web-based viewer (such as a web browser), or other suitable software program on the user device 15 or another computer. In such implementations, the user interface may be generated by the server system 25 and transmitted to the user device 15. Alternatively, data (e.g., user interface data) necessary for generating the user interface may be downloaded as a separate app to the user device 15. A user may then interact with the user interface on the user device 15 through the app to view information related to the treatment program and interact with the treatment program.

Figure 6A:
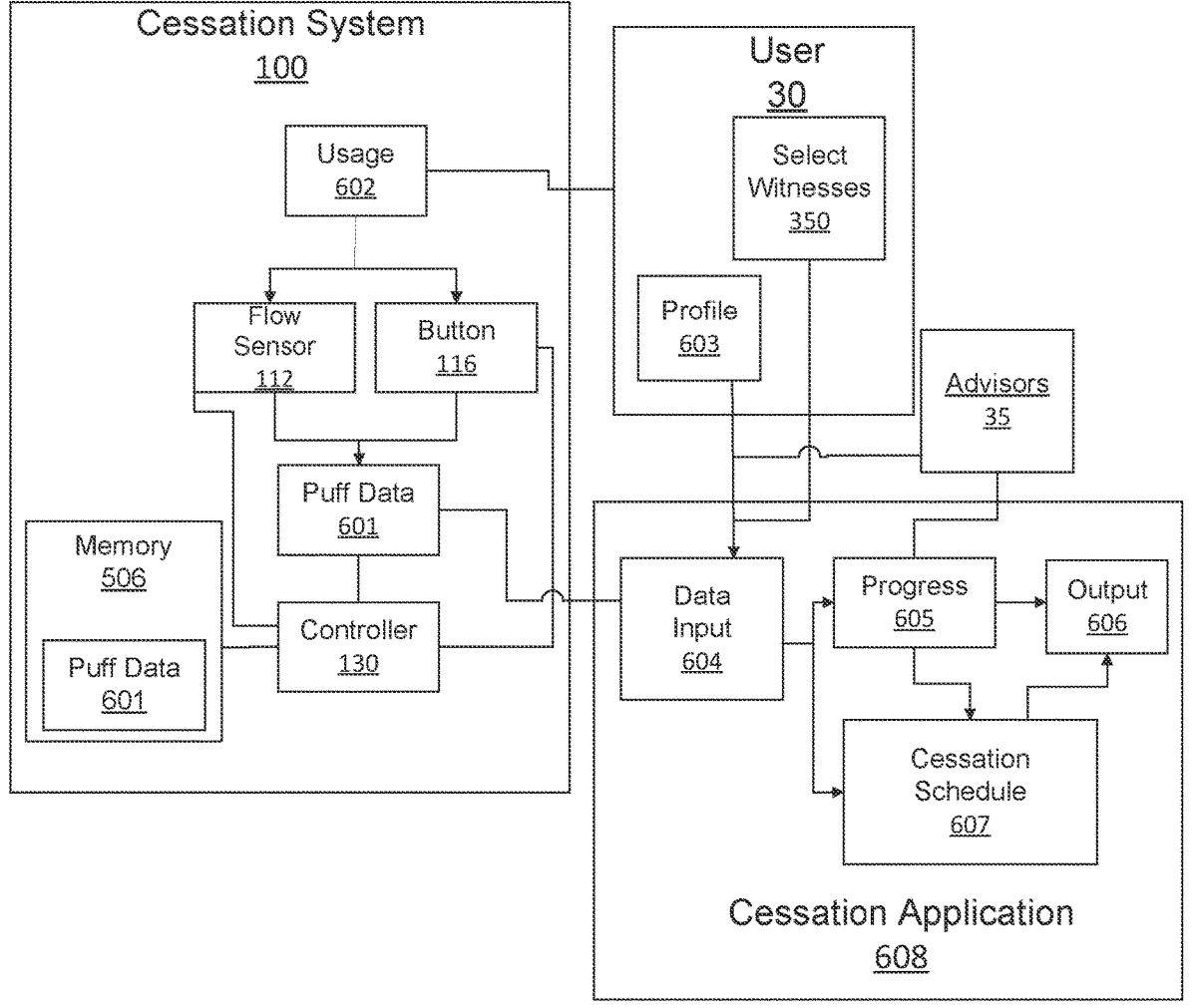
FIG. 6A is a diagram of a system for developing and implementing a smoking cessation program, according to one embodiment.

FIG. 6A is a diagram demonstrating an example of a high level data flow logic of a smoking cessation system. A new user 30 seeking to quit smoking may perform at least a portion of their onboarding using a cessation application 608. The cessation application 608 can be implemented on a user device (e.g., a smart phone, a mobile computer, a desktop computer, a specialized computer in a medical practitioner's facility, or another suitable computer resource). For example, user device 15 (FIG. 1). The cessation application 608 can include functionality that runs in-part on a portable computer, and functionality that runs in-part on a server system. As part of the onboarding, the user 30 may be prompted to enter their profile 603 into the cessation application 608. The profile 603 can include characteristics that are relevant to nicotine withdrawal. This may include age, sex, height, weight, smoking history, including the number of cigarettes per day, the time of day of usage, biological co-factors, psychosocial co-factors, clinical co-factors, and any other relevant characteristics.

For example, the application 608 may request the number of cigarettes smoked per day, the brand of cigarettes, whether the user 30 smokes e-cigarettes. If the user 30 indicates through the interface that they smoke e-cigarettes, the application 608 may additionally request the user provide how long each cartridge is used and the amount of nicotine per cartridge.

Other information may also be entered, including objective medical information determined from one or more tests of the user. For example, the nicotine metabolic rate (NMR) of the user. Once the data has been entered, the application 608 may determine treatment program/smoking cessation schedule 607 based on the user's 30 individual profile 603 and other provided information. That schedule may then be output 606 to the user 30 on an app on the user's device 15. The output 606 may be in the form of one or more charts, tables and/or other information related to the treatment program. The information may include an indication of the amount of cigarettes or puffs recommended for the user 30 for a particular period of time during the program. This may include the number of cigarettes recommended for the day, week, or month, with options to display different time periods. Additionally, the user 30 may be given different options to select the pace of withdrawal from different recommended paces, some being a much faster drop from nicotine use.

The user 30 may seek help from outside advisors 35, like a physician, to measure or calculate the information required for the profile 603. The advisor 35 may also play a role in monitoring the progress 605 of the cessation application 608 which could lead to changes in the program over use.

The cessation system 100 receives data from the cessation application 608 to deliver the intended dose to the user 30. The cessation system 100 also stores puff data 601, which may include puff duration, puff interval, and/or puff volume, in memory 506, to send via the controller circuit 130 back to the cessation application 608 and the treatment program on the server system 25. This puff data 601 may be monitored by the user 30 or the advisor 35, and the treatment program itself to determine adjustments for the cessation schedule 607.

Figure 6B:
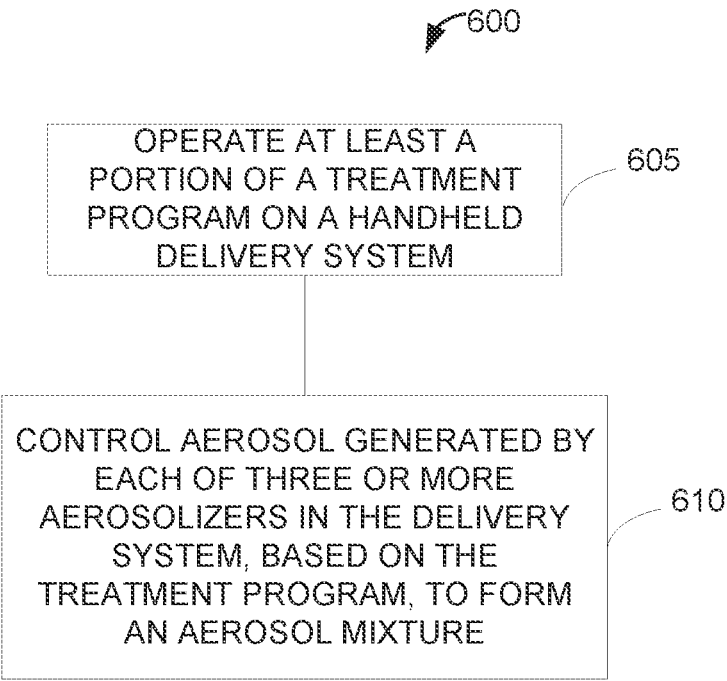
FIG. 6B is a flowchart illustrating an example of a smoking cessation process, according to one embodiment.

FIG. 6B is a flowchart illustrating an example of a cessation process 600, according to one embodiment. In an example, the cessation process 600 is for helping a user quit smoking. In another example, the cessation process 600 is for helping a user to quit vaping. In another example, the cessation process 600 is for helping a user to quit an addictive behavior. At block 605, the process 600 operates at least a portion of a treatment program on a handheld delivery system. In one example, the handheld delivery system is the delivery system 100 illustrated in FIG. 3A. At block 610, the process 600 independently controls the aerosol generated by each of three or more aerosolizers in the delivery system, based on the treatment program, to form an aerosol mixture. In another example, the process 600 can independently control the aerosol generated by each of two aerosolizers in a delivery system, based on the treatment program, to form an aerosol mixture. The aerosol mixture can then be inhaled by a user.

Figure 6C:
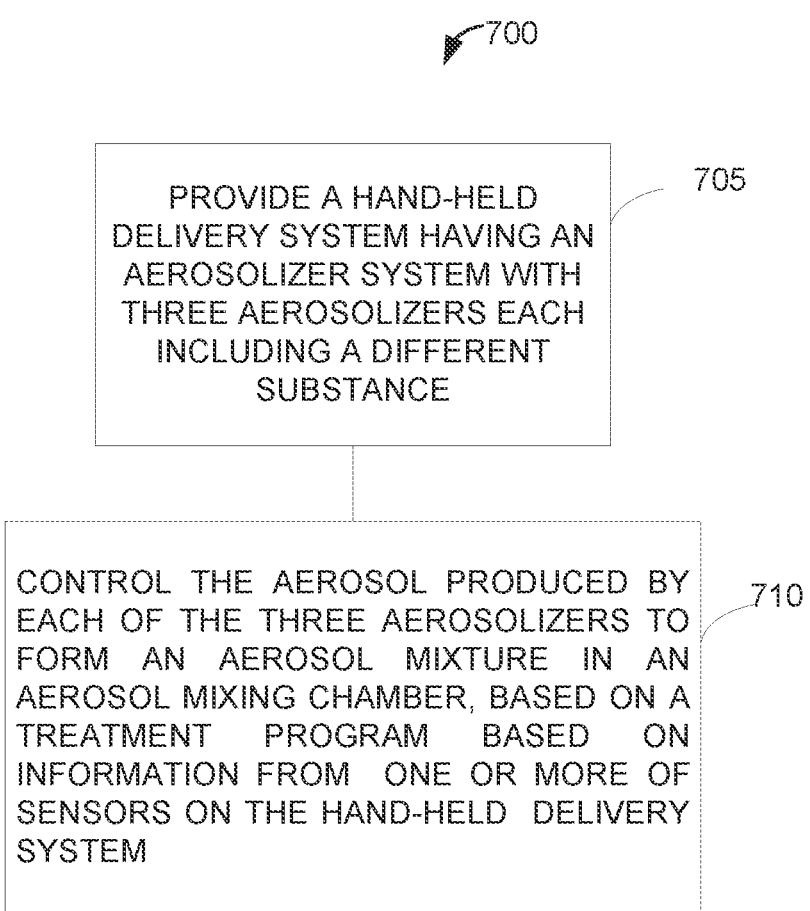
FIG. 6C is a flowchart illustrating another example of a smoking cessation process, according to one embodiment.

FIG. 6C is a flowchart illustrating another example of a treatment process 700, for example, for treating a smoking or vaping addiction. At block 705 the process 700 provides a hand-held drug delivery system, the delivery system having an aerosolizer system with three aerosolizers each including a different substance. In an example, the aerosolizer system is similar to aerosolizer system in pod 150 illustrated in FIG. 3C which has three aerosolizers. Even though this disclosure generally refers to pods having three aerosolizers, or more than three aerosolizers, in other embodiments, a pod can have two aerosolizers and provide aerosol mixtures from the substances contained in the two aerosolizers, similar to what is described herein for a three aerosolizer embodiment.

At block 710, the process 700 controls the aerosol produced by each of the three or more aerosolizer's to form an aerosol mixture in an aerosol mixing chamber of the cessation system, the aerosol mixture formed based on the treatment program and based on informant from one or more sensors on the hand-held delivery system. For example, one or more of the sensors illustrated in FIG. 4.

When the delivery system operates to provide a cessation program to a user, a controller circuit executes cessation program instructions which causes signals to be provided to a plurality of aerosolizer drivers. The signals provided to the plurality of aerosolizer drivers can be based on the treatment program instructions, and optionally on information that the controller circuit receives from one or more of the sensors of the delivery system. For example, any one or more of (but not limited to) a flow sensor, an aerosol density sensor, and aerosol temperature sensor, an ambient temperature sensor, ambient pressure sensor, a blood oxygen sensor, and/or a carbon dioxide sensor. The treatment program instructions may include instructions and information that was stored on the delivery system when it was manufactured or configured, and/or instructions and information that were received by the delivery system from a user device 15, a server system, and/or another computer system.

In the embodiments disclosed herein, an aerosolizer system can include one, two, three or more than aerosolizers. In some embodiments, pods having a different number of aerosolizers may be used for different portions of the cessation program, and the (same) delivery device (e.g., delivery device 109) may be configured to work with pods having one, two, three or more aerosolizers.

In the embodiments disclosed herein of a delivery device used with pod having a plurality of aerosolizers, the controller circuit can provide signals to the plurality of aerosolizer drivers 110, based on the treatment program, to cause the plurality of aerosolizers in the pod to produce an aerosol mixture having portions (e.g., percentages) of varying amounts of the substances in the pod. For example, for a pod having three aerosolizers in three substances in the pod (one corresponding to each aerosolizer), the delivery device can provide signals to the three aerosolizer drivers such that a first driver may drive a first aerosolizer to produce 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent (plus or minus 0.5%) of an aerosol mixture (a "resulting" aerosol mixture). The delivery device 109 (e.g., the controller circuit 130) can also provide signals to the three aerosolizer drivers such that a second driver may drive a second aerosolizer to produce 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent (plus or minus 0.5%) of the aerosol mixture. The delivery device 109 can provide signals to the three aerosolizer drivers such that a third driver may drive a third aerosolizer to produce 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent (plus or minus 0.5%) of the aerosol mixture. Similarly, in other embodiments with two aerosolizers or four or more aerosolizers, a delivery device can provide signals to the aerosolizer drivers each aerosolizer correspondingly produces 0-100% of the resulting aerosol mixture.

In addition, the delivery device 109 (e.g., the controller circuit 130) can provide signals to the aerosolizer drivers 110 to produce aerosol from the different substances of different droplet sizes, in accordance with the treatment program. For example, the controller circuit 130 can provide signals to three aerosolizer drivers such that the signals drive three corresponding aerosolizers in a pod to produce aerosol having the same droplet size, or two or more different droplet sizes. In some embodiments, the aerosol droplet diameters will be less than 1 μm, or equal to 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, or 20 μm, plus or minus 0.5 μm.

Figure 7C:
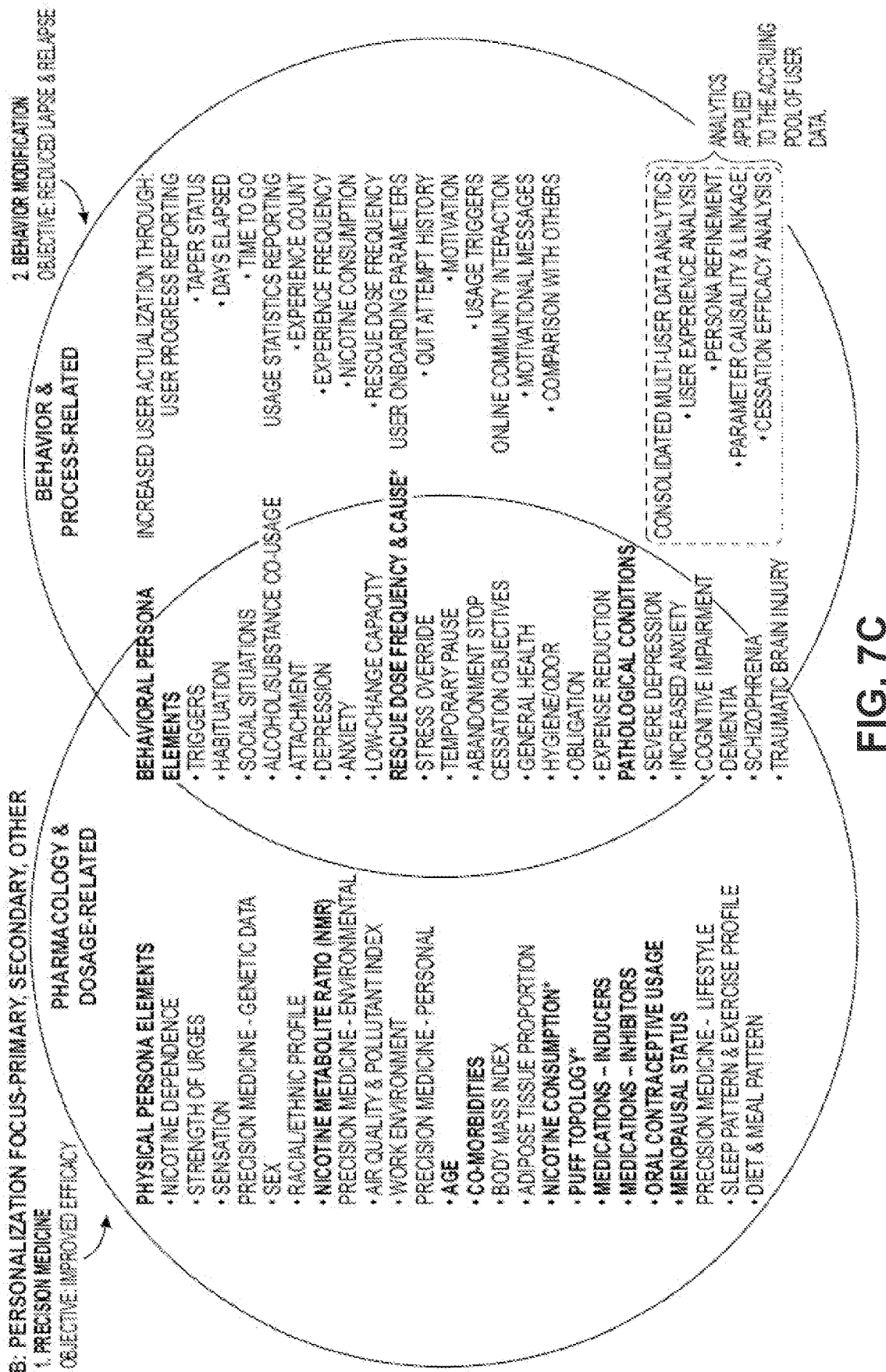
FIG. 7C is a diagram illustrating an example of primary, secondary, and other focused personalization domains utilized by the smoking cessation system.
Figure 7D:
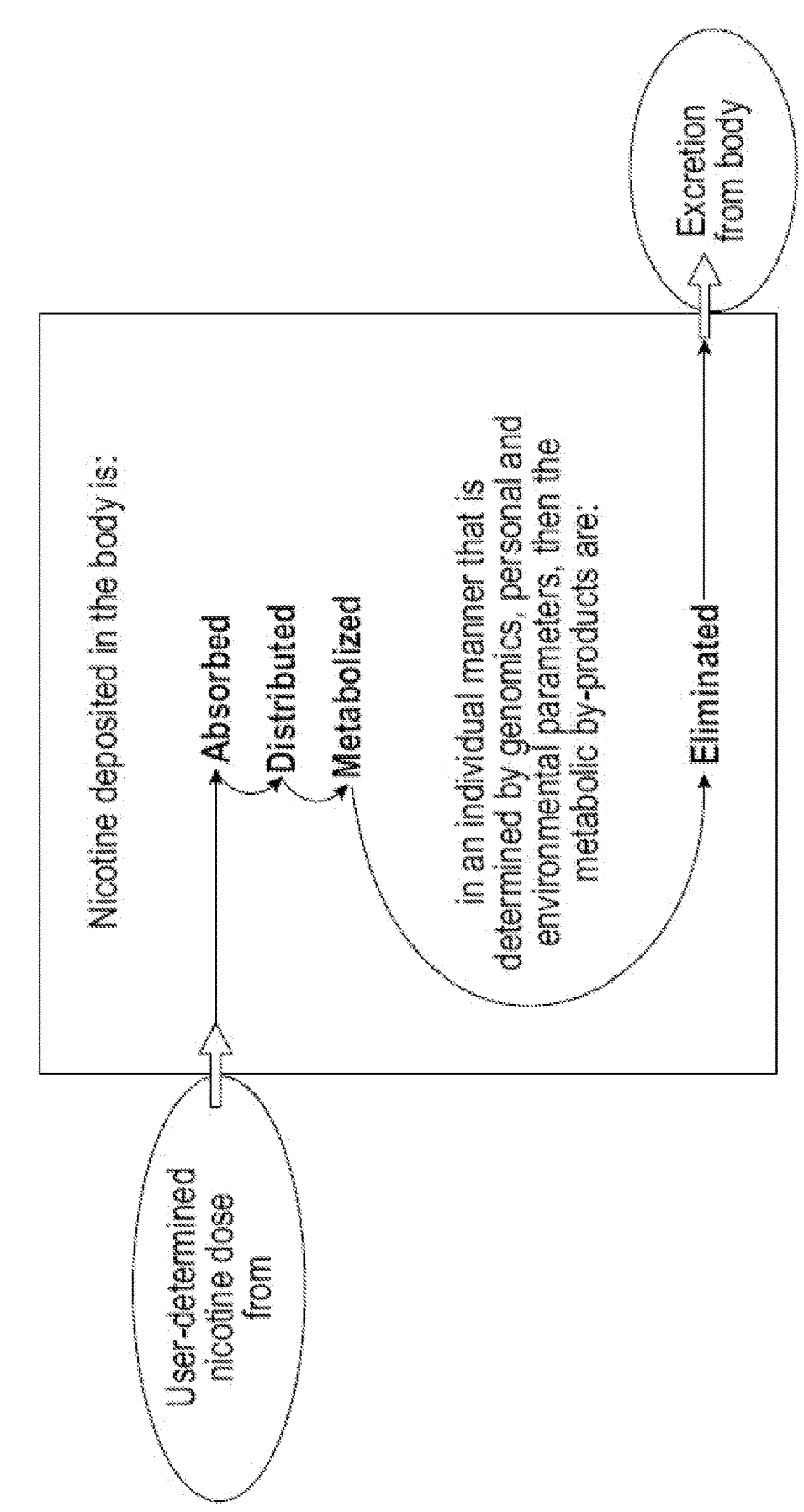
FIG. 7D is a diagram illustrating an example of how nicotine is deposited within the body, according to one embodiment.
Figure 7F:
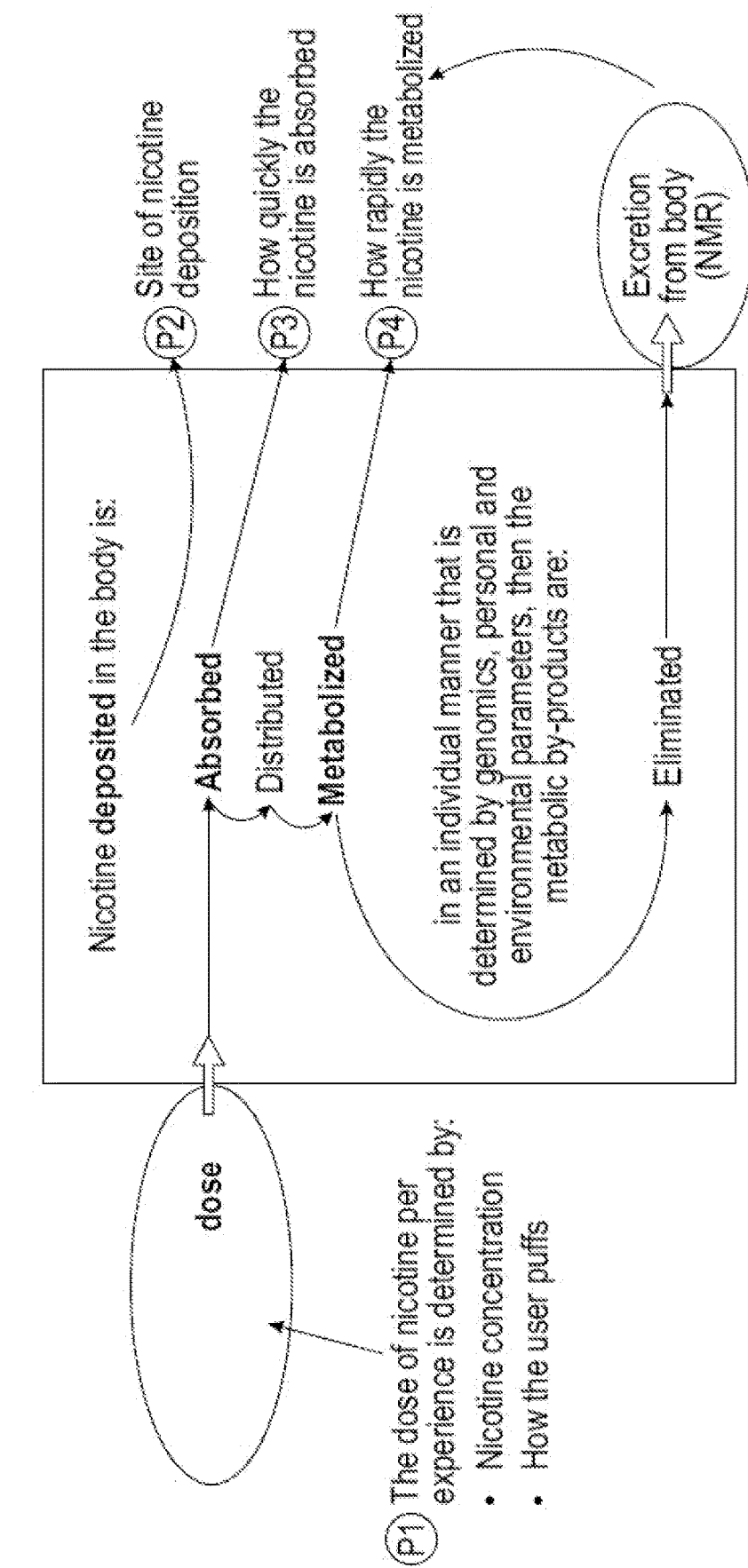
FIG. 7F is a diagram illustrating an example of four key personalization parameters and their effect on nicotine deposited in the body.
Figure 7G:
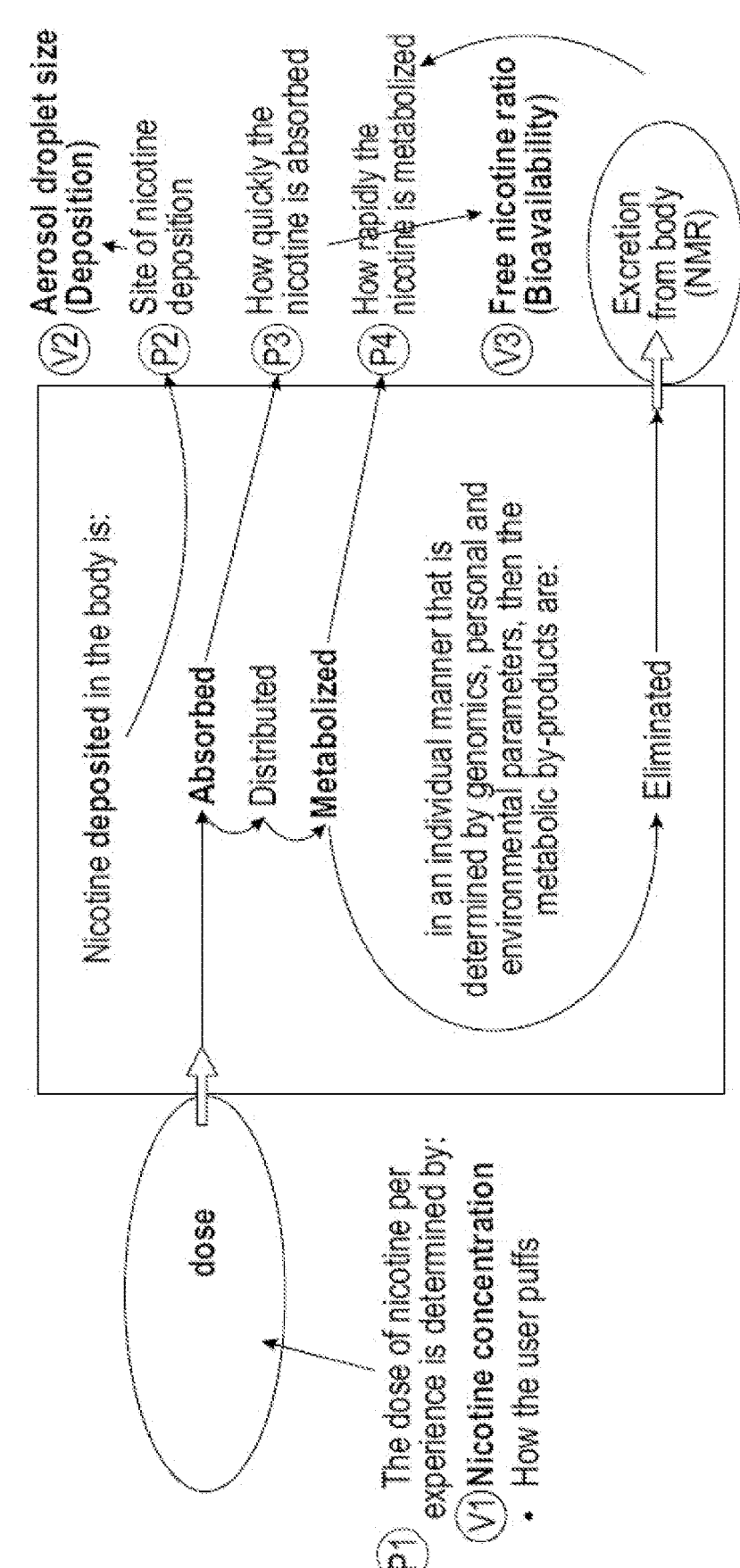
FIG. 7G is a diagram illustrating an example of how the four key personalization parameters determine three critical variables.
Figure 7H:
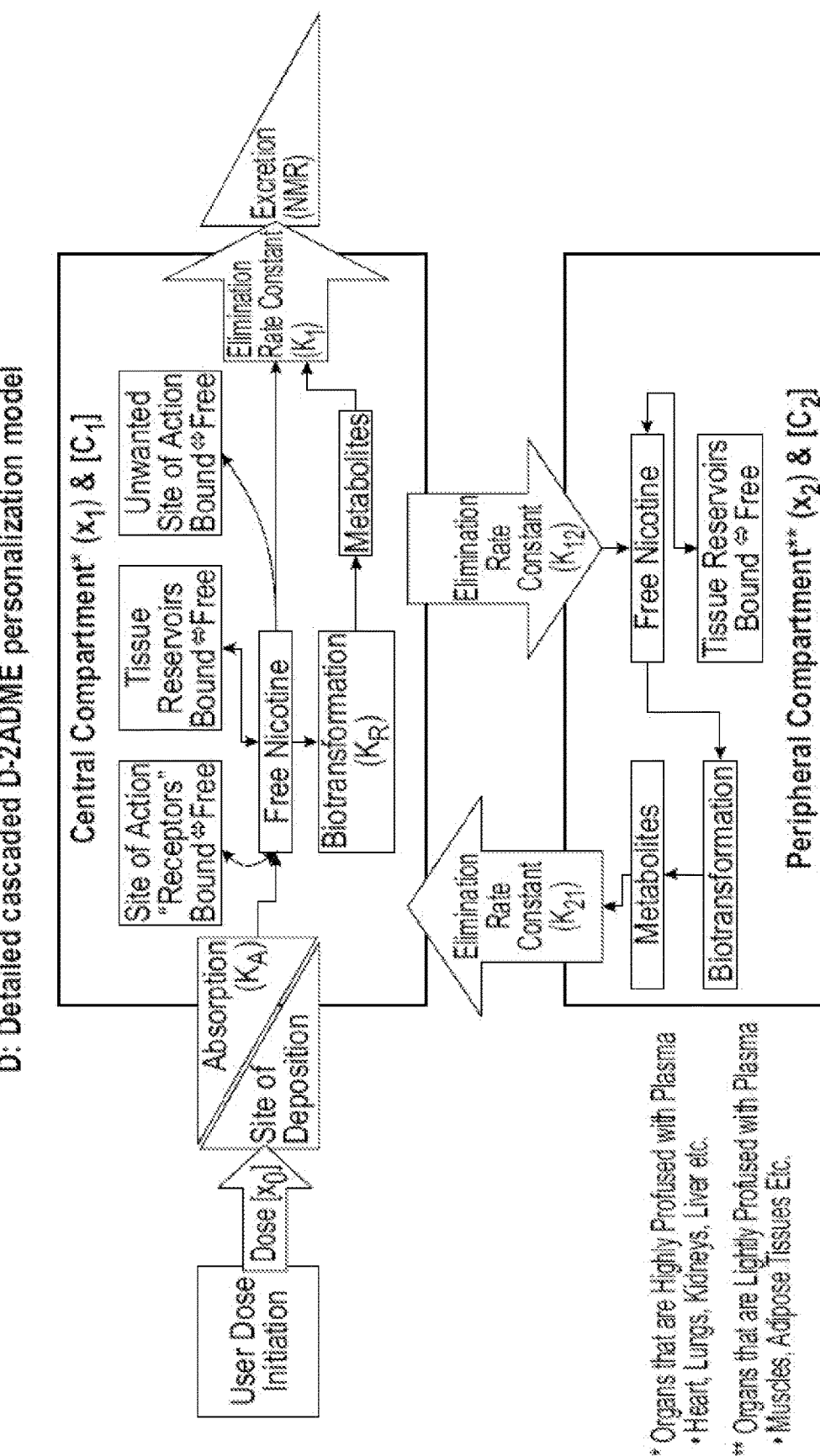
FIG. 7H is a diagram illustrating the cascaded D-2ADME personalization model.
Figure 7I:
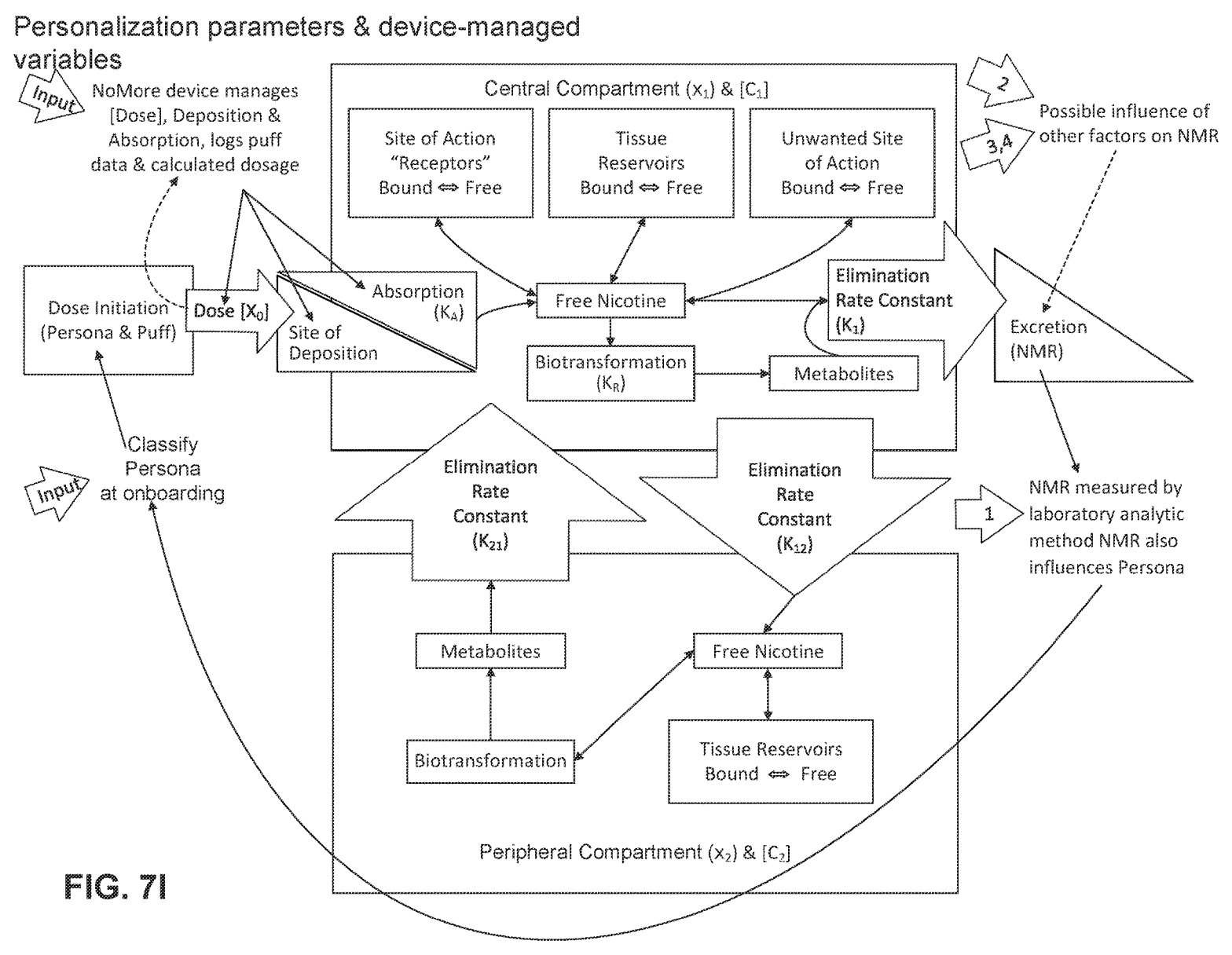
Figure 7K:
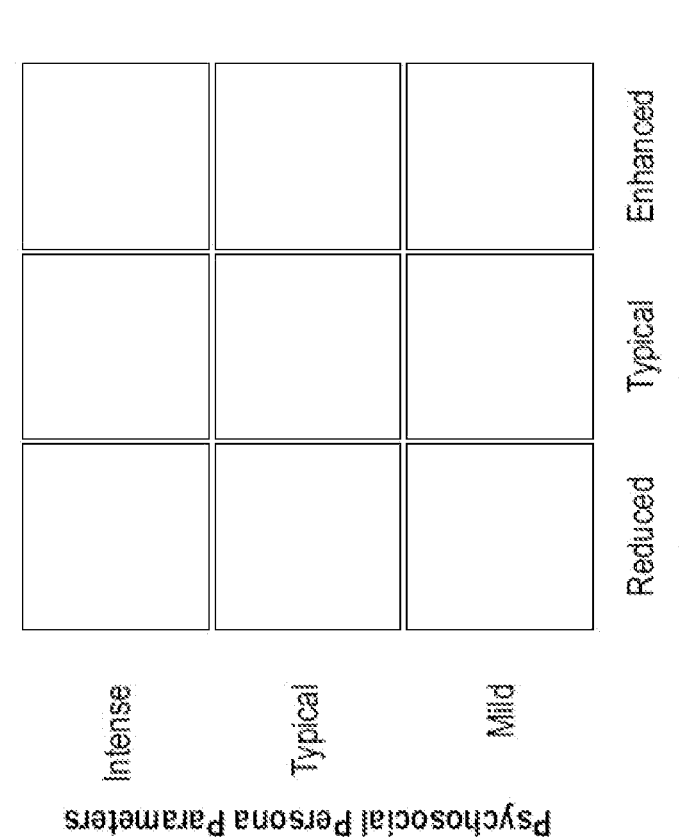
FIG. 7K is a diagram illustrating how personalization parameters and clustered persona characteristics are used to map cessation liquid parameters.
Figure 7M:
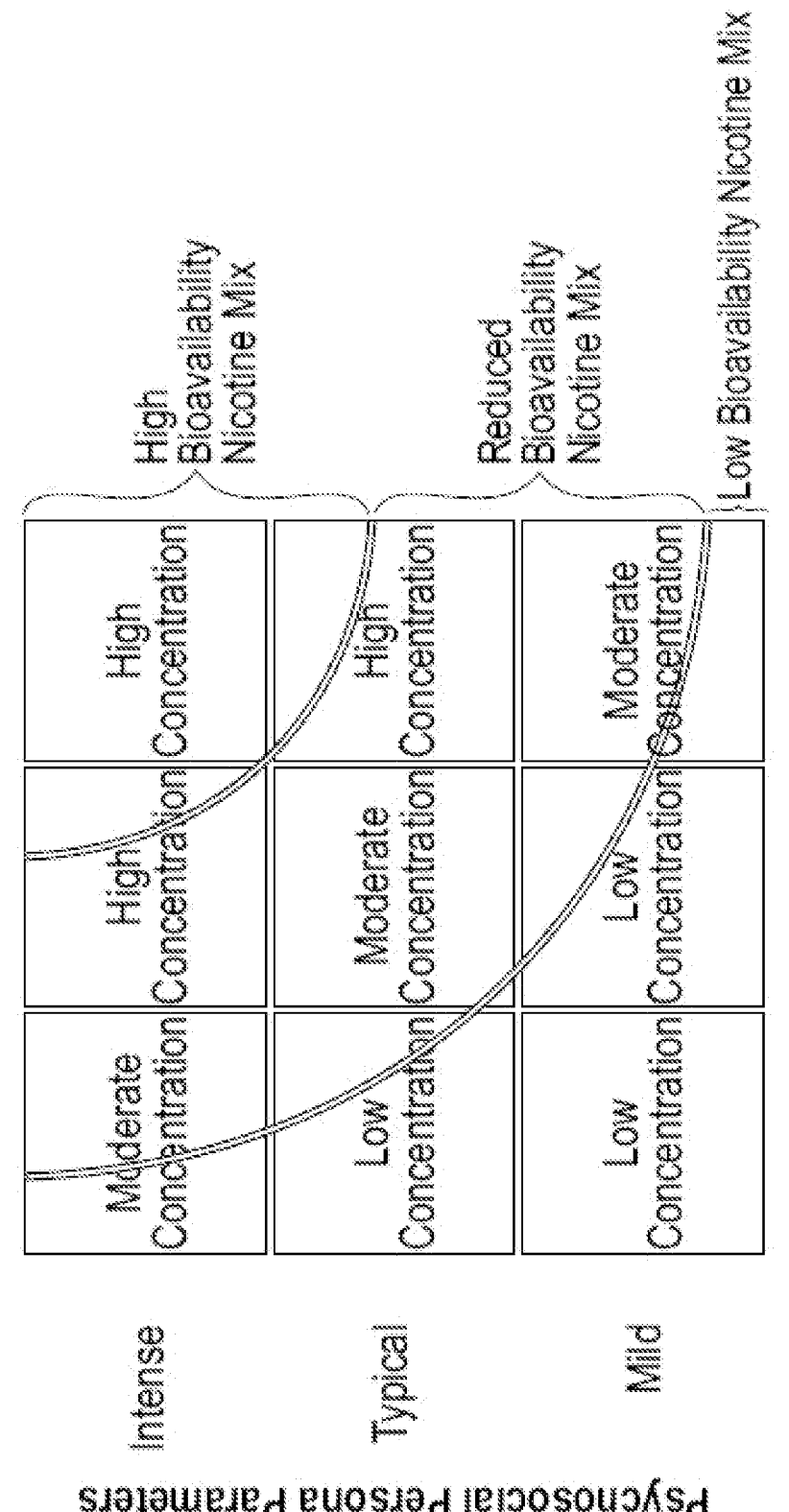
FIG. 7M is a diagram illustrating bioavailability mapped to persona and metabolism rate.
Figure 7N:
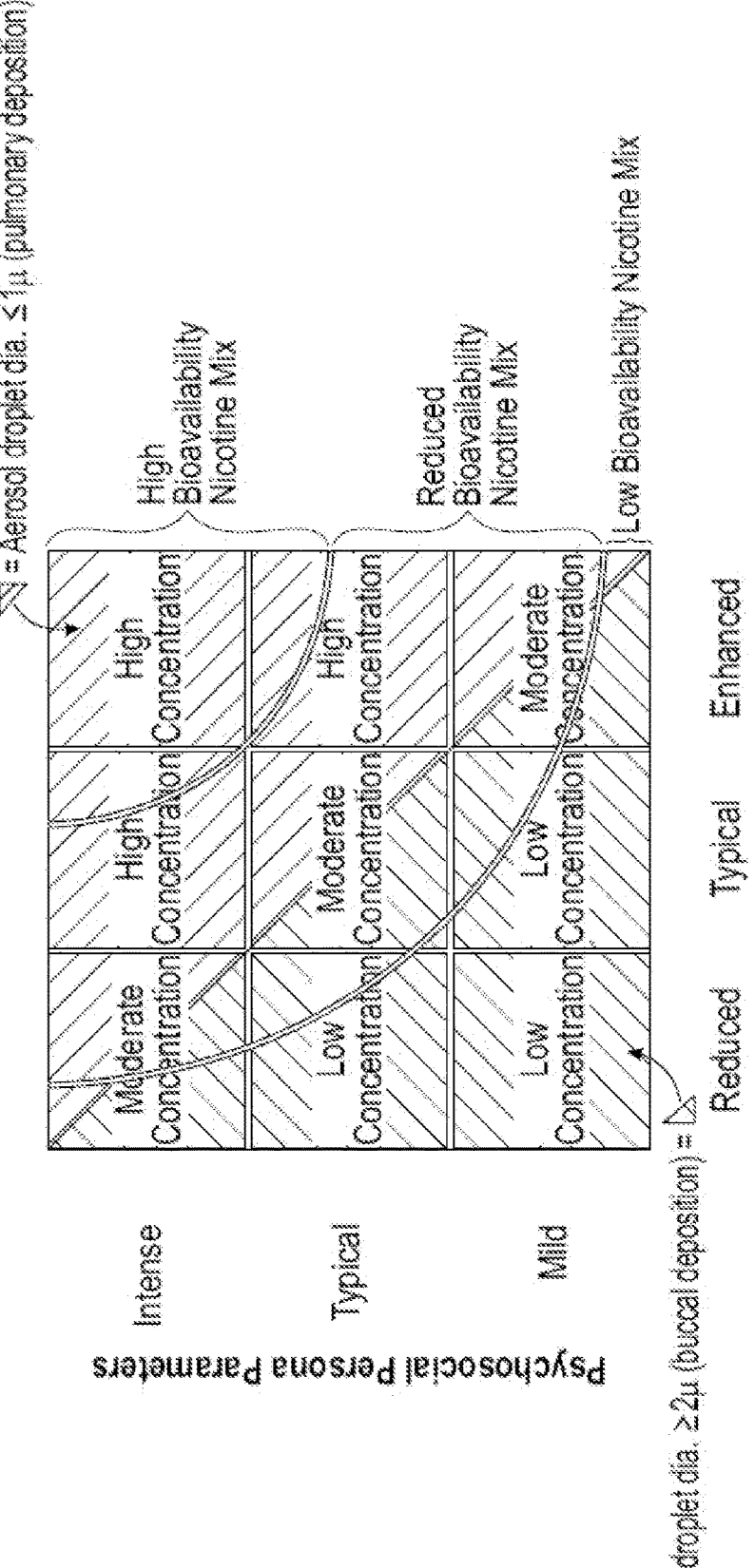
FIG. 7N is a diagram illustrating aerosol droplet size mapped to persona profile and metabolism rate.
Figure 7Q:
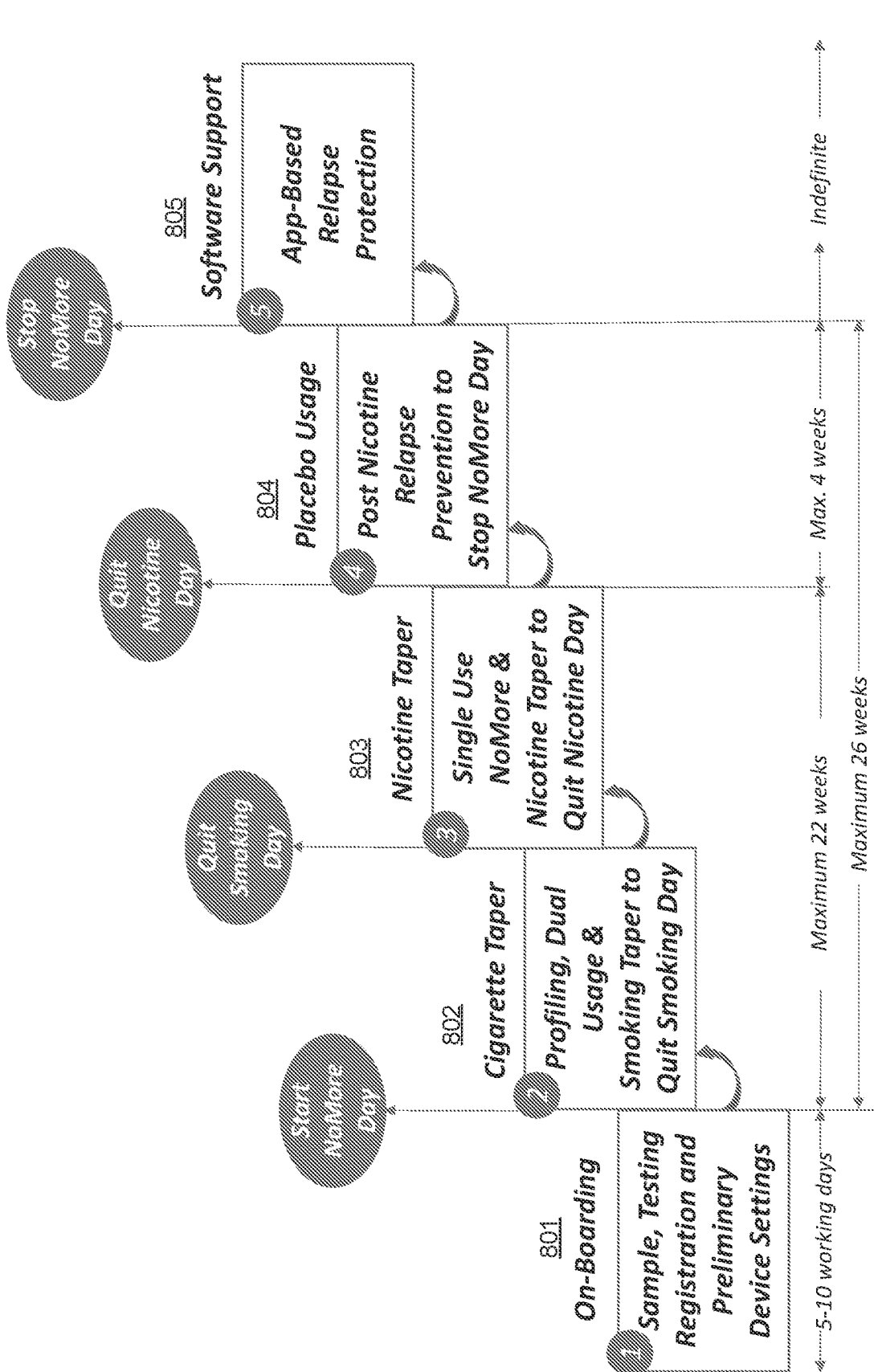
FIG. 7Q is a diagram illustrating a five step process that can be implemented for a cessation program.

In reference to the illustrative example of a smoking cessation treatment program developed to wean an individual from smoking or vaping, certain co-factors can be evaluated to create a cessation program or treatment plan for a particular user, for example similar to the program illustrated FIG. 7Q. FIGS. 7A, 7B-1, 7B-2, and 7C illustrate how behavior modification and precision medicine can affect personalization domains that influence how a body processes nicotine. FIGS. 7D, 7E, 7F, 7G, 7H, and 7I illustrate the D-ADME[2] model that can determine how biological effects are elements of a smoking persona. FIG. 7J illustrates how psychosocial co-factors may result in a user being compelled to initiate a smoking experience. Finally, FIGS. 7K, 7L, 7M, 7N, 7O, and 7P demonstrate how persona and personalization parameters can be used to map cessation liquid variables.

A treatment program or smoking cessation can be created by a combination of biological, psychosocial, and clinical co-factors, which can be referred to as a smoking persona. This information may be input as parameters that are used to control the delivery device to vary concentrations of the substances contained in the aerosolizer system at different points in a period of time during a program schedule for a certain person. Biological co-factors can be an individual's unique adaptation to nicotine related to their individual neurobiological phenotype. Psychosocial co-factors can be an individual's unique conditioned triggers to smoke with respect to personal and environmental conditions. Clinical co-factors can be severe psychological or cognitive challenges.

Additional parameter considerations may include smoking drivers and quit inhibitors. Managing smoking drivers and quit inhibitors to wean an individual off smoking or vaping can be a combination of a delivery/device system use, behavioral software use, and medical consultation. The following table indicates possible smoking drivers or quit inhibitors, a description of each, and how the cessation system, software, or advisor/medical consultation may help. In this example, and generally herein, a smoking cessation delivery device and smoking cessation treatment program may be referred to a "NoMore" device/program.

| | Smoking Driver, Quit Inhibitor & Related Persona Element | Description/Example | Assessment | Delivery Device ("NoMore") | Behavioral Software | Medical Consultation |
|---|---|---|---|---|---|---|
| Biological | Nicotine Dependence (Manage with Device) | Nicotine dependence varies across smokers. Some people have severe withdrawal, others have almost no withdrawal. Nicotine half-life is 2 hours so withdrawal may start 1 hour after smoking | Nicotine Metabolite Ratio (NMR) Fagerström FTND Question 1. Wisconsin Smoking Withdrawal Scale | Dependence level sets the Initial Nicotine Concentration Sets the Nicotine Taper Rate | | |
| | Sensory Experience (Manage with Device) | Some people enjoy the sensations of smoking while others do not. People like different amounts of "throat hit" People like different flavors | 1. How much do you enjoy smoking? 2. How much to like the feeling of inhaling cigarette smoke? 3. How much do you like the feeling of "nicotine burn"? 4. What flavor do you like? | Use desired throat hit to set αfb to an initial setting. Then reset αfb during nicotine taper when nicotine concentration is low. | | |
| Psychosocial | Triggers (Manage with Behavioral Tech) | i. External stimuli (the smell of smoke, movie) ii. Daily routine (e.g., after each meal, driving, phone) iii. Places (their chair, outside) iv. Emotions (celebration, anger, loneliness, boredom) v. Social situations vi | Ask about each category of trigger + give example. Ask how much does this trigger drive your smoking. | | Before the quit smoking day, develop a strategy for managing each category of trigger. This will include the use of NoMore, and will include other | |

-continued

| Smoking Driver, Quit Inhibitor & Related Persona Element | Description/Example | Assessment | Delivery Device ("NoMore") | Behavioral Software | Medical Consultation |
| --- | --- | --- | --- | --- | --- |
| | Stressful events vii. Alcohol/other substances | | | strategies as well. | |
| Social Smoking (Manage with Behavioral Tech) | Social smoking can be difficult to overcome because it involves group identification, social acceptance. This is a bigger problem for younger people. | Do you sometimes smoke with others? If yes, Who do you smoke with? | | Add "Social Module" to plan - 1. Tell friend you will use NoMore. 2. Ask friend not to smoke. 3. Stop seeing friend. | |
| Ritual Smoking (Manage with Device and Behavioral Technology) | Older smokers in particular, tend to show increased ritual smoking - smoke the same number of cigs each day with their daily routine | Ask about daily routine (Part of triggers survey) | Extend taper to 12 weeks, will likely need a long period after taper also. | Introduce plan to replace routine cigarettes with NoMore (e.g., use NoMore after each meal) | |
| Stressful Event (Manage with Device and Behavioral Technology) | Stressful event may be very small to very large. A stressful event is the number 1 reason for relapse back to smoking. Relapse occurs because of high stress in combination with poor coping skills. | 1. Did you ever quit smoking before? 2. If yes, what led to relapse? 3. What portion of your cigarettes do you smoke due to stress? 4. How much has stress kept you from quitting? | Use of Rescue Dose The dosing will be set up | Mindful use of NoMore, Mindfulness of emotions. Pause, recognize the stressful situation, recognize your response to the situation. Decide what to do. | |
| Attachment (Manage with Behavioral Tech) | Some feel cigarettes are their "best friend." They can cut down to 1 cig/day, but cannot stop. Grieving occurs after stopping | "Have you ever thought of smoking as a close friend?" Also -Device check: if they are unable to quit smoking after tapering down cigs or unable to stop product after tapering down | | Training in letting go, grief counseling | Inability to quit may require medical consult if person is stuck. |
| Clinical Alcohol/Substances (Manage with Behavioral Tech and possibly with Medical Consult) | Alcohol/substance use is common in smokers and highly associated with relapse. 1. Alcohol and smoking can be associated as a routine, 2. Increases smoking urges. 3. Alcohol decreases ability to exert will power and increases automatic smoking. | 1. On average, how many days per week do you drink? 2. What is the most number of drinks you will have in a day? | | 1. While drinking, can a person use NoMore instead of smoking? If yes, continue drinking as before 2. If no, then reduce drinking to 1 drink per day. | 3. If they continue to smoke while drinking, and are unable to cut down, this requires a Medical Consult |
| Depression (Manage with Behavioral Tech and possibly with Medical Consult) | Severe depression is highly associated with inability to quit and relapse | PHQ-2 > 3 do PHQ-9 PHQ-9 > 4 - see B Technology PHQ-9 > 9 Get consult | | PHQ > 4 add depression component to behavioral approach | PHQ > 9 requires medical consult |
| Anxiety (Manage with Behavioral Tech and possibly with Medical Consult) | Severe anxiety is highly associated with inability to quit and relapse | GAD-2 > 3 do GAD-7 GAD > 4 - see Beh. Technology GAD-9 > 9 Get consult | | GAD > 4 - add anxiety module to behavioral approach. | GAD-9 > 9 requires medical consult |
| Low Change Capacity (Manage with Medical Consult) | People with traumatic brain injury, cognitive impairment, dementia, late stage | Ask - do you have a history of traumatic brain injury, cognitive impairment, dementia, late stage | | | Requires a medical consult |

| Smoking Driver, Quit Inhibitor & Related Persona Element | Description/Example | Assessment | Delivery Device ("NoMore") | Behavioral Software | Medical Consultation |
|---|---|---|---|---|---|
| | schizophrenia may smoke as a ritualized behavior, may smoke more e.g., 3-4 packs per day. | schizophrenia, or similar? | | | |

In the table above, "PHQ" refers to the commonly known Patient Health Questionnaire self-administered version of the PRIM-MD diagnostic instrument for common mental disorders. PHQ-9 is the depression module. PHQ-2 inquires about the frequency of depressed mood and anhedonia over a time period (e.g., 2 weeks), and includes the first two items of the PHQ-9. "GAD" refers to the commonly known a generalized anxiety disorder score.

FIG. 7A is a diagram illustrating pharmacological dosage related personalization data and behavior modification as two intersecting domains of cessation program personalization.

FIGS. 7B-1 and 7B-2 are a two-part table illustrating personalization parameters that influence how the body processes nicotine and how each may be quantified. The personalization parameters can be divided into primary, secondary, and tertiary/quaternary parameters based on prioritization.

FIG. 7C is a diagram illustrating an example of primary, secondary, and other focused personalization domains utilized by the smoking cessation system which were previously illustrated in FIG. 7A and FIGS. 7B-1 and 7B-2.

FIG. 7D is a diagram illustrating the basic model components of D-ADME$^2$ and how nicotine may be deposited within the body. As the figure indicates, nicotine can be absorbed, distributed, and metabolized based on an individual's genomics and personal and environmental factors. The byproducts from this process can be eliminated and excreted from the body. FIG. 7D demonstrates how biological co-factors can help define a smoking persona.

FIG. 7E is an example of how calculating nicotine input and measuring nicotine output can determine how an individual metabolizes it, often called the Nicotine Metabolite Ratio (NMR). In some embodiments, NMR may be calculated for an individual to reveal how rapidly an individual biochemically processes nicotine. This information can be applied to form an individual's persona and be input parameters for a cessation program.

FIG. 7F illustrates the same diagram as FIG. 7D and how nicotine is deposited in the body. Additionally, the diagram identifies four key personalization parameters that can be configured for use in a cessation program. In some embodiments, four parameters include the dose of nicotine received by the user when using a cessation device, the site of the nicotine deposition, how quickly the nicotine is absorbed, and how rapidly the nicotine is metabolized.

FIG. 7G contains the four key personalization parameters as illustrated in FIG. 7F, but in this embodiment, shows three critical variables of the cessation liquid and aerosol that can affect the personalization parameters. In some embodiments, three critical variables include nicotine concentration, aerosol droplet size, and free nicotine ratio.

FIG. 7H is an example embodiment of the detailed cascaded D-2ADME personalization model illustrating the central compartment and the peripheral compartment.

FIG. 7I takes the same cascaded personalization model of FIG. 7H and illustrates how adding personalized user persona information and configuration of the cessation device can affect NMR.

FIG. 7J is a diagram illustrating how psychosocial co-factors can affect how nicotine is deposited in the body when a user is compelled to smoke. Psychosocial co-factors, as discussed previously, can include triggers, attachment, substances, and pathologies.

FIG. 7K is a diagram illustrating how personalization parameters and clustered persona characteristics can be used to map the magnitude and range of associated cessation liquid parameters. The intersection of biological persona parameters and psychosocial persona parameters can create varying levels of cessation liquid necessary for a cessation program.

FIG. 7L illustrates the diagram of FIG. 7K with low, moderate, or high nicotine levels according to persona level. In one embodiment, reduced biological persona parameters with mild psychosocial persona parameters would result in a low concentration of concentrated nicotine for a cessation program. In an alternate embodiment, enhanced biological persona parameters paired with intense psychosocial persona parameters may result in a recommended high concentration of nicotine.

FIG. 7M adds to the FIG. 7L to illustrate bioavailability of nicotine across personas.

FIG. 7N adds to FIG. 7M to illustrate how aerosol droplet size is mapped to persona profile and metabolism rate. In one embodiment, a larger aerosol droplet may result in a higher concentration at a pulmonary deposition. In another embodiment, a smaller aerosol droplet may result in a lower concentration at a buccal deposition.

FIG. 7O adds to FIG. 7N illustrating how frequency of smoking and puff topology can add to the uniqueness of the cessation liquid variables for a user. In one embodiment, a middle-aged, heavy smoker, typical metabolizer, severe withdrawal symptoms, elevated smoking urges, enhanced sensory enjoyment, intense alcohol use, and elevated smoking attachment may result in a higher concentration of nicotine for the user.

FIG. 7P illustrates how the users from FIG. 7O can benefit from a unique cessation program based on cessation start point, age, behavioral information related to triggers, stresses, anxiety, depression, alcohol consumption, and social cue responses. In one embodiment, the cessation program may create unique taper paths, taper rates, and program durations for different users.

FIG. 7Q is a diagram illustrating an example of a five-step process can be implemented for a treatment program designed for quitting smoking. In this example, the program includes on-boarding 801, cigarette taper 802, nicotine taper 803, placebo usage 804, and software support 805 phases.

The objectives of the on-boarding phase 801 is to register and enroll a user and to do preliminary device configuration. This on-boarding phase 801 may begin with an appointment with a prescribing physician and end with NMR analytical results. Some steps for dosage calculation may include obtaining a saliva sample for analytical NMR determination, identifying a likely consumable category based on persona, creating a preliminary definition of cessation liquid initial values based on persona, confirmation of age, a physician interview to assess menopausal status, co-morbidities, medications, lifestyle factors, creating a preliminary definition of taper path and taper rate based on age and persona, and configuring NMR input upon receipt of laboratory results.

Some psychosocial and clinical actions included in the on-boarding phase 801 may include defining an aspirational definition of cessation process duration, qualitative determination of persona elements (e.g., name, gender, age, occupation, location, etc.), an overview of the behavioral program in subsequent steps (education, identification of triggers, managing urges, managing stress, the smoking taper, the quit process), overview of social support, overview of professional support, physician interview to identify presence of/susceptibility to additional behavioral components (uncontrolled severe stress, generalized anxiety disorder, depression, bipolar disorder, post traumatic stress disorder, pre-existing traumatic brain injury, schizophrenia), and to set a date for profiling.

Other actions of an on-boarding phase 801 can include various registration activities, subscription to consumables delivery service, user specification of flavor system (tobacco, menthol none), or enlist willing onboarded cessation system users under the auspices of a "pay it forward" strategy to help two other people quit once they have successfully quit. Although the length of time for on-boarding can vary based on a number of factors, it typically may be about 5-10 working days.

In this example, the second phase of the treatment program is a cigarette taper phase 802 which may include profiling and product familiarization. Objectives of this cigarette taper phase 802 may be to finalize personalization, define start delivery parameters, and/or set a quit smoking day. This phase may start immediately after NMR results are configured and end with a successful quit smoking day.

Some steps for dosage calculation may include setting initial delivery parameters to match cigarette experience based on persona data. In one example, set initial nicotine concentration r=3% w/w, initial free fraction αfb=0.03, for light smoker <1 pack/day with low NMR. In another example, set initial nicotine concentration r=5% w/w, initial free fraction αfb=0.07, for heavy smoker >1 pack/day with elevated NMR. In yet another example, set initial aerosol droplet size δ≤1.0 μm.

Another dosage calculation action may be setting initial PRN/rescue concentration higher than standard but with same αfb and δ according to persona. For example, a light smoker nicotine concentration r=5% w/w and a heavy smoker nicotine concentration r=7% w/w.

Other dosage calculation actions may include 5 day and 10 day parameter ranging evaluation (including systemic increasing and decreasing around initial settings and PRN dose settings for nicotine concentration r and initial free fraction afb with 6 constant to establish final parameter values for the objective of a satisfying and pleasant routine dose or maximally satisfying and tolerable PRN dose), recording of user puff topology to enable dose calculation, finalize delivery parameters and update program configuration, or confirmation or adjustment of cessation taper duration for subsequent step.

Psychosocial and clinical actions in the cigarette taper phase 802 can include to define a Quit Smoking Date (QSD) (estimate 2-4 weeks from beginning of Dual Usage phase) comprising: cessation program learning/adaptation period (5-10 days) using initial delivery parameter values from the on-boarding phase 801, or dual usage (14-21 days) with cigarette taper (steps below).

The cigarette taper:
Techniques for smoking tapering: 1) ad-lib; 2) frequency reduction (only every hr ~16/day, then only every 2 hrs~8/day); 3) scheduled smoking (on waking, after eating, and one in the evening ~5/day).
Using selected technique to cut cigarette smoking in half to 10/day in the first 50% of time to QSD; then again in half to 5/day at 75% to QSD; then zero when QSD has been reached.
Replace cigarette reduction with NoMore usage.

Another psychosocial action may be progressive behavioral training (education concerning health risks like lung cancer, chronic obstructive pulmonary disease (COPD), and heart disease, identification and recording of triggers like temporal, association, emotional, location, and alcohol, or mindfulness training for stress management), a call with a professional counsellor 2-3 days before Quit Smoking Day to enhance chance of behavior change, or calls with former cessation program users as quit advisors.

Other actions in the cigarette taper phase 802 may include a cessation program training video to cover inhalation changes with respect to reduced rate & increased depth, how the cessation program is different from smoking, function of lights and buttons, battery recharging, replacing consumables, or general usage recommendations for learning period. Other actions may also be configuration of consumable replenishment schedule. One action may cover steps to take if Quit Attempt is unsuccessful: do not progress to the nicotine taper phase 803, re-evaluate and assess what went wrong, create a new strategy based on what went wrong (if stress, then stress management behavioral therapy, if motivation/social, then enhance social support elements, or if technical, then review product information/video), engage medical support if simply not engaged, set new Quit Day in 2-4 weeks & make plan to prepare for it, or reset taper and start cigarette taper phase 802 again. Although the length of time for the cigarette taper phase 802 can vary based on a number of factors, it typically may be in the range of about 7 to 15 weeks long.

In this example, a third phase of the treatment program for quitting smoking may be a nicotine taper phase 803. This phase may include the objective to end the use of nicotine. This phase may start after a successful quit smoking day and end when cessation taper reaches final dose of nicotine level.

In some embodiments, the steps for dosage calculation may include not changing the previously established PRN/rescue settings, beginning cessation taper from previously defined start conditions for nicotine concentration, free fraction, and aerosol droplet size, starting taper two weeks after beginning the nicotine taper phase 803, applying taper variables and rate according to the previously defined taper parameters, monitoring PRN/rescue usage and adjusting taper variables if it is determined that the taper is too fast, or not long enough in duration.

Regular high PRN use >10x on consecutive days (3-4):
Indicates standard dose insufficient. Re-evaluate taper and consider adjustment.

Consult with user concerning dosage increase.

Re-test to determine threshold for routine dose; reset taper to this new dosage; reduce taper rate.

At final dose likely nicotine concentration ρ<1% w/w:

Increase aerosol δ≥2.0 μm to reduce absorption rate & peak

Increase free ratio $0.01 \leq \alpha_{fb} \leq 0.03$ to give throat hit.

In some embodiments, the psychosocial actions may include defining a date for taper to reach final dose nicotine and the end of the nicotine taper phase 803 (clearly defined date with total use of cessation program not to exceed 26 weeks). Other psychosocial actions may include recording clearly defined date and time, or monitoring PRN/rescue dose usage, assisting with recognition of stressful events & management without smoking.

If Lapse occurs (use of 1-2 cigs/day plus cessation program):

Counselling, evaluation, encouragement to restart.

Consider taper adjustments.

If Relapse occurs (return to full smoking at level present starting the cigarette taper phase 802):

Restart at beginning of the cigarette taper phase 802.

Consider taper adjustments.

If repeated taper reset, relapsing and failure in the nicotine taper phase 803:

Ensure cessation program is not regarded as a recreational product that can be used forever.

Allow for 2-3 potential taper resets in high-dependence users.

Allow for possible extension of total Quit Process time on condition of medical consult.

In taper "tail" phase with final dose extremely low, expect phase to last 2-6 weeks:

NoMore as crutch in this phase.

PRN/rescue doses still available.

At final dose, assess user and consider prolonged usage as long as total usage does not exceed 26 weeks.

Other actions in the nicotine taper phase may include preparing for transition out of cessation program use or preparing for provision of potential support for others in the online community.

In this example, the fourth phase of the treatment program may be a placebo usage phase 804 which may include the objectives of no nicotine consumption and no user relapse. This phase may start after successful Quit Day or 26 weeks, whichever first. The phase may end with no grieving or withdrawal symptoms. The psychosocial & clinical actions may include defining post-quit duration, monitoring to ensure no physical withdrawal symptoms, support for potential grief management, ongoing behavioral modification support (proactive recognition of stressful events or stress management without resorting to smoking), or recording of triggers and cues (uploading for monitoring and behavioral support).

Other actions in the placebo usage phase 804 may include video training for potential role as coach and support resource in online cessation program community.

In this example, the fifth phase of the cessation program is a support phase 805 which may include the objective of stopping the use of the cessation program. The phase may end when the user decides. Dosage actions in this phase may include cessation system device usage disabled unless intended use is transitioned from Cessation to Reduced Exposure & Reduced Risk. One psychosocial action may include community reinforcement support. Other actions may include active participation in Online Support "pay it forward" community or potential intended use transition to Reduced Exposure & Reduced Risk in certain extreme cases.

Figure 8A:
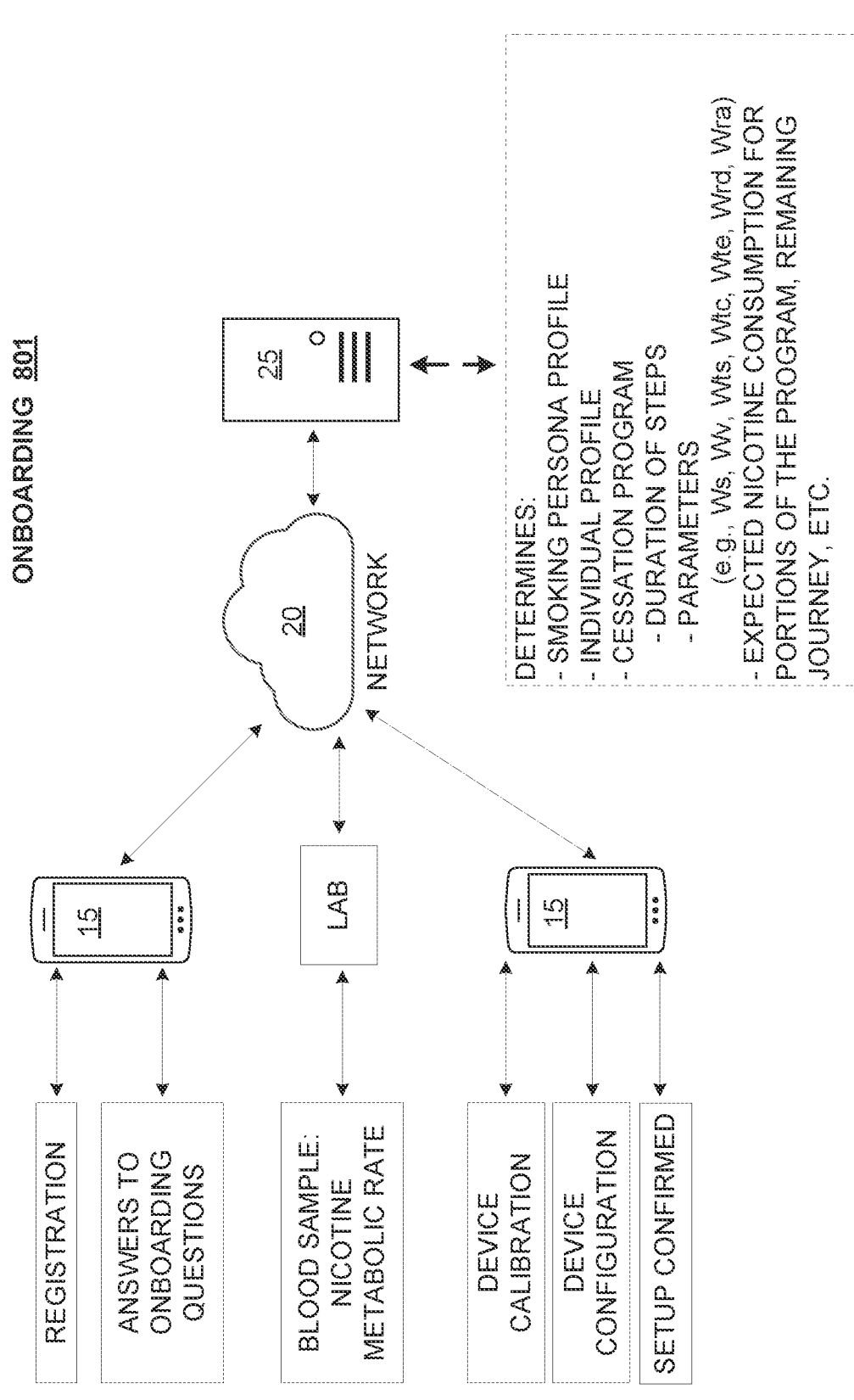
FIG. 8A is a block diagram illustrating aspects of an onboarding process for a smoking cessation system, which can be the first portion of a process for helping a user quit smoking, an example of other subsequent portions of such a process are illustrated in FIGS. 10A-10L.

FIG. 8A is a block diagram further illustrating certain aspects of the onboarding process for a treatment program for quitting smoking. An onboarding process of the treatment program can be run by the user device 15 and the server system 25 to register a user, including providing questions to the user and receiving information specific to the user/answers to the questions. One or more test may be performed on the user and information from a lab conducting the tests (e.g., determination of NMR) can be received by the treatment program, e.g., on the server system 25. Based on user provided information and any test information, the treatment program can determine for the user a smoking persona profile, an individual profile, a smoking cessation treatment program. The treatment program can include various aspects including one or more of a determination of a number of steps, a planned duration of each of the steps, initial parameters that will be needed to control the delivery device, an expected nicotine consumption of the program and portions of the program.

Figure 8B:
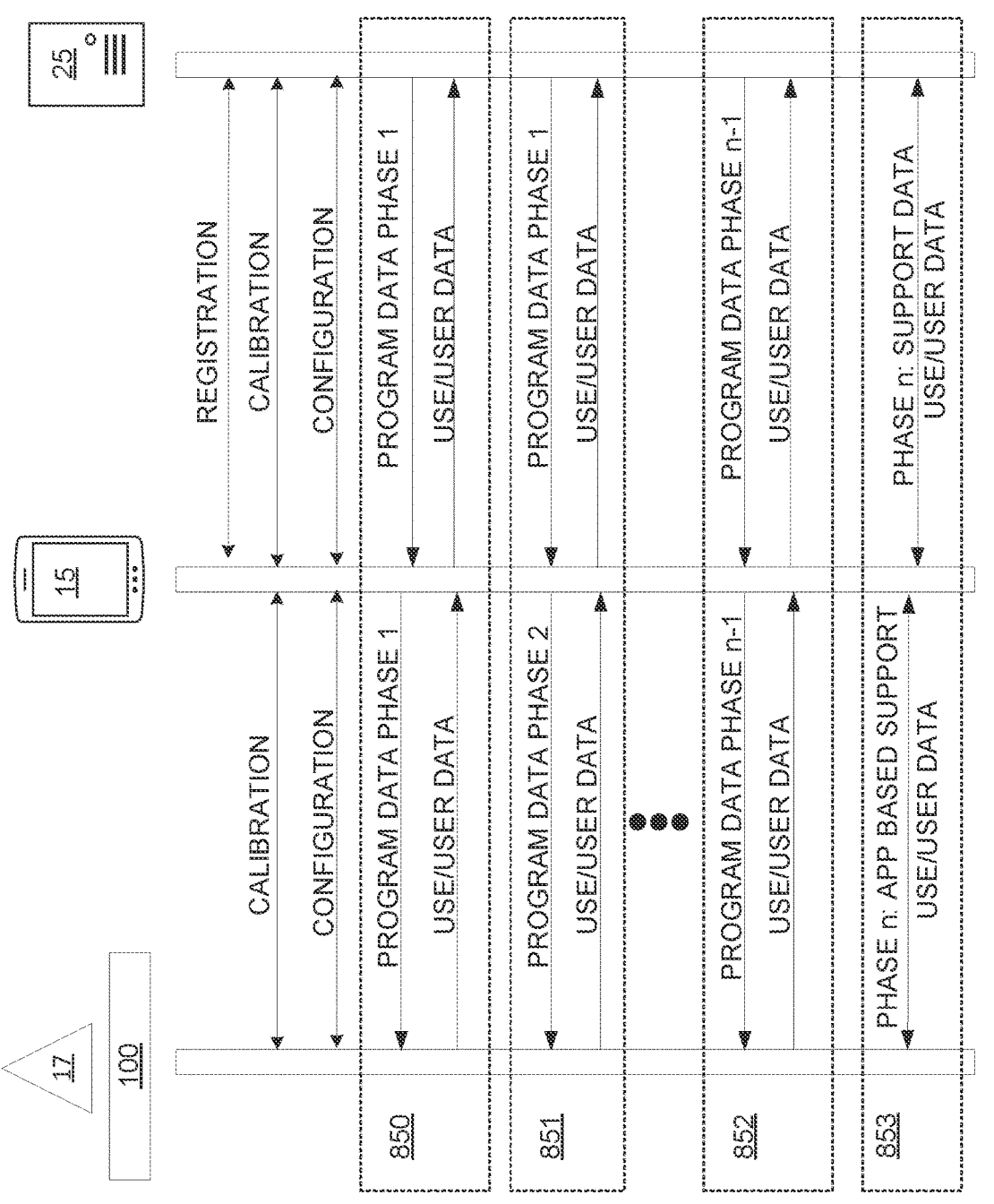
FIG. 8B is a diagram illustrating aspects of data communications between the server system, the user device (mobile platform), and the delivery system, for example, the server system, user device, and the delivery system illustrated in FIG. 1.

FIG. 8B is a diagram illustrating aspects of data communications between a server system, a user device (mobile platform), and a delivery system performing a process for a medical treatment. For example, the server system 25, user device 15, and the delivery system 100 illustrated in FIG. 1 performing processes for a smoking cessation program. All of the server system 25, user device 15, the delivery system 100, and sensor(s) 17 can include hardware processors and non-transitory computer readable medium and that include instructions that when executed, configure the respective hardware processors to perform processes for a health treatment program. These processes include hardware components (e.g., a transceiver, antenna, etc.) for one or two-way communications between the sensor(s) 17, delivery system 100, user device 15, and server system 25 to control providing substances to a user by the delivery system 100 according to a treatment program being run on the server system 25 and the user device 15.

Figure 8C:
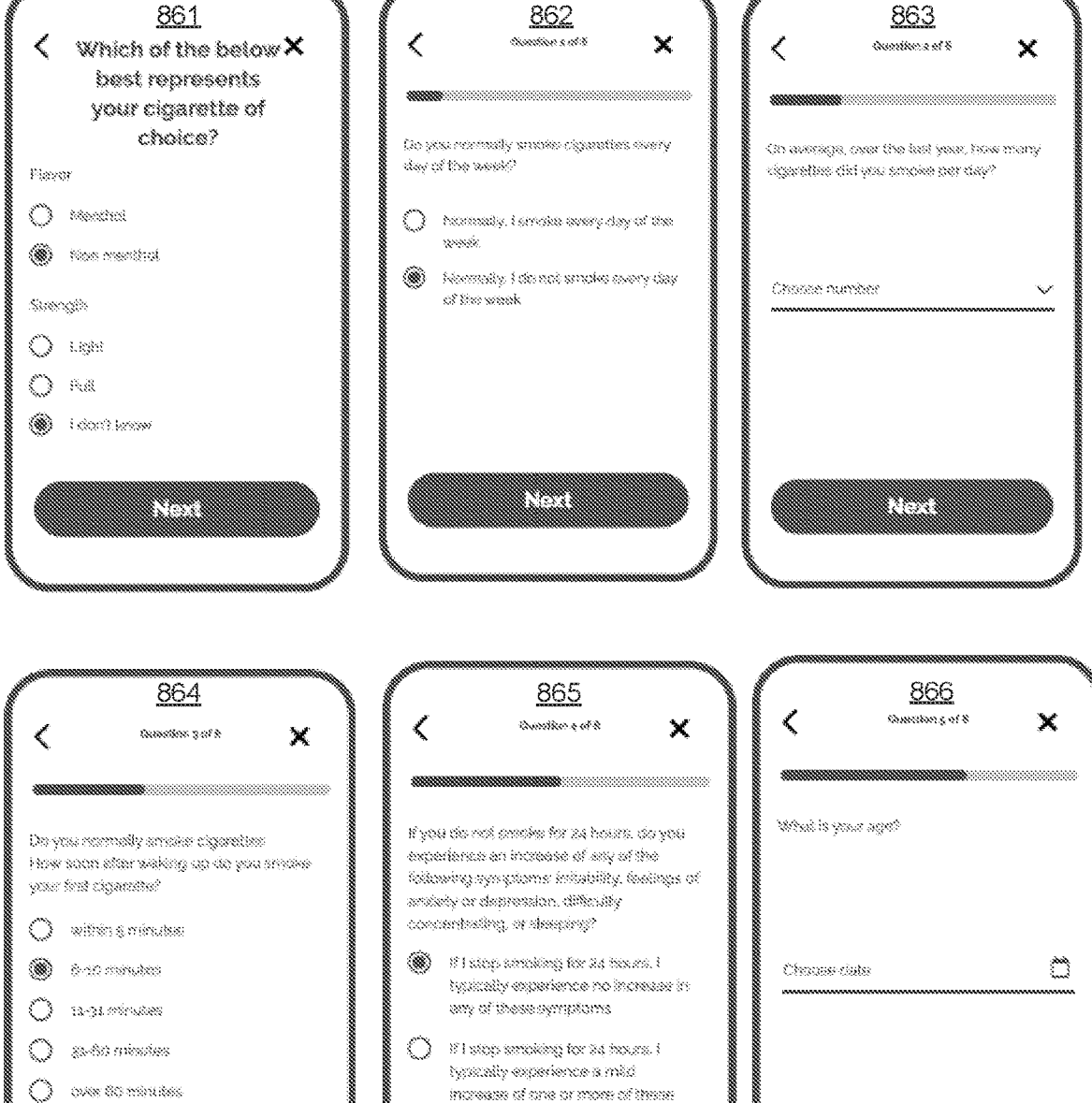
FIGS. 8C and 8D illustrate examples of user interfaces that are displayed on the user device during an on-boarding process according to some embodiments, where questions are presented to the user, input is received from the user relating to their smoking habits and personal information, and the input is used to tailor the treatment program (in this example, a smoking cessation program).
Figure 8D:
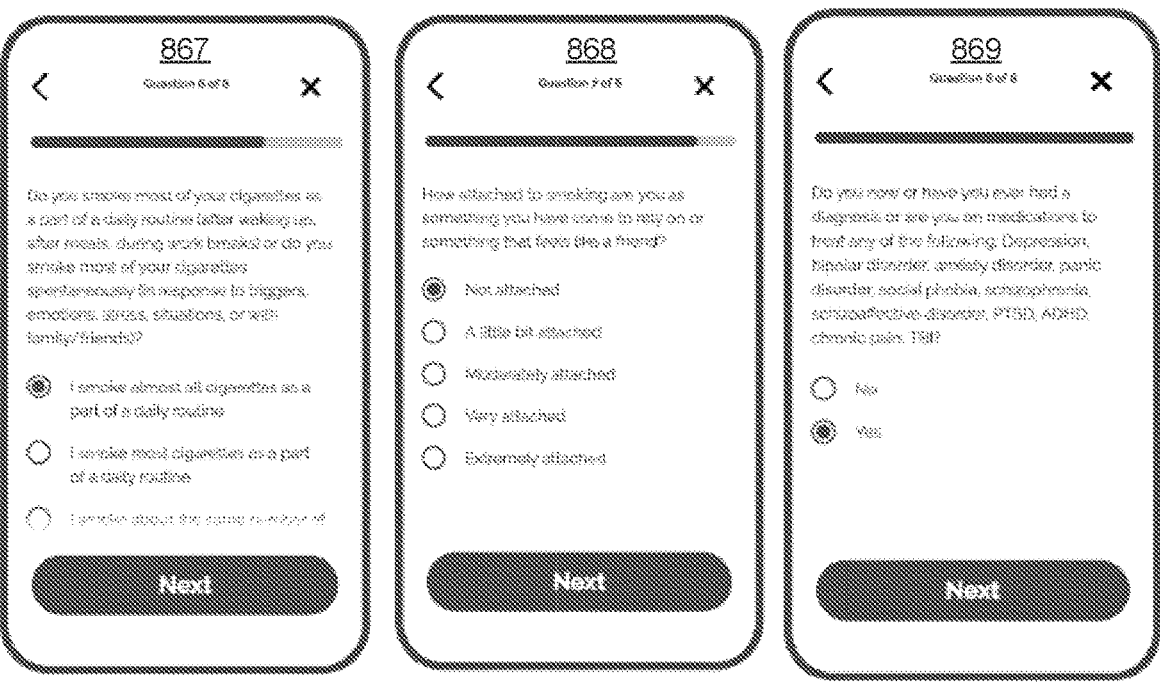
Figure 8D:
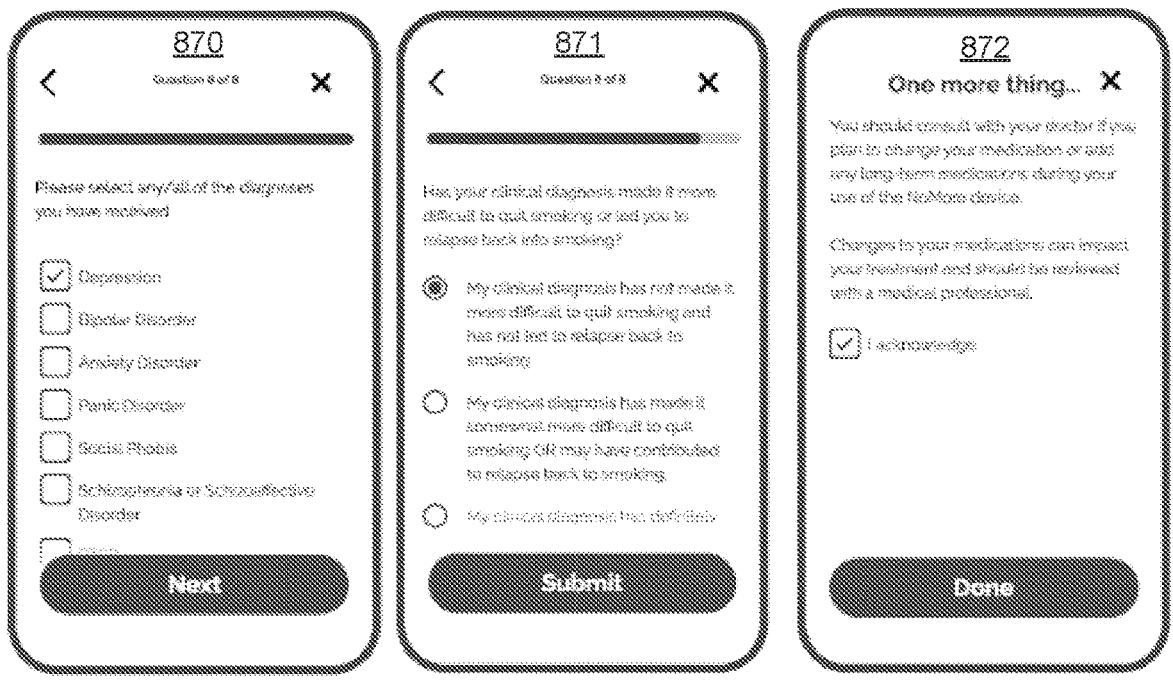

As discussed in reference to FIG. 8A, during onboarding 801 registration information specific to a user can be communicated from the user device 15 to the server system 25, and the treatment program can be based the information, according so some embodiments. FIGS. 8C and 8D illustrate examples of user interfaces 861-872 that can be displayed on the user device during an on-boarding process. In this process, questions are presented to the user, input is received from the user relating to their smoking habits and personal information, and the input can be used by the user device and the server system to tailor the treatment program (in this example, a smoking cessation program).

Figure 8E:
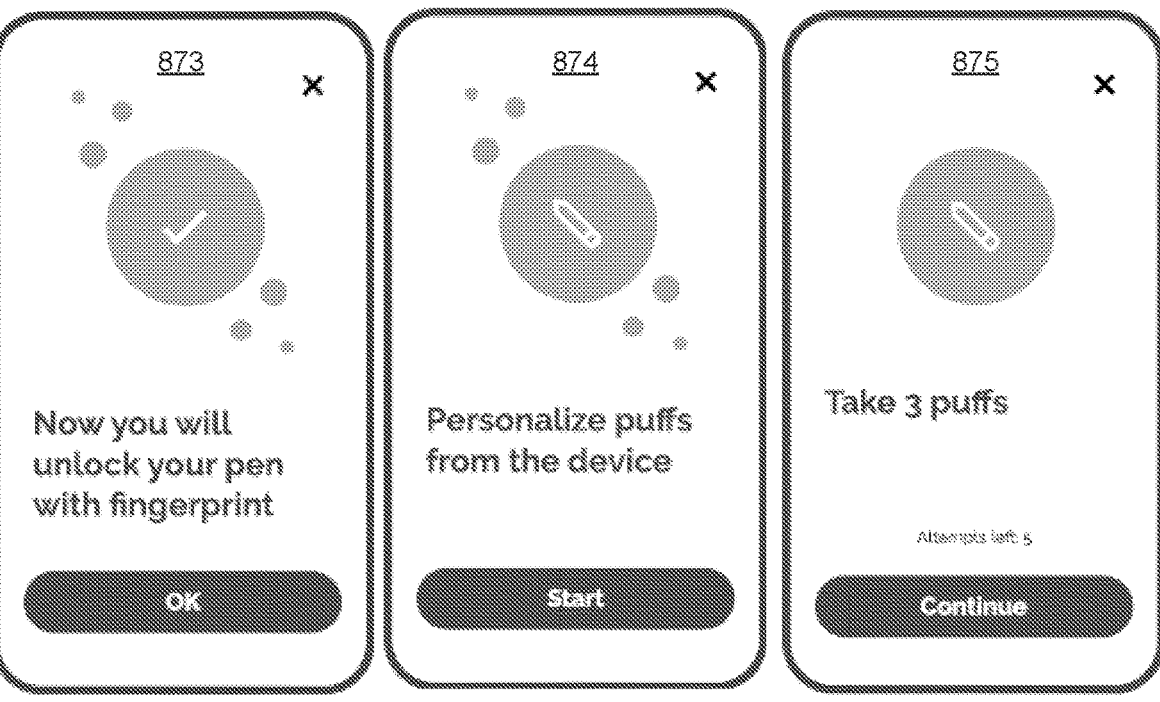
FIG. 8E illustrates examples of user interfaces that are displayed on the user device during a device personalization process (calibration process), according to some embodiments.
Figure 8E:
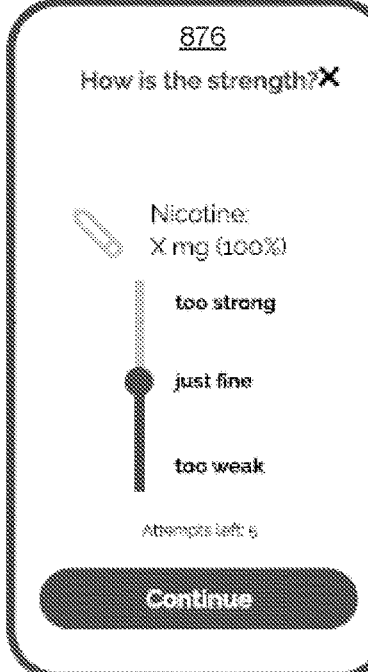
Figure 8E:

Calibration and configuration information is communicated from the server system 25 to the user device 15 and then to the delivery system 100 also as a part of onboarding the user into the treatment program. FIG. 8E illustrates examples of user interfaces that are displayed on the user device during a device calibration process, according to some embodiments. User interface (U/I) 873 prompts the user to unlock the delivery device using the fingerprint sensor. If fingerprint information has not yet been received from the user, it can also be done at this stage. U/I 874-877 personalize puff information for a user to calibrate the device to the specific user. Using the U/I' s, the process prompts the user to take a number of puffs using the delivery system and the delivery system monitors the puffs using the flow sensor. U/I 876 receives input from the user relating to the strength of the aerosol mixture that was received during the multiple puffs (e.g., three puffs). Multiple puffs can be used and the data averaged. The input can be used to change the way the aerosolizers are driven to tailor the strength of a "dose" as perceived by the user.

Figure 8F:
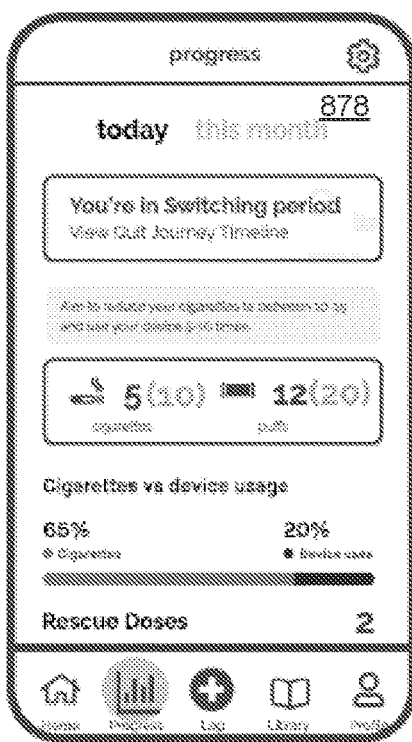
Figure 8F:
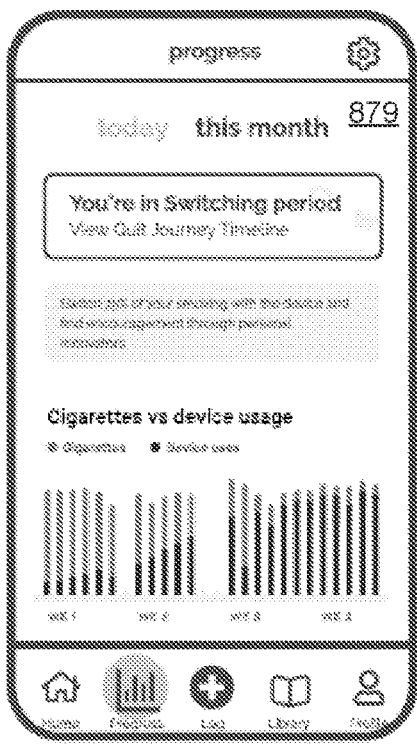
Figure 8F:
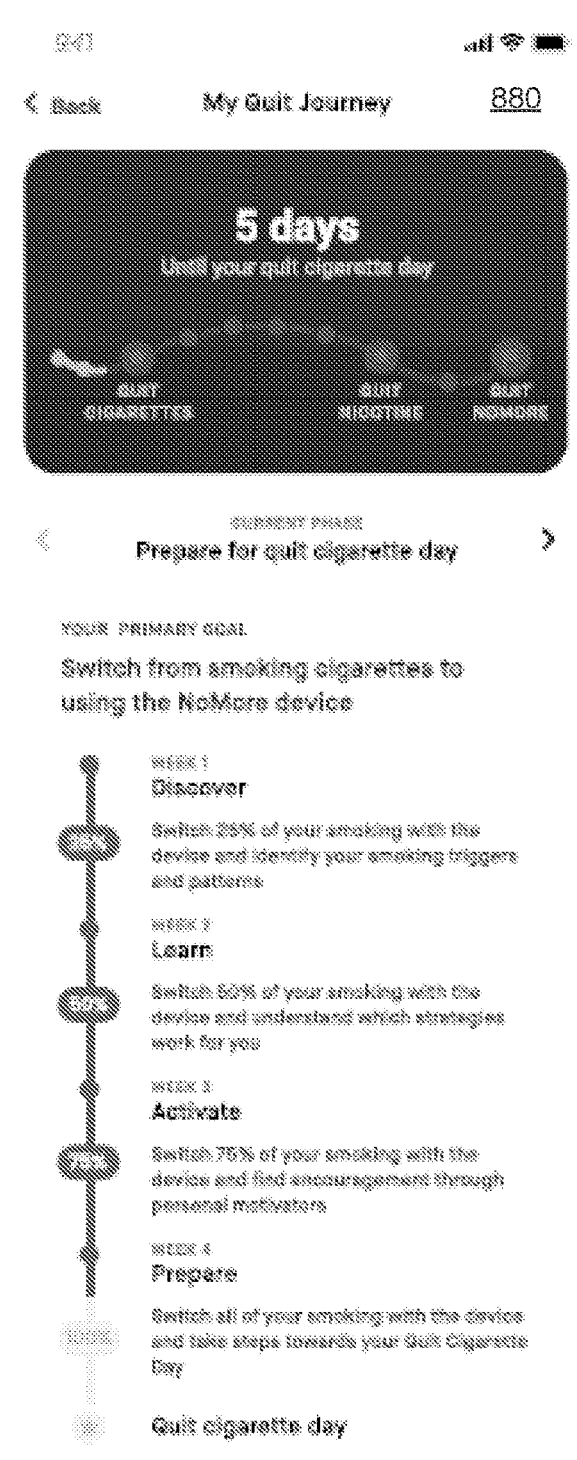

As an example, the treatment program can be a smoking cessation treatment program as illustrated in FIG. 7Q. After onboarding, during phase 1 of the treatment program 850, program data is communicated from the server system 25 to the user device 15, and from the user device 15 to the delivery system 100. In an example, the program data can include information that the controller circuit 130 uses to drive the aerosolizers 161*a-c* to generate aerosol mixtures comprising monoprotonated nicotine, freebased nicotine, and a flavor, and having a particular droplet size, for example, droplets having a diameter of less than or equal to 1.0 μm, according to the treatment program. During phase 1 of the treatment program 850, use data generated by the delivery system is communicated from the delivery device 100 to the user device 15 and then to the server system 25. The use data can also include any information that is sensed by the delivery system 109 based on the user's use of the delivery system 100 during the treatment program. In an example, the use data can include the number of puffs, the duration of each puff, sensed data from the delivery system 109 (e.g., data related to: air flow in/through delivery system (e.g., from flow sensor), ambient temperature, ambient pressure, fingerprint verification data, pod information (e.g., from the pod ID chip), blood oxygen sensed information, and/or carbon dioxide sensed information, information sensed from the user's saliva, etc.). In some embodiments, the use data can include information related to the amount of substances (e.g., fluids) that are in one or more of the containers of the pod 150. Also, in some embodiments, user data sensed by the sensor(s) 17 is communicated from the sensor(s) 17 to the delivery system 100 or the user device 15, and then it can be communicated to the server system 25, where it can be used to dynamically adjust the treatment program or monitor the patient's progress in the treatment program. The user data sensed by the sensor(s) 17 can include information related to any sensed characteristic of the user. For example, temperature, pH, sweat, sugar level in blood, nicotine level in blood, another characteristic of the user's blood, information from a pacemaker, and/or information related to an embedded sensor in the user. Information relating to the use of the delivery system and the user's progress in the treatment program can be illustrated in a U/I of the user device. FIG. 8F illustrates examples of user interfaces 878, 879, 880 that can be displayed on the user device during the treatment program, according to some embodiments.

As shown in FIG. 8B, the subsequent phases of the treatment program 851, 852 . . . are indicative of additional phases of a treatment program, for example, the cigarette taper 802, nicotine taper 803, placebo taper 804 phases illustrated in FIG. 7Q. During subsequent phases of the treatment program 851, 852 . . . additional program data related to the particular phase is communicated from the server system 25 to the user device 15, and from the user device 15 to the delivery system 100, and use data generated by the delivery system is communicated from the delivery device 100 to the user device 15 and then to the server system 25. In the subsequent phases of the treatment program 851, 852 . . . the program data can include information that the controller circuit 130 uses to drive the aerosolizers 161*a-c* to generate aerosol mixtures comprising monoprotonated nicotine, freebased nicotine, and a flavor, and having a particular droplet diameter, for example, droplets having a diameter of between less than or equal to 1.0 μm, to greater than 10 μm, according to the treatment program.

Also during these subsequent phases of the treatment program 851, 852 . . . , use data generated by the delivery system is communicated from the delivery device 100 to the user device 15 and then to the server system 25. The use data can include any information that is sensed by the delivery system 109. In an example, the use data can include the number of puffs, the duration of each puff, sensed data from the delivery system 109 (e.g., data related to: air flow in/through delivery system (e.g., from flow sensor), ambient temperature, ambient pressure, fingerprint verification data, pod information (e.g., from the pod ID chip), blood oxygen sensed information, and/or carbon dioxide sensed information, information sensed from the user's saliva, etc.). Also, in some embodiments, user data sensed by the sensor(s) 17 in the subsequent phases 851, 852 . . . is communicated from the sensor(s) 17 to the delivery system 100 or the user device 15, and then it can be communicated to the server system 25, where it can be used to dynamically adjust the treatment program or monitor the patient's progress in the treatment program. The user data sensed by the sensor(s) 17 can include information related to any sensed characteristic of the user. For example, temperature, pH, sweat, sugar level in blood, nicotine level in blood, another characteristic of the user's blood, information from a pacemaker, and/or information related to an embedded sensor in the user.

After all of the phases for the treatment program that include dynamically providing substances to the user in aerosol mixtures, in the final phase 853, the used device 15 provides app-based user support. In an example, the app-based user support can include positive reinforcement information and motivational information to help the user maintain the non-usage of nicotine products. During the final phase 853, questions may be provided to the user on the user device 15 to help determine how the user is feeling/handling not having nicotine, and information provided by the user is communicated back to the server system 25 and used to evaluate the user's progress in the treatment program. In some examples, information related to the final phase 853 from numerous users is collected by the server system and this data is used to make changes to the treatment program for future users. Also, in some embodiments, user data sensed by the sensor(s) 17 in the subsequent phases in the final phase 853 is communicated from the sensor(s) 17 to the delivery system 100 or the user device 15, and then it can be communicated to the server system 25, where it can be used to monitor the patient's adherence to the treatment program. The user data sensed by the sensor(s) 17 can include information related to any sensed characteristic of the user. For example, temperature, pH, sweat, sugar level in blood, nicotine level in blood, another characteristic of the user's blood, information from a pacemaker, and/or information related to an embedded sensor in the user.

Non-Thermal Aerosolizers

Drug delivery devices can include various types of aerosolizers. For example, thermal or non-thermal. Examples of non-thermal aerosolizers include mechanical (e.g., using a vibrating mesh) and jet nebulizers (e.g., using compressed air). Mesh nebulizers can use electricity to vibrate a piezo (at approximately ~128 KHz.) element that moves liquid formulations through a fine mesh to generate aerosol. The diameter of the mesh or aperture determines the size of the particle generated. Mesh nebulizers are very efficient and result in minimal residual volume (0.1-0.5 mL). Mesh nebulizers can utilize two basic mechanisms of action:

active vibrating mesh and passive mesh. Active vibrating mesh nebulizers have an aperture plate with 1,000-4,000 funnel-shaped holes vibrated by a piezo-ceramic element that surrounds the aperture plate. Passive mesh nebulizers (aerosolizers) utilize an ultrasonic horn to push fluid through a mesh. An adaptive aerosol delivery (AAD) system such as the I-neb® has a small, battery-powered, lightweight, and silent drug delivery device designed to deliver a precise, reproducible dose of drug. The aerosol is created by a passive mesh, and aerosol is injected into the breath at the beginning of inhalation. The dosage of the drug is controlled through specific metering chambers. The metering chambers can deliver a pre-set volume ranging from 0.25 to 1.7 mL with a residual volume of about 0.1 mL. Some systems use a AAD algorithm that pulses medication delivery into 50-80% of each inspiration, based on a rolling average of the last three breaths.

Another type of non-thermal aerosolizer is an ultrasonic nebulizer that uses ultrasound to create an aerosol. Ultrasonic nebulizers convert electrical energy to high-frequency vibrations using a transducer. These vibrations are transferred to the surface of the solution, creating a standing wave that generates aerosol (FIG. 10). Ultrasonic nebulizers were initially introduced as large-volume nebulizers most commonly used to deliver hypertonic saline for sputum inductions. Small-volume ultrasonic nebulizers are now commercially available for delivery of inhaled bronchodilators but should not be used with suspensions such as budesonide. Ultrasonic nebulizers tend to heat medication. This raises concerns about disrupting proteins, but that does not affect commonly inhaled medications.

Implementations of the drug delivery systems described herein (e.g., for smoking cessation or for delivery of other aerosolized drugs) can use non-thermal aerosolizers. FIGS. 9A-9F illustrate some examples of a drug delivery system that uses non-thermal aerosolizers. These drug delivery systems can be used in the system illustrated in FIG. 1 as the handheld delivery system, or other systems. These systems, devices, and methods are employed to properly deliver an uncontaminated dose of aerosolized medication or active pharmaceutical ingredient (API) to a user's respiratory system in a metered dose. Such systems deliver the medications directly to a user's respiratory system by aerosolizing a desired dose of the medication in liquid form. The user can inhale the aerosolized medication directly into the respiratory system, enabling faster treatment of various medical conditions. Delivery of accurate and consistent metered doses of aerosolized medication to a user is very important. Additionally, there is a need for real-time monitoring of drug delivery to a user that can be tracked and adjusted outside a doctor's office or medical setting.

The systems, devices, and methods disclosed herein address many of the same problems that were previously discussed with the smoking cessation device, but instead with respect to drug (medicant, active pharmaceutical ("API")) delivery. Current drug delivery systems often provide inconsistent doses by allowing some of the medication to remain in a reservoir in liquid form after the aerosolization process is completed. Sometimes the aerosolized medication is delivered with too great or too little force for substantially all the metered dose to properly enter the user's respiratory system. Contamination is also a pressing problem for many aerosolized drug delivery systems. Finally, enabling a medical advisor to monitor drug delivery and adjust dosage or schedule in real time would enable a user to receive more individualized and immediate care.

Due to the nature of many APIs and liquid medications, heat can have a destructive effect on the chemical composition. Therefore, turning the liquid medication into an aerosol through a non-thermal aerosol generator would be necessary to preserve the efficacy of the APIs. Similar to the cessation system discussed in prior embodiments, a handheld system can make the aerosolized API available to the user at any time or place. The system could be linked to an application and server in order for a medical professional to monitor or control the user's intake of API.

In one embodiment, the liquid medication containing an API may be stored in a container in connection with a mesh or membrane. A vibratable element vibrates the mesh for a metered amount of time causing aerosolization of the liquid medication from the container and subsequent movement of the aerosol down a passage into a mixing chamber. The amount of time the mesh is vibrated can change the amount of liquid medicant that is aerosolized. If multiple aerosol generators are used in the device, they can each be operated individually or in combination to create an aerosol mixture of multiple medications.

In another embodiment, a liquid reservoir between the container with the medicant and the mesh receives a metered dose of the medicant from the container. The mesh is then actuated to vibrate and turn the dose of liquid containing the API into an aerosol to be inhaled by the user.

Like the smoking cessation program, a drug dosage program can monitor a user's activity, collecting accurate and detailed information of a user's use of a drug delivery device as the user progresses through a dosage program. The collected information is related to use characteristics of the delivery device and includes information that that would be impossible for the user to collect themselves. In one embodiment, the user is "onboarded" where a dosage program is individually generated based on user individual characteristics that may be genetic, determined from a user interview, and/or testing. The generated program can include an individually tailored and dynamic dosage program for the user to be administered using a delivery system that includes a server-based system, which is running the dosage application. The dosage system can also include a mobile device, just like the cessation system, that communicates with the server-based system and provides information relating to the dosage program and the user's progress to the user. The drug delivery system may also include a delivery device, or inhalation device, that administers an aerosol mixture containing an API to the user based on the dosage program. The delivery device includes a plurality of sensors relating to its use, and signals from the sensors are used to monitor the user's progress through the delivery program, and the program id dynamically tuned as needed.

The delivery device and medicant containers can hold a plurality of APIs to be delivered to the patient. For example, the liquid API may comprise insulin, asthma medication, COPD treatments, hormone therapy, vaccines, pain relief treatment, or other protein formulations. Additionally, the delivery device may contain one, two, three, or more aerosol generators and containers, each holding a unique medication or aerosol component.

Referring back to FIG. 1, and similar as described above relating to thermal aerosolizers, the delivery system 10 may be used for drug dosage programming for a user where there is a server system 25, a delivery system 100 used by the user 30, and a computer/user device 15. One or more advisors or medical practitioners 35 can receive information relating to the drug dosage program and the use of the device. This system allows both the user 30 and the medical practitioner 35 to have real-time feedback on and control over the delivery of the API in the device. The doctor 35 may make changes depending on the user's response to the delivered drug or in response to changes in the user's medical status.

FIG. 9A illustrates an example of a delivery system 900 with mechanical aerosolizers. In various implementations, the delivery system 900 can include many or all of the same components as the previously described delivery system 100 that has thermal aerosolizers. The delivery system 900 includes a delivery device 909 and a pod 950, the pod 950 configured to be removably coupled to the delivery device 909. The delivery device 909 includes components to perform a treatment program that includes delivering multiple substances from the pod 950 in accordance with the treatment program. Specifically, the delivery device 909 controls multiple aerosolizers in the pod 950 to generate desired aerosol mixtures to be inhaled by the user, similar to the previously disclosed cessation system. When the pod 950 is coupled to the delivery device 909, the aerosolizer drivers in the delivery device electrically connect to corresponding aerosolizers in the pod 950. The aerosolizer drivers can independently and separately provide signals to each aerosolizer in the pod 950 and generate desired aerosol mixtures of the different substances in the multiple aerosolizers of the pod 950 in accordance with the treatment program. All or a portion of the pod 950 is positioned within the housing 902 when the pod 950 is coupled to the delivery device 909. In some examples, a portion of the pod 950 may be coupled to the delivery device 909 and extend from the proximal end 903 of the cessation device 909. In this example, the pod 950 is coupled to the cessation device 909 such that it is in electrical communication with the cessation device 909 and in fluid communication with air flow into and through the housing 902 (e.g., through opening 906, through channel 904, and through opening 908).

FIG. 9B illustrates the delivery device 909 coupled to the pod 950. FIG. 9C further illustrates the delivery device 909 (without the pod 950). These embodiments may be similar to that of the delivery device 109 and pod 150, containing many identical or similar components. However, in order to accommodate a non-thermal aerosol generator, the pod 950 does not have heating elements to turn the liquid into vapor. Instead, non-thermal aerosolizers are in place of the previous thermal elements. The non-thermal aerosolizers can include a vibrating mesh or other non-thermal aerosolizer components. In some embodiments, the pod 950 contains the majority of changes to accommodate non-thermal aerosolizers. The pod 950 is discussed in more detail in FIG. 9D.

FIG. 9D illustrates a pod 950 that utilizes non-thermal aerosolizers for a drug delivery device. Pod 950 may be used within a device such as illustrated in FIG. 9C. As FIG. 9C illustrates, pod 950 includes non-thermal aerosolizers 961a-c. Electrical connections 911a-c are each connected to one of the aerosolizers 961a-c, and can provide electrical power and/or control information to the aerosolizers 961a-c. When the pod 950 is coupled to the delivery device 909, the electrical connections 111a-c are coupled to the aerosolizer drivers 910a-c, respectively. Each aerosolizer 961 includes aerosol generating components 952, for example, a mesh, membrane, a mechanism to vibrate the mesh or membrane, or wave generating component. Containers 959a-c are configured to hold a substance (e.g., a fluid or powder containing an API) and are adjacent to a passage 956a-c having a distal end 955 and a proximal end 957. The passage provides a flow path for aerosol generated by the aerosol generating components 952 to flow to the mixing chamber 962. The mixing chamber 962 includes walls 966 enclose a mixing space 967. In the mixing chamber 962, the aerosol generated by the aerosolizer is readily available to a user to inhale through opening 964. In some embodiments, the pod 950 includes one or more power sources that can provide electrical power to electrical components of the pod 950. The controller circuit 930 can control the aerosolizer system to generate an aerosol as prescribed by the drug delivery system.

FIG. 9E is a schematic of a non-thermal example circuit 913 that can be used in a drug delivery system for a treatment program, which is similar to the controller circuit of device 109 illustrated in FIG. 4. This circuit 913 shows communication lines between a controller circuit 930 and other components of the delivery system. The controller circuit 930 can include one or more hardware processors, which can be the hardware processor 504 illustrated in FIG. 5. In this schematic, the airflow is from left to right such that intake of air is sensed by the flow sensor 912 and is received by the non-thermal aerosolizers 961. The aerosolizers 961 generate aerosol in the airflow, and the airflow then passes pressure sensors 958. FIG. 9E illustrates many components that are illustrated in FIG. 4, but with non-thermal aerosolizers in place of thermal aerosolizers. There may be more than one non-thermal aerosolizer present in the device. FIG. 9E also illustrates some additional components. For example, flash memory 910 is in communication with the controller circuit 930. The controller circuit 930 in this example includes a transceiver or other communication circuitry that is coupled to an antenna 920 which allows drug dosage circuit 913 to communicate with a smart phone or to another device or a network. As illustrated in FIG. 9E, the circuit 913 can also include a pod ID chip interface 465 (or aerosolizer chip interface) which, when the pod 950 is coupled to the delivery device 909, is in communication with a pod ID chip 963 of the pod 950 for providing signals (e.g., control signals) to the aerosolizer system and/or receiving information from the pod 950. The circuit 913 also includes the case data interface 425 which is in communication the controller circuit 930, and a case charge interface 430 which is in communication with a battery manager for 420 which manages power provided to the controller circuit 930 into a power source (e.g., battery) 914 to, for example, manage the charging of the battery 114.

FIG. 9F is a flowchart illustrating a process 990 for providing aerosol mixtures of dosages of drugs during a treatment program. At block 991, the process implements a treatment program on a handheld delivery system having a plurality of mechanical aerosolizers. In an example the delivery system is the delivery system 900, illustrated in FIG. 9B, that includes a handheld delivery device 909 and a pod 950. At block 992, the process 900 controls the plurality of mechanical aerosolizers to generate an aerosol mixture according to the treatment program, and based on signals received from one or more sensors of the delivery system. For example, a rescue button and/or an air flow sensor. The treatment program is typically over a period of time, and the period of time can include portions of time where certain drugs are provided in the aerosol mixture to a user. Various pods can be used during each portion of time of the treatment program to provide aerosol mixtures of different drugs to a user.

FIGS. 10A-10L illustrate further details of an example of a smoking cessation treatment program, such as the treatment program illustrated in FIG. 7Q. Specifically, FIGS. 10A-10L illustrate dosages that can be provided by a delivery system as described herein (e.g., as shown in FIG. 1) in accordance with a treatment program, where dosages of monoprotonated nicotine and freebase nicotine can be varied during the different time periods of the treatment program, and illustrate varying the aerosol droplet diameter during the treatment program so that the aerosol mixture is absorbed in the mouth, throat, or lungs. Using information provided from the user device and/or the server system, the delivery system controls the multiple aerosolizers to produce aerosol mixtures in accordance with the dosages in the different portions of a treatment program. For example, to generate aerosol mixtures having certain amount of each of two or three substances, and to generate aerosol mixtures having aerosol droplets of a certain diameter, during different portions of a treatment program. The term "dose" or "dosage" refers to the mass of active nicotine ingredient per single usage. The term "Dosage Map" refers to a precision medicine-based treatment program (e.g., a Predictably Human Therapeutic Process) that defines the variation of aerosol parameters during the treatment program, in an individualized manner that maximizes cessation efficacy. Variation of aerosol parameters permits initial duplication of the nicotine plasma pharmacokinetic (PK) response representing the patient's habituated nicotine source (cigarettes or vaping devices); and then gradual reduction of nicotine dose in a manner that minimizes triggering of patient withdrawal symptoms and urges by precise management of the nicotine plasma pharmacokinetics that are uniquely associated with a patient's phenotype and metabolic response to nicotine.

The term single usage refers to that of an "Experience" (cigarette) or a "Session" (vaping device). In this context, the single usage dose is the sum of all nicotine doses per puff over the total number of puffs taken by a patient, during an Experience/Session. Specifically, in these examples, the doses discussed in this application refer to the maximum possible mass of total nicotine comprised of monoprotonated nicotine and freebase nicotine species; that can be delivered during a single experience/session defined to consist of a maximum of 20 puffs from the device at some constant conversion of liquid mass to aerosol. This notion of dose is, by definition, an upper limit as to what will actually be delivered to a patient.

The actual dose delivered to the patient will be less than, but unlikely equal to, the maximum due to: a) aerosol losses that occur in the device due to condensation on device surfaces that form the fluid dynamic path of the aerosol, b) aerosol losses that occur at the device mouthpiece due to unsynchronized withdrawal of the device from the patient's mouth upon completion of a puff, and c) aerosol losses that may occur when a patient does not fully inhale the aerosol that was orally presented.

There are seven Quit Journey Periods during which the Device delivers Aerosol to a patient: a) Switching, b) Vigilance, c) Taper Start, d) Taper Continuation, e) Taper End, f) Low Nicotine, g) Device-Based Relapse Prevention There are six Aerosol Variables:

1. Total Nicotine Dose per Experience/Session—$TND_E$ (mg)=The sum of all nicotine species dosages over the number of Puffs taken by the Patient.
2. Monoprotonated Nicotine Dose fraction per Experience/Session—$MND_E$ (mg)=The fraction of Total Nicotine Dose due to Monoprotonated Nicotine.
3. Freebase Nicotine Dose fraction per Experience/Session—$FND_E$ (mg)=The fraction of Total Nicotine Dose due to Freebase Nicotine.
4. Aerosol Droplet Size per Experience/Session—$ADS_E$ (μm)=The Mass Mean Aerodynamic Diameter of aerosol droplets.

5. Freebase Nicotine Ratio per Experience/Session—$FNR_E$ (dimensionless)=The Ratio of Freebase Nicotine Dose to Total Nicotine Dose.
6. Enantiomeric Ratio per Experience/Session—$ENM_E$ (dimensionless)=The relative proportion of the nicotine enantiomer S fraction compared to the R fraction present in the Total Nicotine Dose.

FIG. 10A is a graph illustrating an example the quit journey period and the taper parameters implemented in a cessation program. The graph has one vertical axis and one horizontal axis. The vertical axis shows the total nicotine dose er experience in mg. The horizontal axis shows an example of periods for a smoking cessation treatment program. In this example there are seven periods—Switching Duration, Vigilance Duration, Start Duration, Continuation Duration, End Duration, No Nicotine Duration and Relapse Prevention Period, which are briefly described below:

Switching Duration: The start of the Quit Journey is the Switching Duration is the time during which patient is switching from the source (smoking cigarettes and vaping device) to a delivery system (e.g., a delivery system describe herein) used in the treatment program.

Vigilance Period: The Vigilance Period is the time during which patient quits using the source and continues to use the delivery system in their usual routine.

Start Duration: The Start Duration is the time during which the tapering starts using delivery system.

Continuation Duration: The Continuation Duration is the time during which the patient undergoes tapering continues using delivery device.

End Duration: The End Duration is the time during which the tapering stops using the delivery system.

No Nicotine Duration: The No Nicotine Duration is the time during which the patient maintains a low level of nicotine using delivery system.

Relapse Prevention Duration: The Relapse Prevention Duration is the time during which the delivery system is not used any more.

Still referring to FIG. 10A, this graph shows the starting dose of total nicotine at the start of the quit journey as $TND_{START}$ which is constant till the end of the Vigilance Duration. At the end of the Vigilance Duration to the end of the Start Duration, the total nicotine dose decreases at a constant rate to $RND_{E1}$#1. From the end of the Start Duration to the end of the Continuation Duration, the total nicotine dose is further reduced at a constant rate to $RND_{E2}$#2. From the end of the Continuation Duration to the end of the End Duration, the total nicotine dose is reduced at a constant rate to the targeted low nicotine dose, ε. From the start to the end of the No Nicotine Duration, the total nicotine dose is maintained at the target level, ε, and at the end of the duration, the use of nicotine is completely stopped. Then at the end of the Relapse Prevention Period, the use of the delivery system is stopped. This is followed by a software-based relapse prevention period. The delivery system is scheduled to be calibrated at different times: once at the start of the Switching Duration, once during the Switching Duration, once at the end of the Vigilance Duration, once at the end of the Start Duration, once at the end of the Continuation Duration, and once at the end of the End Duration, FIG. 10B illustrates the axis of the graphs illustrating an example of a dosage map specification. Each graph has three vertical axis and one horizontal axis. The horizontal axis shows the total cessation process duration periods 2-8 involving the delivery system. The cessation process duration periods 2-8 involving the delivery system can be divided into 7 periods: Switch Duration, Vigilance Duration, T-Start Duration, T-Continuation Duration, T-End Duration, Low Nicotine Duration and Relapse Prevention Duration. The Switch Duration is the time during which patient starts switching from smoking cigarettes and vaping device to delivery system. The Vigilance Duration is the time during which patient only uses the delivery system in their usual routine. The T-Start Duration is the time during which the tapering starts using delivery system. The T-Continuation Duration is the time during which the patient undergoes tapering continues using delivery system. The T-End Duration is the time during which the tapering stops using delivery system. The Low Nicotine Duration is the time during which the patient maintains a low level of nicotine using delivery system. The Relapse Prevention Duration is the time during which no more nicotine is given. FIG. 10B-1 illustrates the first axis on the top left side of the graph indicating the dose of monoprotonated nicotine in milligrams. The axis ranges from 3.0 to 0.0 mg. FIG. 10B-2 illustrates the second axis on the bottom left side of the graph indicating the dose of freebase nicotine in milligrams. The axis ranges from 0.0 to 3.0 mg. FIG. 10B-3 illustrates the third axis on the right side of the graph indicating the dimensionless ratio. This axis reads the dimensionless values of the Freebase Nicotine Ratio (FNR) and of the Enantiomeric Ratio. The axis ranges from a maximum value of 1.0 to a minimum value of 0.0.

FIG. 10C is a graph illustrating the hypothetical dosage map specification of monoprotonated nicotine dose. Both the vertical and horizontal axis are the same as described in FIG. 10B. In this hypothetical example the line 1001 shows how the dose of monoprotonated nicotine varies from 2.0 mg to 0.0 mg over the total cessation process duration period 2-8 of using the delivery system. From the start of the switching to the use of delivery system to the end of the T-Start, the amount of monoprotonated nicotine was a constant dose of 2.0 mg. Then from the end of the T-Start to the end of the T-Continuation, the amount of monoprotonated nicotine declined at a constant rate from 2.0 mg to 0.5 mg. From the end of the T-Continuation to the end of the T-End, the amount of monoprotonated nicotine was a constant dose of 0.5 mg. Then, from the end of the T-End to the end of the low nicotine period, the amount of monoprotonated nicotine declined at a constant rate from 0.5 mg to 0.0 mg. During the relapse prevention period, the amount of monoprotonated nicotine remained at 0.0 mg.

FIG. 10D is a graph illustrating the hypothetical dosage map specification of freebase nicotine dose (FND). Both the vertical and horizontal axis are the same as described in FIG. 10B. In this hypothetical example the dashed line 1002 shows that the dose of freebase nicotine. In this graph, the dose of freebase nicotine remained at a constant of 0.8 mg during the entire total cessation process duration period 2-8 of using the delivery system.

FIG. 10E is a graph illustrating an example of a hypothetical dosage map specification of total nicotine dose (TND) (i.e., the sum of monoprotonated nicotine and freebase nicotine). Both the vertical and horizontal axis are the same as described in FIG. 10B. In this hypothetical example the dotted line 1001 shows the how the dose of monoprotonated nicotine varies from 2.0 mg to 0.0 mg and the dashed line 1002 shows how the dose of freebase nicotine remained at a constant of 0.8 mg over the total cessation process of using the delivery system. From the start of the switching to the use of delivery system to the end of the T-Start, the TND was a constant dose of 2.8 mg. Then from the end of the T-Start to the end of the T-Continuation, the TND declined at a constant rate from 2.8 mg to 1.3 mg. From the end of the T-Continuation to the end of the T-End, the TND was a constant dose of 1.3 mg. Then, from the end of the T-End to the end of the low nicotine period, the TND declined at a constant rate from 1.3 mg to 0.8 mg. During the relapse prevention period, the TND remained at 0.8 mg.

FIG. 10F is a graph illustrating the hypothetical dosage map specification of freebase nicotine ratio (FNR) (ratio of (freebase nicotine dose)/(total nicotine dose)). This graph can be used to calculate the FNR of the patient over the cessation process duration of using the delivery system. Both the vertical and horizontal axis are the same as described in FIG. 10B. The FNR value can be read from the vertical axis on the right side which gives dimensionless ratio. In this hypothetical example the light dotted line 1001 shows how the dose of monoprotonated nicotine varies from 2.0 mg to 0.0 mg. The light dashed line 1002 shows how the dose of freebase nicotine remained at a constant of 0.8 mg and the large dashed line 1003 shows how FNR varies from 0.29 to 1.0 over the total cessation process duration using the delivery system. During the start of the switching to the use of delivery system to the end of the T-Start, the FNR equals to 0.29. Then from the end of the T-Start to the end of the T-Continuation, the FNR increased to 0.62 at a constant rate. From the end of the T-Continuation to the end of the T-End, the FNR remained constant at 0.62. Then, from the end of the T-End to the end of the low nicotine period, the increased to 1.0 at a constant rate. During the relapse prevention period, the FNR remained constant at 1.0.

FIG. 10G is a graph illustrating the hypothetical dosage map specification of enantiomeric ratio (ratio of (S-nicotine)/(R-nicotine)). This graph can be used to show the Enantiomeric ratio, i.e., the ratio of the different enantiomer of the nicotine used by the patient over the total cessation process duration of using the delivery system. Both the vertical and horizontal axis are the same as described in FIG. 10B. The Enantiomeric ratio value can be read from the vertical axis on the right side which gives dimensionless ratio. In this hypothetical example the light dot and dashed line 1004 shows how the Enantiomeric ratio remained at a constant of 0.99 over the total cessation process duration period of using the delivery system.

FIG. 10H is a graph illustrating the hypothetical dosage map specification of variable aerosol droplet size (ADS). Both the vertical and horizontal axis are the same as described in FIG. 10B. In this hypothetical example the dotted line 1001 shows how the dose of monoprotonated nicotine varies from 2.0 mg to 0.0 mg and the dashed line 1002 shows how the dose of freebase nicotine remained at a constant of 0.8 mg over the total cessation process duration period of using the delivery system. From the start of the switching to the use of delivery system to the end of the T-Continuation, the ADS is less than or equal to 1.0 μm as shown in the clear area between line 1001 of the monoprotonated and line 1002 of the freebase nicotine dose. Then from the end of the T-Continuation to the end of the relapse prevention period, the size of the ADS increases to great than or equal to 10.0 μm as shown in the yellow area between the line 1001 of the monoprotonated and line 1002 of the freebase nicotine dose.

FIG. 10I is a graph illustrating an example of a hypothetical dosage map specification of combined previous six taper variables shown as a function of the quit journey period, based on initial values of TND, FND and FNR, plus taper TND reduction targets. This is a graph which shows all the variables which are collected and calculated to reach the target of the reduced TND. Both the vertical and horizontal axis are the same as described in FIG. 10B. In this hypothetical example line 1001 shows the varying dose of monoprotonated nicotine from 2.0 mg to 0.0 mg, line 1002 shows the constant dose of freebase nicotine at 0.8 mg, line 1003 shows varying FNR from 0.29 to 1.0 and line 1004 shows constant Enantiomeric ratio remains at 0.99 over the total cessation process duration period 2-8 of using the delivery system. This graph indicates that with a constant FND, as the dose of monoprotonated nicotine decreases, the TND also decreases, but the FNR increases, and the enantiomeric ratio remains constant during the total cessation process duration period of using the delivery system.

FIG. 10J is a graph illustrating the representative dosage map specification of a cigarette-smoking patient (Patient 1—Marlboro Red@ 2.6 mg/cig with FNR=0.11, Taper regime $T_{FND}$ (FNR constant)). Both the vertical and horizontal axis are the same as described in FIG. 10B. In this example, in the beginning, Patient 1 smokes a typical full-flavor lit end cigarette which has a high dose of monoprotonated nicotine, $MPD_E$, of 1.78 mg, relatively low free base nicotine, $FND_E$, of 0.22 mg and the $ADS_E$ is less than or equal to 1.0 μm. For Patient 1, the $FND_E$ has a constant value of 0.11 shown by line 1003 and the enantiomeric ratio, ENM, has a constant value of 0.99 shown with line 1004, from start of the switching to the use of delivery system to the end of the Low nicotine period of using the delivery system. The TND is the area under lines 1001 and 1002. From the start of the switching to the use of delivery system to the end of the Vigilance Period, the $TND_E$ is 2.0 mg. From the start of T-Start to the end of Low Nicotine period, the TND decreases from 2.0 mg and during the relapse prevention period, the TND is 0.0 mg. Towards the end cessation process, Patient 1 has very low dose of nicotine, maintains freebase ratio for sensory response and the ADS is increased to reduce absorption.

FIG. 10K is a graph illustrating the representative dosage map specification of a vaping patient (Patient 2—Vaporesso XROS & Zen-Haus e-Liq@ 17 mg/mL with FNR=0.84, Taper regime $T_{FND}$(FNR constant)). Both the vertical and horizontal axis are the same as described in FIG. 10B. In this example, in the beginning, Patient 2 smokes a typical vaping device which has a modest dose of monoprotonated nicotine, $MPD_E$, of 0.25 mg, high free base nicotine, $FND_E$, of 0.99 mg and the $ADS_E$ is greater than or equal to 10.0 μm. For Patient 2, the $FND_E$ has a constant value of 0.84 shown by line 1003 and the enantiomeric ratio, ENM, has a constant value of 0.99 shown by line 1004, from start of the switching to the use of delivery system to the end of the Low nicotine period of using the delivery system. The TND is the area under lines 1001 and 1002. From the start of the switching to the use of delivery system to the end of the Vigilance Period, the $TND_E$ is 1.24 mg. From the start of T-Start to the end of Low Nicotine period, the TND decreases from 1.24 mg and during the relapse prevention period, the TND is 0.0 mg. Towards the end cessation process, Patient 2 has very low dose of nicotine, maintains freebase ratio for sensory response and the ADS is kept same throughout the process.

FIG. 10L is a graph illustrating the representative dosage map specification of a cigarette-smoking patient (Patient 3—Winston Blue@ 1.7 mg/cig with FNR=0.05, Taper regime $T_{FND}$ initial (FNR constant) $T_{FNR}$(FND constant)). Both the vertical and horizontal axis are the same as described in FIG. 10B. In this example, initially the FNR is constant and later the FND is constant. In the beginning, Patient 3 smokes a typical mild lit-end cigarette which has a moderate dose of monoprotonated nicotine, $MPD_E$, of 1.78 mg, relatively low free base nicotine, $FND_E$, of 0.22 mg and the $ADS_E$ is less than or equal to 1.0 μm. For Patient 3, the enantiomeric ratio, ENM, has a constant value of 0.99 from start of the switching to the use of delivery system to the end of the Low nicotine period of using the delivery system. The TND is the area under lines 1001 and 1002. From the start of the switching to the use of delivery system to the end of the Vigilance Period, the $TND_E$ is 2.0 mg. From the start of T-Start to the end of Low Nicotine period, both monoprotonated and freebase nicotine dose decreases, and the TND decreases from 2.0 mg and during the relapse prevention period, the TND is 0.0 mg. The $FND_E$ has a constant value of 0.11 from start of the switching to the use of delivery system to the end of the T-Continue period. Then from the start to the end of the T-End period, FNR increases at a constant rate from 0.11 to 1.0 and remains constant from the start to the end of the low nicotine period. Towards the end cessation process, Patient 3 has very low dose of nicotine, maintains freebase ratio for sensory response and for maximum bioavailability and the ADS is small for slow absorption.

FURTHER EXAMPLES

This disclosure includes numerous examples of drug delivery systems. Such systems can be implemented with thermal or non-thermal aerosolizer systems. In one example, a drug delivery system, includes a housing having a distal end and a proximal end, a channel in the housing, the channel for receiving air, and an opening for communicating air to an aerosolizer pod coupled to the housing; an aperture on the proximal end of the housing configured to receive the aerosolizer pod therein. In some implementations, the housing configured to at least partially surround the aerosolizer pod when the aerosolizer pod is positioned in the housing. The system can include a flow sensor positioned to sense air flowing through the channel, a power source, and a controller circuit coupled to the power source, the controller circuit comprising a hardware controller coupled to the flow sensor, the aerosolizer system, and the rescue button, the hardware controller including a hardware processor and a non transitory computer readable medium in communication with the hardware controller, the computer readable medium configured to store dosage program information, and to store executable instructions that, when executed, configure the hardware controller to perform a dosage program that includes receiving input signals from the flow sensor and the rescue button, and individually controlling the aerosolizer system to provide aerosolizer generation signals to control the aerosol generator of the aerosolizer pod to generate an aerosol mixture based at least on the received input signals and the dosage program information. The delivery system can further include the aerosolizer pod, wherein the aerosolizer pod has a distal end and a proximal end, and includes an intake port on the distal end for receiving air flowing through the channel, an exhaust port on the proximal end for communicating the aerosol mixture out of the aerosolizer pod, and an aerosolizer system comprising a first, second, and third aerosolizer, the first, second, and third aerosolizers including an electrical connection that electrically couples to the first, second, and third aerosol drivers, respectively, when the aerosolizer pod is received into the housing. The first, second, and third aerosolizers can also include a mechanical aerosolizer. The mechanical aerosolizer can include a membrane. The mechanical aerosolizer can be configured to vibrate the membrane. In some examples, the mechanical aerosolizer can include a piezo-electric mechanism to vibrate the membrane. The membrane can be positioned between the medicant in the container and the channel in the housing. When activated, the mechanical aerosolizer can use the membrane to turn a dose of the medicant into an aerosol that is inhalable by a user.

System Implementation

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums). Computer readable storage mediums may also be referred to herein as computer readable storage or computer readable storage devices.

A non-transitory computer readable storage medium can be a tangible device that can retain and store data and/or instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA)

instructions, machine instructions, machine dependent instructions, microcode, firmware instructions, state-setting data, configuration data for integrated circuitry, or either source code or object code written in any combination of one or more programming languages, including an object oriented programming language such as Java, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

As described above, in various embodiments certain functionality may be accessible by a user through a web-based viewer (such as a web browser), or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets). Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

Example Embodiments

Embodiment 1: A system, comprising: a delivery device including a housing; a channel in the housing, the channel structured to receive air from an opening in the housing and communicate air to an aerosolizer pod coupled to the delivery device; a flow sensor positioned to sense air flowing through the channel; a first, second, and third aerosolizer driver each having an electrical connection configured to electrically couple to a first, second, and third aerosolizer, respectively, of an aerosolizer pod coupled to the delivery device; and a controller circuit coupled to a power source, the controller circuit comprising a transceiver and a hardware controller electrically coupled to the first, second, and third aerosolizer drivers, and the flow sensor, the controller circuit configured to individually control the first, second, and third aerosolizer drivers to provide aerosol generation signals to a first, second and third aerosolizer to generate an aerosol mixture based at least in part on a treatment program received using the transceiver; and a user computing device comprising an application in communication with the delivery system via the transceiver.

Embodiment 2: The treatment program system of embodiment 1, further comprising a server system configured with a hardware processor and non-transitory computer readable storage media encoded with a treatment program including instructions executable by an operating system to control the generation of the aerosol mixtures over time according to the treatment program, and provide treatment program information to the delivery system to control the generation of the aerosol mixture by the delivery system.

Embodiment 3: The system of embodiment 2, wherein the treatment program information provided to the delivery system includes information to individually control the first, second, and third aerosolizer drivers to provide signals to a first, second and third aerosolizer coupled to the first, second and third aerosolizer drivers, respectively, to generate a desired aerosol mixture of a first aerosol generated from a first substance, a second aerosol generated by a second substance, and a third aerosol generated by a third substance.

Embodiment 4: The system of any one of embodiments 1-3, wherein the treatment program information provided to the delivery system includes information to individually control the first, second, and third aerosolizer drivers to provide signals to a first, second and third aerosolizer coupled to the first, second and third aerosolizer drivers to generate the first, second and third aerosol having an aerosol droplet of a certain diameter.

Embodiment 5: The system of any one of embodiments 1-4, wherein the treatment program information provided to the delivery system includes information to individually control the first, second, and third aerosolizer drivers to provide signals to a first, second and third aerosolizer coupled to the first, second and third aerosolizer drivers to generate the first, second and third aerosol having an aerosol droplet of a first diameter for a first portion of time and an aerosol droplet of a second diameter for a second portion of time.

Embodiment 6: A method for smoking cessation, the method comprising: providing a delivery system including: a delivery device including a housing; a channel in the housing, the channel structured to receive air from an opening in the housing and communicate air to an aerosolizer pod coupled to the delivery device; a flow sensor positioned to sense air flowing through the channel; a first, second, and third aerosolizer driver configured to electrically couple to a first, second, and third aerosolizer, respectively, of an aerosolizer pod coupled to the delivery device; a rescue button configured to, when actuated by a user, provide a signal indicative of the user's need for an additional dose of an aerosol mixture; a power source; and a controller circuit coupled to the power source, the controller circuit comprising a hardware controller electrically coupled to the first, second, and third aerosolizer drivers, the flow sensor, and the rescue button, the hardware controller including a hardware processor and a non-transitory computer readable medium in communication with the hardware controller, the computer readable medium configured to store treatment program information, and to store executable instructions that, when executed, configure the hardware controller to individually control the three aerosolizer drivers to provide aerosol generation signals to first, second and third aerosolizers, respectively, of a pod coupled to the delivery device to generate an aerosol mixture based at least in part on the stored treatment program for quitting smoking, and information that is received from the flow sensor and the rescue button; and an aerosolizer pod, the aerosolizer pod comprising: an aerosolizer system including the first, second, and third aerosolizers, wherein the pod is structured to be removably coupleable to the delivery device, each of the first, second, and third aerosolizers having an electrical connection that electrically couples to one of the first aerosolizer, second aerosolizer, and third aerosolizer drivers of the delivery device; a first container holding a first substance, a second container holding a second substance, and a third container holding a third substance, the first, second and third containers structured to provide the first, second and third substances to the first, second, and third aerosolizers, respectively, wherein the first substance is freebase nicotine and the second substance is monoprotonated nicotine; and generating aerosol mixtures in accordance with a smoking cessation treatment program to generate aerosol mixtures that are dynamically changed over a period of time to have different aerosol drop sizes and different concentrations of the first, second and third substances based at least in part on received signals from the flow sensor and the rescue button, and on smoking cessation treatment program information stored in the non-transitory computer readable medium.

Embodiment 7: A method for smoking cessation, the method comprising: providing signals, from a hardware controller in a hand-held delivery device, to a first, second and third aerosolizer driver in the delivery device to dynamically control a first, second and third aerosolizer in a pod coupled to the delivery device, to generate aerosol mixtures that are dynamically changed over a period of time to have different aerosol droplet sizes and different concentration of a first, second and third substance in containers of the pod based at least in part on received input signals from one or more of a flow sensor and smoking cessation treatment program information stored in a non-transitory computer readable medium coupled to the hardware controller, wherein the method is executed by the controller executing computer executable instructions stored on the non-transitory computer readable medium, wherein the executable instructions when executed cause the hardware controller to providing signal to the first, second, and third aerosolizer drivers according to the smoking cessation program.

Embodiment 8: A delivery system for providing an aerosol mixture in a treatment program for quitting smoking, comprising: a pod comprising an aerosolizer system including a first, second, and third aerosolizers, and a first, second and third container in communication with the first, second, and third aerosolizer, respectively, each container holding a substance that is used to generate an aerosol mixture according to the treatment program; a delivery device, wherein the pod is removably coupleable to the delivery device, the delivery device including a housing; a channel structured to receive air from an opening in the housing and communicate air to an aerosolizer pod coupled to the delivery device; a flow sensor positioned to sense air flowing through the channel; a first, second, and third aerosolizer driver configured to electrically couple to the first, second, and third aerosolizer, respectively, of the pod when the pod is coupled to the delivery device; a rescue button configured to, when actuated by a user, provide a signal indicative of the user's need for an additional dose of an aerosol mixture; a power source; and a controller circuit coupled to the power source, the controller circuit comprising a hardware controller electrically coupled to the first, second, and third aerosolizer drivers, the flow sensor, and the rescue button, the hardware controller including a hardware processor and a non-transitory computer readable medium in communication with the hardware controller, the computer readable medium configured to store treatment program information, and to store executable instructions that, when executed, configure the hardware controller to individually control the three aerosolizer drivers to provide aerosol generation signals to the first, second and third aerosolizers, respectively, to generate an aerosol mixture based at least in part on the stored treatment program, and information that is received from the flow sensor and the rescue button.

Embodiment 9: The delivery system of embodiment 8, wherein the three aerosolizers are thermal aerosolizers.

Embodiment 10: The delivery system of embodiment 8, wherein the three aerosolizers are mechanical aerosolizers.

Embodiment 11: The delivery system of embodiment 8, wherein the first container contains freebase nicotine, and the second container contains monoprotonated nicotine.

Embodiment 12: A computer-implemented method for providing a treatment program for smoking cessation, the method comprising: generating a smoking cessation treatment program that includes a plurality of treatment periods based on received patient information, the patient information including a nicotine metabolic rate; communicating aerosol mixture information, based on the treatment program, to a handheld delivery system that includes three substances which are used to generate an aerosol mixture that is provided to the patient, the aerosol mixture information indicating, for each of the plurality of treatment periods, an amount of each of the three substances to be included in the aerosol mixture and the droplet size of the aerosol droplets in the aerosol mixture, wherein the method is performed by one or more computer hardware processors executing a plurality of computer readable instructions stored on a non-transitory computer memory.

Embodiment 13: The method of embodiment 12, further comprising generating, on the delivery system, the aerosol mixture based on the aerosol mixture information.

Embodiment 14 The method of any one of embodiments 12 or 13, further comprising receiving usage information from the delivery system, and communicating to the delivery system updated aerosol mixture information, based at least in part on the usage information.

Embodiment 15: A computer-implemented method for providing substances to a user, the method comprising: providing aerosol generation information to a hand-held delivery device that includes three aerosolizer drivers, wherein the aerosol generation information is based on a treatment program generated based on user inputs and test data of the user's nicotine metabolic rate (NMR); and generating different aerosol mixtures for inhalation by the user over a period of time by providing drive signals from three aerosolizer drivers to control three aerosolizes to produce the aerosol mixtures having a composition of three substances and to control the three aerosolizers to produce aerosol having a aerosol droplet diameter, according to the treatment program.

Embodiment 16: The method of embodiment 15, wherein the aerosol generation information is provided to the hand-held delivery device from a user device.

Embodiment 17: The method of embodiment 16, wherein the user device is a mobile computer device.

Embodiment 18. The method of embodiment 16, wherein the user device is a smart phone, tablet computer, or a laptop computer.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended embodiments rather than by the foregoing description. All changes which come within the meaning and range of equivalency of the embodiments are to be embraced within their scope.

What is claimed is:

1. A delivery system for providing an aerosol mixture in a treatment program, comprising:
a delivery device including
a channel structured for communicating air to a pod coupled to the delivery device;
a flow sensor positioned to sense air flowing through the channel;
two or more aerosolizer drivers;
a controller circuit comprising a hardware controller electrically coupled to the two or more aerosolizer drivers and the flow sensor, the hardware controller including a hardware processor and a non-transitory computer readable medium in communication with the hardware controller, the computer readable medium configured to store treatment program information, and to store executable instructions that, when executed, configure the hardware controller to individually control the two or more aerosolizer drivers to provide aerosol generation signals for two or more aerosolizers to generate aerosol mixtures that are dynamically changed over a period of time to have different predetermined aerosol drop sizes and different predetermined concentrations of a first substance and a second substance based at least in part on the stored treatment program and information that is received from the flow sensor.

2. The delivery system of claim 1, wherein the delivery device further includes a housing comprising an aperture to receive the pod.

3. The delivery system of claim 1, further comprising the pod structured to be removably coupleable to the delivery device, wherein the pod includes two or more containers each holding a substance used to create the aerosol mixture.

4. The delivery system of claim 3, wherein the pod comprises an ID chip, and wherein the delivery device further comprises an aerosolizer pod interface configured to sense the ID chip and communicate the ID chip to the hardware controller to identify the aerosolizer pod and the substances contained therein.

5. The delivery system of claim 3, wherein the delivery device further comprises a rescue button configured to, when actuated, provide a signal to provide an additional dose of the aerosol mixture according to the treatment program, and wherein the executable instructions, when executed, further configure the hardware controller to individually control the two or more aerosolizer drivers to provide aerosol generation signals for the two or more aerosolizers to generate the aerosol mixture based at least in part on information received from the rescue button.

6. The delivery system of claim 3, wherein the two or more aerosolizers include a first aerosolizer and a second aerosolizer, and wherein the two or more containers include a first container holding a first substance, and a second container holding a second substance, the first and second containers structured to provide the first and second substances to the first aerosolizer and the second aerosolizer, respectively, when the pod is coupled to the delivery device.

7. The delivery system of claim 6, wherein the first substance comprises freebase nicotine, and the second substance comprises monoprotonated nicotine.

8. The delivery system of claim 6, wherein the two or more aerosolizers further comprises a third aerosolizer, and wherein the pod further comprises a third container holding a third substance, the third container structured to provide the third substance to the third aerosolizer when the pod is coupled to the delivery device.

9. The delivery system of claim 8, wherein the third substance comprises a flavorant.

10. The delivery system of claim 3, wherein the pod comprises:
a distal end and a proximal end;
an intake port on the distal end for receiving the air flowing through the channel;
a mixing chamber; and
an exhaust port on the proximal end for communicating the aerosol mixture from the mixing chamber out of the pod.

11. The delivery system of claim 10, wherein the mixing chamber includes intake openings in fluid communication with the two or more aerosolizers, and the pod is structured such that aerosol generated by the two or more aerosolizers can enter the mixing chamber via the intake openings, mix together, and be communicated out of the pod via the pod exhaust port.

12. The delivery system of claim 1, further comprising the two or more aerosolizers, wherein the two or more aerosolizers include a first non-thermal mechanical aerosolizer and a second non-thermal mechanical aerosolizer.

13. The delivery system of claim 12, wherein the two or more aerosolizers each include a mesh having a plurality of apertures.

14. The delivery system of claim 1, wherein the controller circuit further comprises a transceiver, wherein the controller circuit is configured to receive treatment program information using the transceiver, and wherein the controller circuit is configured to provide signals to generate the aerosol mixture based on the received treatment program information.

15. The delivery system of claim 14, wherein the controller circuit is further configured to provide signals to generate the aerosol mixture having a certain aerosol droplet size, from each of the two or more aerosolizers based on the received treatment program information.

16. The delivery system of claim 15, wherein the controller circuit is further configured to provide signals to generate the aerosol mixture having droplets of less than or equal to a first diameter from each of the two or more aerosolizers for a first portion of the treatment program, and to provide signals to generate the aerosol mixture having droplets of greater than or equal to a second diameter from each of the two or more aerosolizers for a second portion of the treatment program.

17. A delivery system for providing an aerosol mixture in a treatment program, comprising:
a delivery device including
two or more aerosolizer drivers; and
a controller circuit comprising a hardware controller electrically coupled to the two or more aerosolizer drivers, the hardware controller including a hardware processor and a non-transitory computer readable medium in communication with the hardware controller, the computer readable medium configured to receive and store treatment program information, and to store executable instructions that, when executed, configure the hardware controller to individually control the two or more aerosolizer drivers to provide aerosol generation signals for generating aerosol mixtures that are dynamically changed over a period of time to have different predetermined aerosol drop sizes and different predetermined concentrations of a first substance and a second substance based at least in part on the stored treatment program.

18. The delivery system of claim 17, wherein the delivery device further comprising a housing, the delivery system further comprising a pod removably coupleable to the housing of the delivery device, wherein the pod comprises a mixing chamber structured with multiple intake openings for receiving aerosol generated from aerosolizers controlled by the two or more aerosolizer drivers, and an exhaust port for communicating the aerosol mixture from the mixing chamber out of the pod.

19. The delivery system of claim 18, the aerosolizers comprising two or more aerosolizers, each one of the two or more aerosolizers coupled to one of the two or more aerosolizer drivers, and wherein the pod further comprises a first container holding a first substance and a second container holding a second substance, the first and second containers are each structured to provide the first and second substances to one of the two or more aerosolizers when the pod is coupled to the delivery device.

20. The delivery system of claim 19, wherein the two or more aerosolizers further comprises a third aerosolizer, and wherein the pod further comprises a third container holding a third substance, the third container structured to provide the third substance to the third aerosolizer when the pod is coupled to the delivery device.

\* \* \* \* \*